US009170254B2

(12) United States Patent
Li et al.

(10) Patent No.: US 9,170,254 B2
(45) Date of Patent: Oct. 27, 2015

(54) IDENTIFICATION OF BITTER LIGANDS THAT SPECIFICALLY ACTIVATE HUMAN T2R RECEPTORS AND RELATED ASSAYS FOR IDENTIFYING HUMAN BITTER TASTE MODULATORS

(71) Applicant: SENOMYX, INC., San Diego, CA (US)

(72) Inventors: Xiaodong Li, San Diego, CA (US); Hong Xu, San Diego, CA (US); Qing Li, San Diego, CA (US); Huixian Tang, San Diego, CA (US); Alexey Pronin, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 14/243,380

(22) Filed: Apr. 2, 2014

(65) Prior Publication Data

US 2014/0302528 A1 Oct. 9, 2014

Related U.S. Application Data

(60) Division of application No. 13/019,580, filed on Feb. 2, 2011, now Pat. No. 8,715,946, which is a continuation of application No. 11/766,974, filed on Jun. 22, 2007, now Pat. No. 7,883,856, which is a continuation-in-part of application No. 11/555,617, filed on Nov. 1, 2006, now Pat. No. 8,030,008, which is a continuation-in-part of application No. 10/191,058, filed on Jul. 10, 2002, now Pat. No. 7,338,771.

(51) Int. Cl.
*G01N 33/50* (2006.01)
*G01N 33/566* (2006.01)

(52) U.S. Cl.
CPC ........ *G01N 33/5023* (2013.01); *G01N 33/5008* (2013.01); *G01N 33/566* (2013.01); *G01N 2500/00* (2013.01)

(58) Field of Classification Search
None
See application file for complete search history.

(56) References Cited

U.S. PATENT DOCUMENTS

| 7,105,850 | B2 | 9/2006 | Wu et al. |
| 7,338,771 | B2 | 3/2008 | Pronin et al. |
| 7,413,867 | B2 | 8/2008 | Bufe et al. |
| 7,883,856 | B2 | 2/2011 | Li et al. |
| 8,030,008 | B2 | 10/2011 | Li et al. |
| 2002/0094551 | A1 | 7/2002 | Adler |
| 2011/0136112 | A1 | 6/2011 | Li et al. |

FOREIGN PATENT DOCUMENTS

| WO | 01/18050 | 3/2001 |
| WO | 2003/006482 | 1/2003 |
| WO | 2004/029087 | 4/2004 |
| WO | 2006/053771 | 5/2006 |

OTHER PUBLICATIONS

Kuhn et al., Bitter Taste Receptors for Saccharine and Acesulfame K., Nov. 10, 2004, Journal of Neuroscience, vol. 24, No. 45, pp. 10260-10265.
Adler et al., A Novel Family of Mammalian Taste Receptors, Cell, Mar. 17, 2002, vol. 100, pp. 693-702.
Chandrashekar et al., T2Rs Function as Bitter Taste Receptors, Cell, Mar. 17, 2002, vol. 100, p. 703-711.
Margolskee, Molecular Mechanisms of Bitter and Sweet Taste Transduction, The Journal of Biological Chemistry, Jan. 4, 2002, vol. 277, No. 1, pp. 1-4.
Zhang, et al, Coding of Sweet, Bitter, and Umami Tastes: Different Receptor Cells Sharing Similar Signaling Pathways, Cell, Feb. 7, 2003, vol. 112, pp. 293-301.
Parry-CM et al., PNAS 101(14830-14834)2004.
Bufe-B et al., Nature Genetics 32:397-401, 2002.
Conte-C. et al., Cytogenet. Genomic Res. 98(45-53)2002.
Shi-P. et al., Mol Biol. Evol. May 2003; 20(5):805-14.
Bowie et al., 1990, Science 247: 1306-1310.
Guo-HH et al., PNAS 101(25)9205-9210, 2004.

*Primary Examiner* — John Ulm
(74) *Attorney, Agent, or Firm* — Robin L. Teskin; LeClairRyan, a Professional Corporation

(57) ABSTRACT

The present invention relates to the discovery that specific human taste receptors in the T2R taste receptor family respond to particular bitter compounds. Also, the invention relates to the discovery of specific hT2R9 alleles and their disparate activity in functional assays with the same biter ligands. The invention further relates to the use of these T2R receptors in assays for identifying ligands that modulate the activation of these taste receptors by specific bitter ligands and related compounds. These compounds may be used as additives and/or removed from foods, beverages, cosmetics and medicinals in order to modify (block) T2R-associated bitter taste. Also T2R ligands may be used as therapeutics to treat and modulate T2R associated gastrointestinal and metabolic functions as well as treat gastrointestinal and metabolic diseases such as eating disorders, food sensing, food absorption, obesity, diabetes, Crohn's disease, celiac disease, et al.

6 Claims, 8 Drawing Sheets

Figure 4:
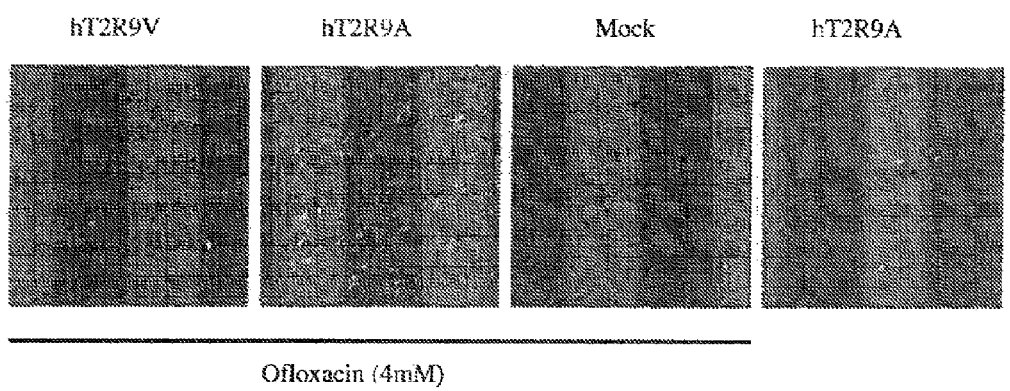

Fig. 1 Comparison of different hT2R nomenclature systems

| Senomyx | Bufe et al | Conte et al | Shi et al |
|---|---|---|---|
| hT2R01 | hTAS2R01 | | |
| hT2R03 | hTAS2R03 | | |
| hT2R04 | hTAS2R04 | | |
| hT2R05 | hTAS2R05 | | |
| hT2R07 | hTAS2R07 | | |
| hT2R08 | hTAS2R08 | | |
| hT2R09 | hTAS2R09 | | |
| hT2R10 | hTAS2R10 | | |
| hT2R13 | hTAS2R13 | | |
| hT2R14 | hTAS2R14 | | |
| hT2R16 | hTAS2R16 | | |
| hT2R24 | | | hT2R55 |
| hT2R44 | hTAS2R47 | | |
| hT2R50 | hTAS2R45 | | |
| hT2R51 | hTAS2R38 | hT2R61 | |
| hT2R54 | hTAS2R39 | hT2R57 | |
| hT2R55 | hTAS2R40 | hT2R58 | |
| hT2R61 | hTAS2R43 | hT2R52 | |
| hT2R63 | hTAS2R49 | hT2R56 | |
| hT2R64 | hTAS2R44 | hT2R53 | |
| hT2R65 | hTAS2R48 | hT2R55 | |
| hT2R67 | hTAS2R60 | hT2R51 | |
| hT2R71 | hTAS2R41 | hT2R59 | |
| hT2R75 | hTAS2R46 | hT2R54 | |
| hT2R76 | | hT2R60 | hT2R56 |

Table 2 The 23 deorphaned hT2Rs and their ligands

| Compound | 1 | 3 | 4 | 5 | 7 | 8 | 9 | 10 | 13 | 14 | 16 | 44 | 50 | 51 | 54 | 55 | 61 | 64 | 65 | 67 | 71 | 75 | 76 |
|---|---|---|---|---|---|---|---|---|---|---|---|---|---|---|---|---|---|---|---|---|---|---|---|
| Acesulfame K | + | | | | | | | | | | | | | | | | | | | | | | |
| Acetaminophen | | | | | | + | | | | | | | | | | | | | | | | | |
| 2-Acetylpyrazine | | + | | | + | + | | + | + | + | + | + | | | + | | | | + | + | | | |
| Aloin | | | | | | + | | | | | | | | | | | + | | | | | | |
| Amino-2-norbornane-carboxylic acid | | | | | | | | | | | | | | | | | | | | | | | |
| Amygdalin | | | | | | | | | | | + | | | | | | | + | | | | | |
| Andrographolide | | | | | | + | | + | | | | | | | | | | | | + | | + | |
| Arbutin, p- | | | | | | | | | | | + | | | | | | | | | | | | |
| Aristolochic acid | | | | | | | | | | + | | | | | | | + | | | | | | |
| Atropine | | | | | | + | | + | | | | | | | | | | | | | | | |
| Brucine | | | | | | | | + | + | | | | | | | | | | | | | + | + |
| 4-benzylpiperidine | | | + | | | | | + | | | | | | | | | | | | | | + | |
| Caffeine | | | | | | | | + | | | | | | | | | | | | | | | |
| Chloramphenicol | + | | | | | + | | | | | | | | | | | + | | | | | + | |
| Chloroquine | + | + | + | | + | | | + | + | | | | | | + | | + | | | | | + | |
| Cinchonine | | | + | | | | | + | | | | | | | | | | | | | | + | |
| Ciprofloxacin | | | | | | | | + | | | | | | + | | | | | | | | | |
| Clarithromycin | | | | | | | | + | + | + | | | | | | | | | | | | | |
| Clindamycin | | | | | | + | | + | + | | | | | | + | | | | | | | | |
| Cycloheximide | + | | | | | + | | | | | | | | | | | | | | | | | |
| Cyclooctanone | | | | | | + | | + | | | | | | | + | | | | | | | + | |
| Denatonium Benzoate | + | | | | | + | | + | + | + | + | + | + | | + | | | | | | | | |
| Dexamethasone | + | | + | | | | | | | | | | | | | | | | | | | + | |
| Diltiazem (HCl) | + | | + | | | + | | | | | | | | | | | | + | | | | + | |
| Diisobutylamine | | | | | | | | | | | | | | | | + | | | | | | | |
| Dimethylbiguanide | | | | | | | | | | | | | | | | | | | | | | | |
| Dimethylpiperidine, 2,6- | | | | | | | | + | | | | | | | | | | | | | | | |
| Doxepin | | | | | | | | | | | | | | | | | | + | | | | + | |
| Enalapril | | | | | | | | | | | | | | | | | | | | | | + | |
| Edrophonium | | | | + | | + | | | | | | | | | | | | | | | | | |
| Enoxacin | | | | | | | | + | | | | | | | | | | | | | | | + |

Fig. 2A

| Compound | hT2Rs | | | | | | | | | | | | | | | | | | | | | | |
|---|---|---|---|---|---|---|---|---|---|---|---|---|---|---|---|---|---|---|---|---|---|---|---|
| | 1 | 3 | 4 | 5 | 7 | 8 | 9 | 10 | 13 | 14 | 16 | 44 | 50 | 51 | 54 | 55 | 61 | 64 | 65 | 67 | 71 | 75 | 76 |
| Epicatechin (-) | + | | | | | | | | | | | | | | | | | | | | | | |
| Ethylpyrazine | | | | | + | | | | | | | | | | | | | | + | + | | + | |
| Famotidine | | + | | | | + | | | | | | + | + | | | | | + | | | | | |
| Gabapentin | | + | + | | | + | | + | | | | | | | | | | | | | | | |
| Ginkgolide A | + | | | | | | | + | | | | | | | | | | + | | | | + | |
| Goitrin | | | + | | | + | | + | + | + | | | | + | | | | | | | | + | |
| Guaiacol glyceryl ether | | | + | | | + | | | + | + | | | | | | | | | | | | | |
| Labetalol-HCl | | + | + | | | | | | | | | | | | + | | | | + | | | | |
| Linamarin | | | | | | | | | | | + | | | | | | | | | | | | |
| Lomefloxacin | + | | | | | | | | | | | | | | + | | | + | | | | + | |
| Lupinine (-) | | + | | | | + | | + | | | | | | | | | | | | | | + | |
| N-Methylthiourea | + | | + | | | | | | | | | | | | | | | | | | | | |
| 1-methy-2-quinolinone | | | + | + | + | + | | + | + | + | | | | + | + | | | | | | | + | |
| Methylprednisolone | + | | + | | | + | | + | | | | | | | | | | | | | | | |
| Nitronaphthalene | | | | | | + | | | + | + | | | | | | | | | | | | | |
| Nitrosaccharin | + | | | | | + | | | | + | | | | | | | | | | | | | |
| Ofloxacin | | | | | | | + | | | | | | | | | | + | | | | + | + | |
| Oleuropein | + | | | + | | + | | | + | + | | | | | | | | | | | | | |
| Omeprazole | + | | + | | | | | + | | | | | | | + | + | + | + | | + | | + | |
| Oxybutynin chloride | + | | + | | + | + | | + | | | | | | | + | + | + | | | | | + | |
| Oxyphenonium (HBr) | + | | + | | + | | | | + | | | | | | + | | + | | | | | + | |
| Peptide-LPFNQL | + | | | | | | | | | | | | | | | | | | | | | | |
| Peptide-LPFSQL | + | | | | | | | | | | | | | | | | | | | | | | |
| Peptide-YQEPVLGPVRGPFPIIV | + | | | | | | | | | | | | | | | | | | | | | | |
| Peptide-PVLGPVRGPFPIIV | + | | | | | | | | | | | | | | | | | | | | | | |
| Peptide-PVRGPFPIIV | + | | | | | | | | | | | | | | | | | | | | | | |
| Peptide-RGPFPIIV | + | | | | | | | | | | | | | | | | | | | | | | |
| $N^1$-ethyl-$N^5$-phenylurea | | | | | | | | | | + | | | | | | | | | | | | | |
| Picoline | | | | | | | | | | | | | | + | | + | | | | | | | |
| Picric acid | | + | | | | + | | + | | | | | | + | | | | | | | + | | |
| Pirenzepine | | | + | | | | | | | | | | | | | | | | | | | + | |
| Prednisone | + | | | | | + | | + | | + | | | | | + | | | | | | | + | + |

Fig. 2B

| Compound | hT2Rs | | | | | | | | | | | | | | | | | | | | | | |
|---|---|---|---|---|---|---|---|---|---|---|---|---|---|---|---|---|---|---|---|---|---|---|---|
| | 1 | 3 | 4 | 5 | 7 | 8 | 9 | 10 | 13 | 14 | 16 | 44 | 50 | 51 | 54 | 55 | 61 | 64 | 65 | 67 | 71 | 75 | 76 |
| Procainamide-HCl | | | + | | | | | | | | | | | | + | | | | | | | + | |
| Quassin | | | | | | + | | | | | | | | | | | | | | | | + | |
| Quinacrine | | | | | | | | | + | | | | | | | | | | | | | | |
| Quinine-HCl | + | | + | | + | | | + | | + | | | | | | + | | + | | | | + | |
| Ranitidine | + | | + | | | + | + | + | | | | | | | + | | | + | | | | + | |
| Saccharin | | | | | | + | | + | | | | | | | | | | | | | | | |
| Salicin | | | | | | | | | | | + | | | | | | | | | | | | |
| Spartein Sulfate Pentahydrate | | | | | | | | + | | | | | | | | | + | | | | | | |
| Sucrose Octaacetate | | | | | | + | | + | | | | | | | | | + | | | | | | |
| Strychnine | | | + | | + | + | | + | | | | | | | + | + | + | + | | | | + | |
| Sulfamethoxazole | + | | | | | | | | | | | | | | | | | | | | | | |
| Theobromine | | | + | | | + | | | | + | | | | | | | | | | | | | |
| Thioacetanilide | + | | | | | | | | | | | | | + | | | | | | | | | |
| Thiocarbanilide | + | | | | | | | | | | | | | | | | | | | | | | |
| Tolazoline | | | + | | | | | + | | | | | | | | | | | | | | | |
| Tolylurea | | | | | | | | + | + | + | | | | | | + | | | | | | + | |
| Trapidil | | | | | | + | | + | | + | | | | + | + | | + | | | | | | |
| Trimethoprim | | | | | + | | | | | | | | | | + | | | + | | | | + | + |
| L-Tryptophan | | | + | | | | | | | | | | | | | | | | | | | + | |

Fig. 2C

Fig. 3A

Table 3 Bitter ligands and concentration used in the assay

| Common Name | CAS | Test Concentration |
|---|---|---|
| Acesulfame K | 55589-62-3 | 25mM |
| Acetaminophen | 103-90-2 | 10mM |
| 2-Acetylpyrazine | 22047-25-2 | 10mM |
| Aloin | 1415-73-2 | 500uM |
| 2-Amino-2-norbornane-carboxylic acid | 20448-79-7 | 50mM |
| Amygdalin | | 10mM |
| Andrographolide | 5508-58-7 | 100uM |
| p-Arbutin | 497-76-7 | 5mM |
| Aristolochic acid | 313-67-7 | 20uM |
| Atropine | 101-31-5 | 1mM |
| 4-benzylpiperidine | 31252-42-3 | 250uM |
| Brucine | 357-57-3 | 250uM |
| Caffeine | 5743-12-4 | 4mM |
| Chloramphenicol | 56-75-7 | 200uM |
| Chloroquine | 132-73-0 | 10mM |
| Cinchonine | 118-10-5 | 300uM |
| Ciprofloxacin | 85721-33-1 | 500uM |
| Clarithromycin | 81103-11-9 | 250uM |
| Clindamycin | 18323-44-9 | 0.2/0.4mM |
| Cycloheximide | 66-81-9 | 2.5/5mM |
| Cyclooctanone | 502-49-8 | 5/10mM |
| Denatonium Benzoate | 3734-33-6 | 1mM |
| Dexamethasone | 50-02-2 | 500uM |
| Dilthiazem hydrochloride | 33286-22-5 | 400uM |
| Diisobutylamine | 110-96-3 | 1mM |
| Dimethylbiguanide | | 50/100mM |
| 2,6-Dimethylpiperidine | 504-03-0 | 2.5/1.25mM |
| Doxepin | 1668-19-5 | 0.15mM |
| Enalapril | | 20mM |
| Edrophonium | | 10mM |
| Enoxacin | | 0.5mM |
| Epicatechin (-) | | 4mM |
| Erythromycin | | 0.4mM |
| Ethylpyrazine | | 20mM |
| Ethyl Benzoate | | 12.5mM |
| Ethylene Thiourea | | 4.5mM |
| Famotidine | | 2.5/5mM |
| Gabapentin | | 25/50mM |
| Ginkgolide A | | 250uM |
| Goitrin | | 200uM |
| Guniacol glyceryl ether | | 5mM |
| Labetalol-HCl | | 500uM |
| Linamarin | | 20mM |
| Lomefloxacin | | 3mM |
| Lupinine, (-) | | 2.5mM |
| Methylthiourea, N- | | 10mM |

Fig. 3B

| | | |
|---|---|---|
| 1-methy-2-quinolinone | | 1.25mM |
| methylprdnisolone, 6α | | .05/.1mM |
| Nitronaphthalene | | 150uM |
| nitrosaccharin, 6- | | 0.3mm |
| Ofloxacin | | 4mM |
| Oleuropein | | 2.5mM |
| Omeprazole | | 250uM |
| Oxybutynin chloride | | 100uM |
| Oxyphenonium (HBr) | | 2.5mM |
| (P-19) LPFNQL | | 8mM |
| (P-20) LPFSQL | | 8mM |
| (P-21) PVRGPFPIIV | | 1mM |
| (P-22) RGPFPIIV | | 1mM |
| (P-24) RRPPPFFF | | 0.4mM |
| (P-25) RPKHPIKHQ | | |
| (P-26) RPFFRPFF | | 0.2mM |
| (P-29) YQEPVLGPVREPFPIIV | | 2mM |
| (P-30) PVLGPVRGPFPIIV | | 1mM |
| (P-32) VEELKPTPEGDLEIL | | |
| (P-94) RRPPFF | | 1mM |
| (P-96) RPFF | | |
| Phenylurea, N'-Ethyl-N'5 | | 5mM |
| Picoline | | 10mM |
| Picric acid | | 125uM |
| Pirenzepine | | 2.5mM |
| Prednisone | | 0.25/0.5mM |
| Procainamide-HCl | | 10mM |
| Prop.100 uM | | |
| Prop.500 uM | | |
| Prop.1mM | | 1mM |
| PTC | | 100uM |
| Quassin | | 50uM |
| Quinacrine | | 20, 40uM |
| Quinine-HCl | | 75uM |
| Ranitidine | | 10mM |
| Saccharin | | 10mM |
| Salicin | | 20mM |
| Spartein Sulfate Pentahydrate | | 0.2mM |
| Sucrose Octaacetate | | 0.2mM |
| Strychnine | | 2.5mM |
| Sulfamethoxazole | | 2.5mM |
| Theobromine | | 2.5mM |
| Thioacetanilide | | 150uM |
| Thiocarbanilide | | 0.125mM |
| Tolazoline | | 10mM |
| Tolylurea | | 2.5mM |
| Trapidil | | 1.5mM |
| Trimethoprim | | 0.75mM |
| Tryptophan,L- | | 20mM |

As shown above, hT2R9A was activated by 4mM ofloxacin whereas hT2R9V and mock-transfected cells showed no activity when contacted with the same ligand and ligand concentration.

Figure 5:
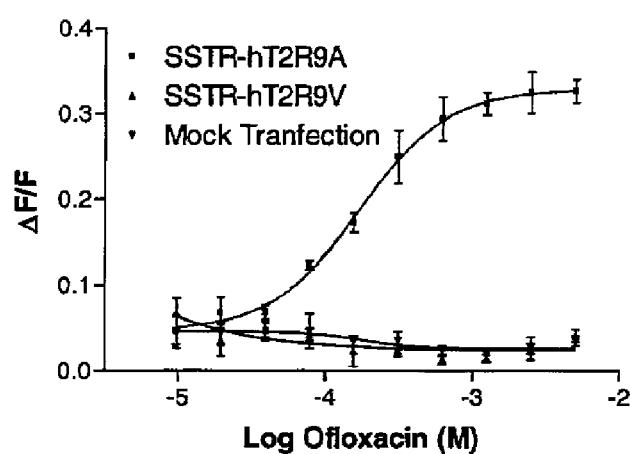

As disclosed herein, ranitidine is a ligand for hT2R9. As shown in Figure 5 above, only hT2R9A but not hT2R9V is activated by ranitidine at 5 and 10 mM

SEQUENCE LISTING

```
<160> NUMBER OF SEQ ID NOS: 59

<210> SEQ ID NO 1
<211> LENGTH: 35
<212> TYPE: PRT
<213> ORGANISM: Artificial Sequence
<220> FEATURE:
<223> OTHER INFORMATION: Synthetic peptide

<400> SEQUENCE: 1

Met Asn Gly Thr Glu Gly Pro Asn Phe Tyr Val Pro Phe Ser Asn Lys
 1               5                  10                  15

Thr Gly Val Val Arg Ser Pro Phe Glu Ala Pro Gln Tyr Tyr Leu Ala
            20                  25                  30

Glu Pro Trp
        35

<210> SEQ ID NO 2
<211> LENGTH: 374
<212> TYPE: PRT
<213> ORGANISM: Artificial Sequence
<220> FEATURE:
<223> OTHER INFORMATION: Synthetic peptide construct

<400> SEQUENCE: 2

Met Ala Arg Ser Leu Thr Trp Arg Cys Cys Pro Trp Cys Leu Thr Glu
 1               5                  10                  15

Asp Glu Lys Ala Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu Leu
        35                  40                  45

Gly Pro Gly Glu Ser Gly Lys Ser Thr Phe Ile Lys Gln Met Arg Ile
    50                  55                  60
```

| | | | | | | | | | | | | | | |
|---|---|---|---|---|---|---|---|---|---|---|---|---|---|---|
|Ile|His|Gly|Ala|Gly|Tyr|Ser|Glu|Glu|Arg|Lys|Gly|Phe|Arg|Pro|
|65| | | |70| | | |75| | | |80| | |

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Met Gln Trp Leu Trp Arg Asp Ala Gly Ile
    130                 135                 140

Arg Ala Cys Tyr Glu Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
            195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
            275                 280                 285

Ser His Leu Ala Thr Tyr Phe Pro Ser Phe Gln Gly Pro Lys Gln Asp
        290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Leu Lys Lys Glu Asp
                325                 330                 335

Lys Glu Ile Tyr Ser His Met Thr Cys Ala Thr Asp Thr Gln Asn Val
            340                 345                 350

Lys Phe Val Phe Asp Ala Val Thr Asp Ile Ile Ile Lys Glu Asn Leu
        355                 360                 365

Lys Asp Cys Gly Leu Phe
    370

<210> SEQ ID NO 3
<211> LENGTH: 900
<212> TYPE: DNA
<213> ORGANISM: Homo sapiens

<400> SEQUENCE: 3
atgctagagt ctcacctcat tatctatttt cttcttgcag tgatacaatt tcttcttggg     60
attttcacaa atggcatcat tgtggtggtg aatggcattg acttgatcaa gcacagaaaa    120
atggctccgc tggatctcct tctttcttgt ctggcagttt ctagaatttt tctgcagttg    180
ttcatcttct acgttaatgt gattgttatc ttcttcatag aattcatcat gtgttctgcg    240
aattgtgcaa ttctccttat tatcaatgaa ttggaacttt ggcttgccac atggctcggc    300
gttttctatt gtgccaaggt tgccagcgtc cgtcacccac tcttcatctg gttgaagatg    360

-continued

```
aggatatcca agctggtccc atggatgatc ctggggtctc tgctatatgt atctatgatt    420
tgtgttttcc atagcaaata tgcagggttt atggtcccat acttcctaag gaaattttc     480 tcccaaaatg ccacaattca aaagaagat  acactggcta tacagatttt ctcttttgtt    540
gctgagttct cagtgccatt gcttatcttc cttttgctg  ttttgctctt gattttctct    600
ctggggaggc acacccggca aatgagaaac acagtggccg gcagcagggt tcctggcagg    660
ggtgcaccca tcagcgcgtt gctgtctatc ctgtccttcc tgatcctcta cttctcccac    720
tgcatgataa agttttttct ctcttctcta agtttcaca  tcagaaggtt catctttctg    780
ttcttcatcc ttgtgattgg tatatacct  tctggacact ctctcatctt aattttagga    840
aatcctaaat tgaaacaaaa tgcaaaaaag ttcctcctcc acagtaagtg ctgtcagtga    900
```

<210> SEQ ID NO 4
<211> LENGTH: 299
<212> TYPE: PRT
<213> ORGANISM: Homo sapiens

<400> SEQUENCE: 4

```
Met Leu Glu Ser His Leu Ile Ile Tyr Phe Leu Leu Ala Val Ile Gln
  1               5                  10                  15

Phe Leu Leu Gly Ile Phe Thr Asn Gly Ile Ile Val Val Asn Gly
                 20                  25                  30

Ile Asp Leu Ile Lys His Arg Lys Met Ala Pro Leu Asp Leu Leu Leu
             35                  40                  45

Ser Cys Leu Ala Val Ser Arg Ile Phe Leu Gln Leu Phe Ile Phe Tyr
         50                  55                  60

Val Asn Val Ile Val Ile Phe Phe Ile Glu Phe Ile Met Cys Ser Ala
 65                  70                  75                  80

Asn Cys Ala Ile Leu Leu Phe Ile Asn Glu Leu Glu Leu Trp Leu Ala
                 85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
    130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
```

```
            275                 280                 285
Lys Lys Phe Leu Leu His Ser Lys Cys Cys Gln
    290                 295

<210> SEQ ID NO 5
<211> LENGTH: 951
<212> TYPE: DNA
<213> ORGANISM: Homo sapiens

<400> SEQUENCE: 5
atgatgggac tcaccgaggg ggtgttcctg attctgtctg gcactcagtt cacactggga      60
attctggtca attgtttcat tgagttggtc aatggtagca gctggttcaa gaccaagaga     120
atgtctttgt ctgacttcat catcaccacc ctggcactct tgaggatcat tctgctgtgt     180
attatcttga ctgatagttt tttaatagaa ttctctccca acacacatga ttcagggata     240
ataatgcaaa ttattgatgt ttcctggaca tttacaaacc atctgagcat ttggcttgcc     300
acctgtcttg gtgtcctcta ctgcctgaaa atcgccagtt tctctcaccc acattcctc      360 tggctcaagt ggagagtttc tagggtgatg gtatggatgc tgttgggtgc actgctctta     420
tcctgtggta gtaccgcatc tctgatcaat gagtttaagc tctattctgt ctttagggga     480
attgaggcca ccaggaatgt gactgaacac ttcagaaaga agaggagtga gtattatctg     540
atccatgttc ttgggactct gtggtacctg cctcccttaa ttgtgtccct ggcctcctac     600
tctttgctca tcttctccct ggggaggcac acacggcaga tgctgcaaaa tgggacaagc     660
tccagagatc caaccactga ggcccacaag agggccatca gaatcatcct ttccttcttc     720
tttctcttct actttactt tcttgctttc ttaattgcat catttggtaa tttcctacca      780
aaaaccaaga tggctaagat gattggcgaa gtaatgacaa tgttttatcc tgctggccac     840
tcatttattc tcattctggg gaacagtaag ctgaagcaga catttgtagt gatgctccgg     900
tgtgagtctg gtcatctgaa gcctggatcc aagggaccca ttttctctta g              951

<210> SEQ ID NO 6
<211> LENGTH: 316
<212> TYPE: PRT
<213> ORGANISM: Homo sapiens

<400> SEQUENCE: 6

Met Met Gly Leu Thr Glu Gly Val Phe Leu Ile Leu Ser Gly Thr Gln
  1               5                  10                  15

Phe Thr Leu Gly Ile Leu Val Asn Cys Phe Ile Glu Leu Val Asn Gly
             20                  25                  30

Ser Ser Trp Phe Lys Thr Lys Arg Met Ser Leu Ser Asp Phe Ile Ile
         35                  40                  45

Thr Thr Leu Ala Leu Leu Arg Ile Ile Leu Leu Cys Ile Ile Leu Thr
     50                  55                  60

Asp Ser Phe Leu Ile Glu Phe Ser Pro Asn Thr His Asp Ser Gly Ile
 65                  70                  75                  80

Ile Met Gln Ile Ile Asp Val Ser Trp Thr Phe Thr Asn His Leu Ser
                 85                  90                  95

Ile Trp Leu Ala Thr Cys Leu Gly Val Leu Tyr Cys Leu Lys Ile Ala
            100                 105                 110

Ser Phe Ser His Pro Thr Phe Leu Trp Leu Lys Trp Arg Val Ser Arg
        115                 120                 125

Val Met Val Trp Met Leu Leu Gly Ala Leu Leu Leu Ser Cys Gly Ser
    130                 135                 140
```

Thr Ala Ser Leu Ile Asn Glu Phe Lys Leu Tyr Ser Val Phe Arg Gly
145                 150                 155                 160

Ile Glu Ala Thr Arg Asn Val Thr Glu His Phe Arg Lys Lys Arg Ser
            165                 170                 175

Glu Tyr Tyr Leu Ile His Val Leu Gly Thr Leu Trp Tyr Leu Pro Pro
        180                 185                 190

Leu Ile Val Ser Leu Ala Ser Tyr Ser Leu Leu Ile Phe Ser Leu Gly
    195                 200                 205

Arg His Thr Arg Gln Met Leu Gln Asn Gly Thr Ser Ser Arg Asp Pro
210                 215                 220

Thr Thr Glu Ala His Lys Arg Ala Ile Arg Ile Ile Leu Ser Phe Phe
225                 230                 235                 240

Phe Leu Phe Leu Leu Tyr Phe Leu Ala Phe Leu Ile Ala Ser Phe Gly
            245                 250                 255

Asn Phe Leu Pro Lys Thr Lys Met Ala Lys Met Ile Gly Glu Val Met
        260                 265                 270

Thr Met Phe Tyr Pro Ala Gly His Ser Phe Ile Leu Ile Leu Gly Asn
    275                 280                 285

Ser Lys Leu Lys Gln Thr Phe Val Val Met Leu Arg Cys Glu Ser Gly
290                 295                 300

His Leu Lys Pro Gly Ser Lys Gly Pro Ile Phe Ser
305                 310                 315

<210> SEQ ID NO 7
<211> LENGTH: 900
<212> TYPE: DNA
<213> ORGANISM: Homo sapiens

<400> SEQUENCE: 7
atgctgagcg ctggcctagg actgctgatg ctggtggcag tggttgaatt tctcatcggt      60
ttaattggaa atggaatcct ggtggtctgg agttttagag aatggatcag aaaattcaac     120
tggtcctcat ataacctcat tatcctgggc ctggctggct gccgatttct cctgcagtgg     180
ctgatcattt tggacttaag cttgtttcca cttttccaga gcagccgttg gcttcgctat     240
cttagtatct tctgggtcct ggtaagccag gccagcttat ggtttgccac cttcctcagt     300
gtcttctatt gcaagaagat cacgaccttc gatcgcccgg cctacttgtg gctgaagcag     360
agggcctata acctgagtct ctggtgcctt ctgggctact ttataatcaa tttgttactt     420
acagtccaaa ttggcttaac attctatcat cctccccaag aaacagcag cattcggtat      480 ccctttgaaa gctggcagta cctgtatgca tttcagctca attcaggaag ttatttgcct     540
ttagtggtgt tcttgtttc ctctgggatg ctgattgtct cttgtatac acaccacaag       600 aagatgaagg tccattcagc tggtaggagg gatgtccggg ccaaggctca catcactgcg     660
ctgaagtcct tgggctgctt cctcttactt cacctggttt atatcatggc cagcccttc      720 tccatcacct ccaagactta tcctcctgat ctcaccagtg tcttcatctg ggagacactc     780
atggcagcct atccttctct tcattctctc atattgatca tggggattcc tagggtgaag     840
cagacttgtc agaagatcct gtggaagaca gtgtgtgctc ggagatgctg ggcccatga    900

<210> SEQ ID NO 8
<211> LENGTH: 299
<212> TYPE: PRT
<213> ORGANISM: Homo sapiens

<400> SEQUENCE: 8

```
Met Leu Ser Ala Gly Leu Gly Leu Leu Met Leu Val Ala Val Val Glu
  1               5                  10                  15

Phe Leu Ile Gly Leu Ile Gly Asn Gly Ile Leu Val Val Trp Ser Phe
             20                  25                  30

Arg Glu Trp Ile Arg Lys Phe Asn Trp Ser Ser Tyr Asn Leu Ile Ile
         35                  40                  45

Leu Gly Leu Ala Gly Cys Arg Phe Leu Leu Gln Trp Leu Ile Ile Leu
     50                  55                  60

Asp Leu Ser Leu Phe Pro Leu Phe Gln Ser Ser Arg Trp Leu Arg Tyr
 65              70                  75                  80

Leu Ser Ile Phe Trp Val Leu Val Ser Gln Ala Ser Leu Trp Phe Ala
             85                  90                  95

Thr Phe Leu Ser Val Phe Tyr Cys Lys Lys Ile Thr Thr Phe Asp Arg
            100                 105                 110

Pro Ala Tyr Leu Trp Leu Lys Gln Arg Ala Tyr Asn Leu Ser Leu Trp
        115                 120                 125

Cys Leu Leu Gly Tyr Phe Ile Ile Asn Leu Leu Leu Thr Val Gln Ile
    130                 135                 140

Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
            165                 170                 175

Ser Tyr Leu Pro Leu Val Val Phe Leu Val Ser Ser Gly Met Leu Ile
            180                 185                 190

Val Ser Leu Tyr Thr His His Lys Lys Met Lys Val His Ser Ala Gly
        195                 200                 205

Arg Arg Asp Val Arg Ala Lys Ala His Ile Thr Ala Leu Lys Ser Leu
210                 215                 220

Gly Cys Phe Leu Leu Leu His Leu Val Tyr Leu Met Ala Ser Pro Phe
225                 230                 235                 240

Ser Ile Thr Ser Lys Thr Tyr Pro Pro Asp Leu Thr Ser Val Phe Ile
            245                 250                 255

Trp Glu Thr Leu Met Ala Ala Tyr Pro Ser Leu His Ser Leu Ile Leu
            260                 265                 270

Ile Met Gly Ile Pro Arg Val Lys Gln Thr Cys Gln Lys Ile Leu Trp
            275                 280                 285

Lys Thr Val Cys Ala Arg Cys Trp Gly Pro
290                 295
```

<210> SEQ ID NO 9
<211> LENGTH: 957
<212> TYPE: DNA
<213> ORGANISM: Homo sapiens

<400> SEQUENCE: 9

| | | | | | | |
|---|---|---|---|---|---|---|
| atggcagata | aagtgcagac | tactttattg | ttcttagcag | ttggagagtt | ttcagtgggg | 60 |
| atcttaggga | atgcattcat | tggattggta | aactgcatgg | actgggtcaa | gaagaggaaa | 120 |
| attgcctcca | ttgatttaat | cctcacaagt | ctggccatat | ccagaatttg | tctattgtgc | 180 |
| gtaatactat | tagattgttt | tatattggtg | ctatatccag | atgtctatgc | cactggtaaa | 240 |
| gaaatgagaa | tcattgactt | cttctggaca | ctaaccaatc | atttaagtat | ctggtttgca | 300 |
| acctgcctca | gcatttacta | tttcttcaag | ataggtaatt | tctttcaccc | acttttcctc | 360 |
| tggatgaagt | ggagaattga | cagggtgatt | tcctggattc | tactgggtg | cgtggttctc | 420 |

-continued

```
tctgtgttta ttagccttcc agccactgag aatttgaacg ctgatttcag gttttgtgtg      480
aaggcaaaga ggaaaacaaa cttaacttgg agttgcagaa taaataaaac tcaacatgct      540
tctaccaagt tatttctcaa cctggcaacg ctgctcccct tttgtgtgtg cctaatgtcc      600 ttttttcctct tgatcctctc cctgcggaga catatcaggc gaatgcagct cagtgccaca     660
gggtgcagag accccagcac agaagcccat gtgagagccc tgaaagctgt catttccttc      720
cttctcctct ttattgccta ctatttgtcc tttctcattg ccacctccag ctactttatg      780
ccagagacgg aattagctgt gattttggt gagtccatag ctctaatcta cccctcaagt       840
cattcattta tcctaaatact ggggaacaat aaattaagac atgcatctct aaaggtgatt     900
tggaaagtaa tgtctattct aaaaggaaga aaattccaac aacataaaca aatctga         957
```

<210> SEQ ID NO 10
<211> LENGTH: 318
<212> TYPE: PRT
<213> ORGANISM: Homo sapiens

<400> SEQUENCE: 10

```
Met Ala Asp Lys Val Gln Thr Thr Leu Leu Phe Leu Ala Val Gly Glu
1               5                   10                  15

Phe Ser Val Gly Ile Leu Gly Asn Ala Phe Ile Gly Leu Val Asn Cys
            20                  25                  30

Met Asp Trp Val Lys Lys Arg Lys Ile Ala Ser Ile Asp Leu Ile Leu
        35                  40                  45

Thr Ser Leu Ala Ile Ser Arg Ile Cys Leu Leu Cys Val Ile Leu Leu
    50                  55                  60

Asp Cys Phe Ile Leu Val Leu Tyr Pro Asp Val Tyr Ala Thr Gly Lys
65                  70                  75                  80

Glu Met Arg Ile Ile Asp Phe Phe Trp Thr Leu Thr Asn His Leu Ser
                85                  90                  95

Ile Trp Phe Ala Thr Cys Leu Ser Ile Tyr Tyr Phe Phe Lys Ile Gly
            100                 105                 110

Asn Phe Phe His Pro Leu Phe Leu Trp Met Lys Trp Arg Ile Asp Arg
        115                 120                 125

Val Ile Ser Trp Ile Leu Leu Gly Cys Val Val Leu Ser Val Phe Ile
    130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
        195                 200                 205

Arg Arg His Ile Arg Arg Met Gln Leu Ser Ala Thr Gly Cys Arg Asp
    210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
```

```
                275                 280                 285
Asn Asn Lys Leu Arg His Ala Ser Leu Lys Val Ile Trp Lys Val Met
            290                 295                 300

Ser Ile Leu Lys Gly Arg Lys Phe Gln Gln His Lys Gln Ile
305                 310                 315

<210> SEQ ID NO 11
<211> LENGTH: 930
<212> TYPE: DNA
<213> ORGANISM: Homo sapiens

<400> SEQUENCE: 11
atgttcagtc ctgcagataa catctttata atcctaataa ctggagaatt catactagga      60
atattgggga atggatacat tgcactagtc aactggattg actggattaa gaagaaaaag     120
atttccacag ttgactacat ccttaccaat ttagttatcg ccagaatttg tttgatcagt     180
gtaatggttg taaatggcat tgtaatagta ctgaacccag atgtttatac aaaaaataaa     240
caacagatag tcattttac cttctggaca tttgccaact acttaaatat gtggattacc      300
acctgcctta atgtcttcta ttttctgaag atagccagtt cctctcatcc acttttctc     360 tggctgaagt ggaaaattga tatggtggtg cactggatcc tgctgggatg ctttgccatt     420
tccttgttgg tcagccttat agcagcaata gtactgagtt gtgattatag gtttcatgca     480
attgccaaac ataaaagaaa cattactgaa atgttccatg tgagtaaaat accatacttt     540 gaaccttaa ctctctttaa cctgtttgca attgtcccat ttattgtgtc actgatatca      600
tttttccttt tagtaagatc tttatggaga cataccaagc aaataaaact ctatgctacc     660
ggcagtagag accccagcac agaagttcat gtgagagcca ttaaaactat gacttcattt     720
atcttctttt ttttcctata ctatattct tctattttga tgacctttag ctatcttatg      780
acaaaataca gttagctgt ggagtttgga gagattgcag caattctcta cccccttggt      840
cactcactta ttttaattgt tttaaataat aaactgaggc agacatttgt cagaatgctg     900
acatgtagaa aaattgcctg catgatatga                                       930

<210> SEQ ID NO 12
<211> LENGTH: 309
<212> TYPE: PRT
<213> ORGANISM: Homo sapiens

<400> SEQUENCE: 12

Met Phe Ser Pro Ala Asp Asn Ile Phe Ile Ile Leu Ile Thr Gly Glu
  1               5                  10                  15

Phe Ile Leu Gly Ile Leu Gly Asn Gly Tyr Ile Ala Leu Val Asn Trp
                 20                  25                  30

Ile Asp Trp Ile Lys Lys Lys Ile Ser Thr Val Asp Tyr Ile Leu
             35                  40                  45

Thr Asn Leu Val Ile Ala Arg Ile Cys Leu Ile Ser Val Met Val Val
         50                  55                  60

Asn Gly Ile Val Ile Val Leu Asn Pro Asp Val Tyr Thr Lys Asn Lys
 65                  70                  75                  80

Gln Gln Ile Val Ile Phe Thr Phe Trp Thr Phe Ala Asn Tyr Leu Asn
                 85                  90                  95

Met Trp Ile Thr Thr Cys Leu Asn Val Phe Tyr Phe Leu Lys Ile Ala
                100                 105                 110

Ser Ser Ser His Pro Leu Phe Leu Trp Leu Lys Trp Lys Ile Asp Met
            115                 120                 125
```

Val Val His Trp Ile Leu Leu Gly Cys Phe Ala Ile Ser Leu Leu Val
    130                 135                 140

Ser Leu Ile Ala Ala Ile Val Leu Ser Cys Asp Tyr Arg Phe His Ala
145                 150                 155                 160

Ile Ala Lys His Lys Arg Asn Ile Thr Glu Met Phe His Val Ser Lys
                165                 170                 175

Ile Pro Tyr Phe Glu Pro Leu Thr Leu Phe Asn Leu Phe Ala Ile Val
                180                 185                 190

Pro Phe Ile Val Ser Leu Ile Ser Phe Phe Leu Leu Val Arg Ser Leu
            195                 200                 205

Trp Arg His Thr Lys Gln Ile Lys Leu Tyr Ala Thr Gly Ser Arg Asp
        210                 215                 220

Pro Ser Thr Glu Val His Val Arg Ala Ile Lys Thr Met Thr Ser Phe
225                 230                 235                 240

Ile Phe Phe Phe Leu Tyr Tyr Ile Ser Ser Ile Leu Met Thr Phe
                245                 250                 255

Ser Tyr Leu Met Thr Lys Tyr Lys Leu Ala Val Glu Phe Gly Glu Ile
                260                 265                 270

Ala Ala Ile Leu Tyr Pro Leu Gly His Ser Leu Ile Leu Ile Val Leu
                275                 280                 285

Asn Asn Lys Leu Arg Gln Thr Phe Val Arg Met Leu Thr Cys Arg Lys
290                 295                 300

Ile Ala Cys Met Ile
305

<210> SEQ ID NO 13
<211> LENGTH: 939
<212> TYPE: DNA
<213> ORGANISM: Homo sapiens

<400> SEQUENCE: 13
atgccaagtg caatagaggc aatatatatt attttaattg ctggtgaatt gaccataggg      60
atttggggaa atggattcat tgtactagtt aactgcattg actggctcaa agaagagat     120 atttccttga ttgacatcat cctgatcagc ttggccatct ccagaatctg tctgctgtgt     180
gtaatatcat tagatggctt ctttatgctg ctctttccag gtacatatgg caatagcgtg     240
ctagtaagca ttgtgaatgt tgtctggaca tttgccaata attcaagtct ctggtttact     300
tcttgcctca gtatcttcta tttactcaag atagccaata tatcgcaccc attttctt c    360 tggctgaagc taaagatcaa caaggtcatg cttgcgattc ttctggggtc ctttcttatc     420 tcttaatta ttagtgttcc aaagaatgat gatatgtggt atcacctttt caaagtcagt      480
catgaagaaa acattacttg gaaattcaaa gtgagtaaaa ttccaggtac tttcaaacag     540
ttaaccctga acctgggggt gatggttccc tttatccttt gcctgatctc attttcttg      600 ttactttct ccctagttag acacaccaag cagattcgac tgcatgctac agggttcaga     660
gaccccagta cagaggccca catgagggcc ataaaggcag tgatcatctt tctgctcctc     720
ctcatcgtgt actacccagt ctttcttgtt atgacctcta gcgctctgat tcctcaggga     780
aaattagtgt tgatgattgg tgacatagta actgtcattt tcccatcaag ccattcattc     840
attctaatta tgggaaatag caagttgagg gaagcttttc tgaagatgtt aagatttgtg     900 aagtgttttcc ttagaagaag aaagccttttt gttccatag                          939

<210> SEQ ID NO 14

<211> LENGTH: 312
<212> TYPE: PRT
<213> ORGANISM: Homo sapiens

<400> SEQUENCE: 14

Met Pro Ser Ala Ile Glu Ala Ile Tyr Ile Ile Leu Ile Ala Gly Glu
1               5                   10                  15

Leu Thr Ile Gly Ile Trp Gly Asn Gly Phe Ile Val Leu Val Asn Cys
            20                  25                  30

Ile Asp Trp Leu Lys Arg Arg Asp Ile Ser Leu Ile Asp Ile Ile Leu
        35                  40                  45

Ile Ser Leu Ala Ile Ser Arg Ile Cys Leu Leu Cys Val Ile Ser Leu
    50                  55                  60

Asp Gly Phe Phe Met Leu Leu Phe Pro Gly Thr Tyr Gly Asn Ser Val
65                  70                  75                  80

Leu Val Ser Ile Val Asn Val Val Trp Thr Phe Ala Asn Asn Ser Ser
                85                  90                  95

Leu Trp Phe Thr Ser Cys Leu Ser Ile Phe Tyr Leu Leu Lys Ile Ala
            100                 105                 110

Asn Ile Ser His Pro Phe Phe Phe Trp Leu Lys Leu Lys Ile Asn Lys
        115                 120                 125

Val Met Leu Ala Ile Leu Leu Gly Ser Phe Leu Ile Ser Leu Ile Ile
130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Phe Ser Leu Val Arg His
        195                 200                 205

Thr Lys Gln Ile Arg Leu His Ala Thr Gly Phe Arg Asp Pro Ser Thr
    210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270

Ile Phe Pro Ser Ser His Ser Phe Ile Leu Ile Met Gly Asn Ser Lys
        275                 280                 285

Leu Arg Glu Ala Phe Leu Lys Met Leu Arg Phe Val Lys Cys Phe Leu
    290                 295                 300

Arg Arg Arg Lys Pro Phe Val Pro
305                 310

<210> SEQ ID NO 15
<211> LENGTH: 939
<212> TYPE: DNA
<213> ORGANISM: Homo sapiens

<400> SEQUENCE: 15
atgccaagtg caatagaggc aatatatatt attttaattg ctggtgaatt gaccataggg      60
atttggggaa atggattcat tgtactagtt aactgcattg actggctcaa agaagagat     120 atttccttga ttgacatcat cctgatcagc ttggccatct ccagaatctg tctgctgtgt    180

```
gtaatatcat tagatggctt ctttatgctg ctctttccag gtacatatgg caatagcgtg      240
ctagtaagca ttgtgaatgt tgtctggaca tttgccaata attcaagtct ctggtttact      300
tcttgcctca gtatcttcta tttactcaag atagccaata tatcgcaccc attttcttc       360 tggctgaagc taaagatcaa caaggtcatg cttgcgattc ttctggggtc ctttcttatc      420
tctttaatta ttagtgttcc aaagaatgat gatatgtggt atcaccttt caaagtcagt       480 catgaagaaa acattacttg gaaattcaaa gtgagtaaaa ttccaggtac tttcaaacag      540
ttaaccctga acctgggggc gatggttccc tttatccttt gcctgatctc attttcttg       600 ttacttttct ccctagttag acacaccaag cagattcgac tgcatgctac agggttcaga      660
gaccccagta cagaggccca catgagggcc ataaaggcag tgatcatctt tctgctcctc      720
ctcatcgtgt actacccagt ctttcttgtt atgacctcta cgctctgat tcctcaggga      780 aaattagtgt tgatgattgg tgacatagta actgtcattt tcccatcaag ccattcattc      840
attctaatta tgggaaatag caagttgagg gaagcttttc tgaagatgtt aagatttgtg      900
aagtgtttcc ttagaagaag aaagcctttt gttccatag                             939
```

<210> SEQ ID NO 16
<211> LENGTH: 312
<212> TYPE: PRT
<213> ORGANISM: Homo sapiens

<400> SEQUENCE: 16

```
Met Pro Ser Ala Ile Glu Ala Ile Tyr Ile Ile Leu Ile Ala Gly Glu
  1               5                  10                  15

Leu Thr Ile Gly Ile Trp Gly Asn Gly Phe Ile Val Leu Val Asn Cys
             20                  25                  30

Ile Asp Trp Leu Lys Arg Arg Asp Ile Ser Leu Ile Asp Ile Ile Leu
         35                  40                  45

Ile Ser Leu Ala Ile Ser Arg Ile Cys Leu Leu Cys Val Ile Ser Leu
     50                  55                  60

Asp Gly Phe Phe Met Leu Leu Phe Pro Gly Thr Tyr Gly Asn Ser Val
 65                  70                  75                  80

Leu Val Ser Ile Val Asn Val Val Trp Thr Phe Ala Asn Asn Ser Ser
                 85                  90                  95

Leu Trp Phe Thr Ser Cys Leu Ser Ile Phe Tyr Leu Leu Lys Ile Ala
            100                 105                 110

Asn Ile Ser His Pro Phe Phe Phe Trp Leu Lys Leu Lys Ile Asn Lys
        115                 120                 125

Val Met Leu Ala Ile Leu Leu Gly Ser Phe Leu Ile Ser Leu Ile Ile
    130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Ala Pro Phe Ile
            180                 185                 190

Leu Cys Leu Ile Ser Phe Phe Leu Leu Phe Ser Leu Val Arg His
        195                 200                 205

Thr Lys Gln Ile Arg Leu His Ala Thr Gly Phe Arg Asp Pro Ser Thr
    210                 215                 220

Glu Ala His Met Arg Ala Ile Lys Ala Val Ile Ile Phe Leu Leu Leu
225                 230                 235                 240
```

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270

Ile Phe Pro Ser Ser His Ser Phe Ile Leu Ile Met Gly Asn Ser Lys
        275                 280                 285

Leu Arg Glu Ala Phe Leu Lys Met Leu Arg Phe Val Lys Cys Phe Leu
    290                 295                 300

Arg Arg Arg Lys Pro Phe Val Pro
305                 310

<210> SEQ ID NO 17
<211> LENGTH: 924
<212> TYPE: DNA
<213> ORGANISM: Homo sapiens

<400> SEQUENCE: 17
atgctacgtg tagtggaagg catcttcatt tttgttgtag ttagtgagtc agtgtttggg     60
gttttgggga tggatttat tggacttgta aactgcattg actgtgccaa gaataagtta    120
tctacgattg ctttattct caccggctta gctatttcaa gaattttct gatatggata    180 ataattacag atggatttat acagatattc tctccaaata tatgcctc cggtaaccta    240 attgaatata ttagttactt tgggtaatt ggtaatcaat caagtatgtg gtttgccacc    300
agcctcagca tcttctattt cctgaagata gcaaattttt ccaactacat atttctctgg    360
ttgaagagca gaacaaatat ggttcttccc ttcatgatag tattcttact tatttcatcg    420
ttacttaatt ttgcatacat tgcgaagatt cttaatgatt ataaaacgaa gaatgacaca    480
gtctgggatc tcaacatgta taaaagtgaa tactttatca agcagatttt gctaaatctg    540
ggagtcattt tcttctttac actatcccta attacatgta ttttttttaat catttccctt    600 tggagacaca acaggcagat gcaatcgaat gtgacaggat tgagagactc caacacagaa    660
gctcatgtga aggcaatgaa agttttgata tctttcatca tcctctttat cttgtatttt    720
ataggcatgg ccatagaaat atcatgtttt actgtgcgag aaaacaaact gctgcttatg    780
tttggaatga caaccacagc catctatccc tggggtcact catttatctt aattctagga    840
aacagcaagc taaagcaagc ctcttttgagg gtactgcagc aattgaagtg ctgtgagaaa    900
aggaaaaatc tcagagtcac atag                                           924

<210> SEQ ID NO 18
<211> LENGTH: 307
<212> TYPE: PRT
<213> ORGANISM: Homo sapiens

<400> SEQUENCE: 18

Met Leu Arg Val Val Glu Gly Ile Phe Ile Phe Val Val Val Ser Glu
1               5                   10                  15

Ser Val Phe Gly Val Leu Gly Asn Gly Phe Ile Gly Leu Val Asn Cys
            20                  25                  30

Ile Asp Cys Ala Lys Asn Lys Leu Ser Thr Ile Gly Phe Ile Leu Thr
        35                  40                  45

Gly Leu Ala Ile Ser Arg Ile Phe Leu Ile Trp Ile Ile Thr Asp
    50                  55                  60

Gly Phe Ile Gln Ile Phe Ser Pro Asn Ile Tyr Ala Ser Gly Asn Leu
65                  70                  75                  80

| | | | | | | | | | | | |
|---|---|---|---|---|---|---|---|---|---|---|---|
| Ile | Glu | Tyr | Ile | Ser | Tyr | Phe | Trp | Val | Ile | Gly | Asn | Gln | Ser | Ser | Met |
| | | | | 85 | | | | 90 | | | | 95 | | | |

Ile Glu Tyr Ile Ser Tyr Phe Trp Val Ile Gly Asn Gln Ser Ser Met
                        85                    90                    95

Trp Phe Ala Thr Ser Leu Ser Ile Phe Tyr Phe Leu Lys Ile Ala Asn
        100                    105                    110

Phe Ser Asn Tyr Ile Phe Leu Trp Leu Lys Ser Arg Thr Asn Met Val
            115                    120                    125

Leu Pro Phe Met Ile Val Phe Leu Leu Ile Ser Ser Leu Leu Asn Phe
      130                    135                    140

Ala Tyr Ile Ala Lys Ile Leu Asn Asp Tyr Thr Lys Asn Asp Thr
145                  150                    155                    160

Val Trp Asp Leu Asn Met Tyr Lys Ser Glu Tyr Phe Ile Lys Gln Ile
            165                    170                    175

Leu Leu Asn Leu Gly Val Ile Phe Phe Phe Thr Leu Ser Leu Ile Thr
            180                    185                    190

Cys Ile Phe Leu Ile Ile Ser Leu Trp Arg His Asn Arg Gln Met Gln
            195                    200                    205

Ser Asn Val Thr Gly Leu Arg Asp Ser Asn Thr Glu Ala His Val Lys
          210                    215                    220

Ala Met Lys Val Leu Ile Ser Phe Ile Ile Leu Phe Ile Leu Tyr Phe
225                  230                    235                    240

Ile Gly Met Ala Ile Glu Ile Ser Cys Phe Thr Val Arg Glu Asn Lys
                245                    250                    255

Leu Leu Leu Met Phe Gly Met Thr Thr Thr Ala Ile Tyr Pro Trp Gly
          260                    265                    270

His Ser Phe Ile Leu Ile Leu Gly Asn Ser Lys Leu Lys Gln Ala Ser
            275                    280                    285

Leu Arg Val Leu Gln Gln Leu Lys Cys Cys Glu Lys Arg Lys Asn Leu
      290                    295                    300

Arg Val Thr
305

<210> SEQ ID NO 19
<211> LENGTH: 912
<212> TYPE: DNA
<213> ORGANISM: Homo sapiens

<400> SEQUENCE: 19

```
atggaaagtg ccctgccgag tatcttcact cttgtaataa ttgcagaatt cataattggg     60
aatttgagca atggatttat agtactgatc aactgcattg actgggtcag taaagagag    120
ctgtcctcag tcgataaact cctcattatc ttggcaatct ccagaattgg gctgatctgg    180
gaaatattag taagttggtt tttagctctg cattatctag ccatatttgt gtctggaaca    240
ggattaagaa ttatgatttt tagctggata gtttctaatc acttcaatct ctggcttgct    300
acaatcttca gcatctttta tttgctcaaa atagcgagtt tctctagccc tgcttttctc    360
tatttgaagt ggagagtaaa caaagtgatt ctgatgatac tgctaggaac cttggtcttc    420
ttatttttaa atctgataca aataaacatg catataaaag actggctgga ccgatatgaa    480
agaaacacaa cttggaattt cagtatgagt gactttgaaa cattttcagt gtcggtcaaa    540
ttcactatga ctatgttcag tctaacacca tttactgtgg ccttcatctc ttttctcctg    600
ttaattttct ccctgcaaaa acatctccag aaaatgcaac tcaattacaa aggacacaga    660
gaccccagga ccaaggtcca tacaaatgcc ttgaaaattg tgatctcatt ccttttattc    720
tatgctagtt tctttctatg tgttctcata tcatggattt ctgagctgta tcagagcaca    780
```

```
gtgatctaca tgctttgtga gacgattgga gtcttctctc cttcaagcca ctcctttctt    840
ctgattctag aaacgctaa gttaagacag gcctttcttt tggtggcagc taaggtatgg     900
gctaaacgat ga                                                         912
```

<210> SEQ ID NO 20
<211> LENGTH: 303
<212> TYPE: PRT
<213> ORGANISM: Homo sapiens

<400> SEQUENCE: 20

```
Met Glu Ser Ala Leu Pro Ser Ile Phe Thr Leu Val Ile Leu Ala Glu
 1               5                  10                  15

Phe Ile Ile Gly Asn Leu Ser Asn Gly Phe Ile Val Leu Ile Asn Cys
            20                  25                  30

Ile Asp Trp Val Ser Lys Arg Glu Leu Ser Ser Val Asp Lys Leu Leu
        35                  40                  45

Ile Ile Leu Ala Ile Ser Arg Ile Gly Leu Ile Trp Glu Ile Leu Val
    50                  55                  60

Ser Trp Phe Leu Ala Leu His Tyr Leu Ala Ile Phe Val Ser Gly Thr
65                  70                  75                  80

Gly Leu Arg Ile Met Ile Phe Ser Trp Ile Val Ser Asn His Phe Asn
                85                  90                  95

Leu Trp Leu Ala Thr Ile Phe Ser Ile Phe Tyr Leu Leu Lys Ile Ala
           100                 105                 110

Ser Phe Ser Ser Pro Ala Phe Leu Tyr Leu Lys Trp Arg Val Asn Lys
       115                 120                 125

Val Ile Leu Met Ile Leu Leu Gly Thr Leu Val Phe Leu Phe Leu Asn
   130                 135                 140

Leu Ile Gln Ile Asn Met His Ile Lys Asp Trp Leu Asp Arg Tyr Glu
145                 150                 155                 160

Arg Asn Thr Thr Trp Asn Phe Ser Met Ser Asp Phe Glu Thr Phe Ser
                165                 170                 175

Val Ser Val Lys Phe Thr Met Thr Met Phe Ser Leu Thr Pro Phe Thr
           180                 185                 190

Val Ala Phe Ile Ser Phe Leu Leu Leu Ile Phe Ser Leu Gln Lys His
       195                 200                 205

Leu Gln Lys Met Gln Leu Asn Tyr Lys Gly His Arg Asp Pro Arg Thr
   210                 215                 220

Lys Val His Thr Asn Ala Leu Lys Ile Val Ile Ser Phe Leu Leu Phe
225                 230                 235                 240

Tyr Ala Ser Phe Phe Leu Cys Val Leu Ile Ser Trp Ile Ser Glu Leu
                245                 250                 255

Tyr Gln Ser Thr Val Ile Tyr Met Leu Cys Glu Thr Ile Gly Val Phe
           260                 265                 270

Ser Pro Ser Ser His Ser Phe Leu Leu Ile Leu Gly Asn Ala Lys Leu
       275                 280                 285

Arg Gln Ala Phe Leu Leu Val Ala Ala Lys Val Trp Ala Lys Arg
   290                 295                 300
```

<210> SEQ ID NO 21
<211> LENGTH: 954
<212> TYPE: DNA
<213> ORGANISM: Homo sapiens

<400> SEQUENCE: 21

```
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg tttttcccag ctttatttgc cactgaaaaa     240
atgttcagaa tgcttactaa tatctggaca gtgatcaatc attttagtgt ctggttagct     300
acaggcctcg gtactttta ttttctcaag atagccaatt tttctaactc tattttctc      360
tacctaaagt ggagagttaa aaaggtggtt ttggtgctgc ttcttgtgac ttcggtcttc     420
ttgttttta atattgcact gataaacatc catataaatg ccagtatcaa tggatacaga     480
agaaacaaga cttgcagttc tgattcaagt aactttacac gattttccag tcttattgta     540
ttaaccagca ctgtgttcat tttcataccc tttactttgt ccctggcaat gtttcttctc     600
ctcatcttct ccatgtggaa acatcgcaag aagatgcagc acactgtcaa aatatccgga     660
gacgccagca ccaaagccca cagaggagtt aaaagtgtga tcactttctt cctactctat     720
gccatttttct ctctgtcttt tttcatatca gtttggacct ctgaaaggtt ggaggaaaat     780
ctaattattc tttcccaggt gatgggaatg cttatccttc atgtcactc atgtgttctg     840
attcttggaa acaagaagct gagacaggcc tctctgtcag tgctactgtg gctgaggtac     900
atgttcaaag atggggagcc ctcaggtcac aaagaattta gagaatcatc ttga           954
```

<210> SEQ ID NO 22
<211> LENGTH: 317
<212> TYPE: PRT
<213> ORGANISM: Homo sapiens
<400> SEQUENCE: 22

```
Met Gly Gly Val Ile Lys Ser Ile Phe Thr Phe Val Leu Ile Val Glu
  1               5                  10                  15

Phe Ile Ile Gly Asn Leu Gly Asn Ser Phe Ile Ala Leu Val Asn Cys
                 20                  25                  30

Ile Asp Trp Val Lys Gly Arg Lys Ile Ser Ser Val Asp Arg Ile Leu
             35                  40                  45

Thr Ala Leu Ala Ile Ser Arg Ile Ser Leu Val Trp Leu Ile Phe Gly
         50                  55                  60

Ser Trp Cys Val Ser Val Phe Phe Pro Ala Leu Phe Ala Thr Glu Lys
 65                  70                  75                  80

Met Phe Arg Met Leu Thr Asn Ile Trp Thr Val Ile Asn His Phe Ser
                 85                  90                  95

Val Trp Leu Ala Thr Gly Leu Gly Thr Phe Tyr Phe Leu Lys Ile Ala
                100                 105                 110

Asn Phe Ser Asn Ser Ile Phe Leu Tyr Leu Lys Trp Arg Val Lys Lys
            115                 120                 125

Val Val Leu Val Leu Leu Val Thr Ser Val Phe Leu Phe Leu Asn
        130                 135                 140

Ile Ala Leu Ile Asn Ile His Ile Asn Ala Ser Ile Asn Gly Tyr Arg
145                 150                 155                 160

Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
            180                 185                 190

Leu Ser Leu Ala Met Phe Leu Leu Leu Ile Phe Ser Met Trp Lys His
        195                 200                 205
```

Arg Lys Lys Met Gln His Thr Val Lys Ile Ser Gly Asp Ala Ser Thr
210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
                260                 265                 270

Pro Ser Cys His Ser Cys Val Leu Ile Leu Gly Asn Lys Lys Leu Arg
            275                 280                 285

Gln Ala Ser Leu Ser Val Leu Leu Trp Leu Arg Tyr Met Phe Lys Asp
290                 295                 300

Gly Glu Pro Ser Gly His Lys Glu Phe Arg Glu Ser Ser
305                 310                 315

<210> SEQ ID NO 23
<211> LENGTH: 876
<212> TYPE: DNA
<213> ORGANISM: Homo sapiens

<400> SEQUENCE: 23

```
atgataccca tccaactcac tgtcttcttc atgatcatct atgtgcttga gtccttgaca      60
attattgtgc agagcagcct aattgttgca gtgctgggca gagaatggct gcaagtcaga    120
aggctgatgc ctgtggacat gattctcatc agcctgggca tctctcgctt ctgtctacag    180
tgggcatcaa tgctgaacaa ttttttgctcc tattttaatt tgaattatgt actttgcaac    240
ttaacaatca cctgggaatt ttttaatatc cttacattct ggttaaacag cttgcttacc    300
gtgttctact gcatcaaggt ctcttctttc acccatcaca tctttctctg gctgaggtgg    360
agaattttga ggttgtttcc ctggatatta ctgggttctc tgatgattac ttgtgtaaca    420
atcatccctt cagctattgg gaattacatt caaattcagt tactcaccat ggagcatcta    480
ccaagaaaca gcactgtaac tgacaaactt gaaaattttc atcagtatca gttccaggct    540
catacagttg cattggttat tcctttcatc ctgttcctgg cctccaccat ctttctcatg    600
gcatcactga ccaagcagat acaacatcat agcactggtc actgcaatcc aagcatgaaa    660
gcgcacttca ctgccctgag gtcccttgcc gtcttattta ttgtgtttac ctcttacttt    720
ctaaccatac tcatccaccat tataggtact ctatttgata gagatgttg gttatgggtc    780
tgggaagctt tgtctatgc tttcatctta atgcattcca cttcactgat gctgagcagc    840
cctacgttga aaaggattct aaagggaaag tgctag                               876
```

<210> SEQ ID NO 24
<211> LENGTH: 291
<212> TYPE: PRT
<213> ORGANISM: Homo sapiens

<400> SEQUENCE: 24

Met Ile Pro Ile Gln Leu Thr Val Phe Phe Met Ile Ile Tyr Val Leu
1               5                   10                  15

Glu Ser Leu Thr Ile Ile Val Gln Ser Ser Leu Ile Val Ala Val Leu
                20                  25                  30

Gly Arg Glu Trp Leu Gln Val Arg Arg Leu Met Pro Val Asp Met Ile
            35                  40                  45

Leu Ile Ser Leu Gly Ile Ser Arg Phe Cys Leu Gln Trp Ala Ser Met
        50                  55                  60

```
Leu Asn Asn Phe Cys Ser Tyr Phe Asn Leu Asn Tyr Val Leu Cys Asn
 65                  70                  75                  80

Leu Thr Ile Thr Trp Glu Phe Phe Asn Ile Leu Thr Phe Trp Leu Asn
                 85                  90                  95

Ser Leu Leu Thr Val Phe Tyr Cys Ile Lys Val Ser Ser Phe Thr His
            100                 105                 110

His Ile Phe Leu Trp Leu Arg Trp Ile Leu Arg Leu Phe Pro Trp
        115                 120                 125

Ile Leu Leu Gly Ser Leu Met Ile Thr Cys Val Thr Ile Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala His Phe Thr
    210                 215                 220

Ala Leu Arg Ser Leu Ala Val Leu Phe Ile Val Phe Thr Ser Tyr Phe
225                 230                 235                 240

Leu Thr Ile Leu Ile Thr Ile Gly Thr Leu Phe Asp Lys Arg Cys
                245                 250                 255

Trp Leu Trp Val Trp Glu Ala Phe Val Tyr Ala Phe Ile Leu Met His
            260                 265                 270

Ser Thr Ser Leu Met Leu Ser Ser Pro Thr Leu Lys Arg Ile Leu Lys
        275                 280                 285

Gly Lys Cys
    290

<210> SEQ ID NO 25
<211> LENGTH: 960
<212> TYPE: DNA
<213> ORGANISM: Homo sapiens

<400> SEQUENCE: 25
atgataactt ttctgcccat cattttttcc attctaatag tggttatatt tgtgattgga      60
aattttgcta atggcttcat agcattggta aattccattg agtgggtcaa gagacaaaag     120
atctcctttg ttgaccaaat tctcactgct ctggcggtct ccagagttgg tttgctctgg     180
gtgttattac tacattggta tgcaactcag ttgaatccag cttttttatag tgtagaagta     240 agaattactg cttataatgt ctgggcagta accaaccatt tcagcagctg gcttgctact     300
agcctcagca tgttttattt gctcaggatt gccaatttct ccaaccttat tttctcttcgc     360 ataaagagga gagttaagag tgttgttctg gtgatactgt tggggccttt gctattttg      420 gtttgtcatc tttttgtgat aaacatggat gagactgtat ggacaaaaga atatgaagga     480
aacgtgactt ggaagatcaa attgaggagt gcaatgtacc attcaaatat gactctaacc     540
atgctagcaa actttgtacc cctcactctg accctgatat cttttctgct gttaatctgt     600
tctctgtgta acatctcaa gaagatgcaa ctccatggca aaggatctca agatcccagc      660
accaaggtcc acataaaagc tttgcaaact gtgacctcct tcttctgtt atgtgccatt      720 tactttctgt ccatgatcat atcagtttgt aatttgggga ggctggaaaa gcaacctgtc     780
```

```
ttcatgttct gccaagctat tatattcagc tatccttcaa cccacccatt catcctgatt      840
ttgggaaaca agaagctaaa gcagattttt ctttcagttt tgcggcatgt gaggtactgg      900
gtgaaagaca gaagccttcg tctccataga ttcacaagag gggcattgtg tgtcttctag      960
```

<210> SEQ ID NO 26
<211> LENGTH: 319
<212> TYPE: PRT
<213> ORGANISM: Homo sapiens
<400> SEQUENCE: 26

| Met | Ile | Thr | Phe | Leu | Pro | Ile | Ile | Phe | Ser | Ile | Leu | Ile | Val | Val | Ile |
|---|---|---|---|---|---|---|---|---|---|---|---|---|---|---|---|
| 1 | | | | 5 | | | | | 10 | | | | | 15 | |

| Phe | Val | Ile | Gly | Asn | Phe | Ala | Asn | Gly | Phe | Ile | Ala | Leu | Val | Asn | Ser |
|---|---|---|---|---|---|---|---|---|---|---|---|---|---|---|---|
| | | | 20 | | | | | 25 | | | | | 30 | | |

| Ile | Glu | Trp | Val | Lys | Arg | Gln | Lys | Ile | Ser | Phe | Val | Asp | Gln | Ile | Leu |
|---|---|---|---|---|---|---|---|---|---|---|---|---|---|---|---|
| | | | 35 | | | | | 40 | | | | | 45 | | |

| Thr | Ala | Leu | Ala | Val | Ser | Arg | Val | Gly | Leu | Leu | Trp | Val | Leu | Leu | Leu |
|---|---|---|---|---|---|---|---|---|---|---|---|---|---|---|---|
| | 50 | | | | | 55 | | | | | 60 | | | | |

| His | Trp | Tyr | Ala | Thr | Gln | Leu | Asn | Pro | Ala | Phe | Tyr | Ser | Val | Glu | Val |
|---|---|---|---|---|---|---|---|---|---|---|---|---|---|---|---|
| 65 | | | | | 70 | | | | | 75 | | | | | 80 |

| Arg | Ile | Thr | Ala | Tyr | Asn | Val | Trp | Ala | Val | Thr | Asn | His | Phe | Ser | Ser |
|---|---|---|---|---|---|---|---|---|---|---|---|---|---|---|---|
| | | | | 85 | | | | | 90 | | | | | 95 | |

| Trp | Leu | Ala | Thr | Ser | Leu | Ser | Met | Phe | Tyr | Leu | Leu | Arg | Ile | Ala | Asn |
|---|---|---|---|---|---|---|---|---|---|---|---|---|---|---|---|
| | | | 100 | | | | | 105 | | | | | 110 | | |

| Phe | Ser | Asn | Leu | Ile | Phe | Leu | Arg | Ile | Lys | Arg | Arg | Val | Lys | Ser | Val |
|---|---|---|---|---|---|---|---|---|---|---|---|---|---|---|---|
| | | 115 | | | | | 120 | | | | | 125 | | | |

| Val | Leu | Val | Ile | Leu | Leu | Gly | Pro | Leu | Leu | Phe | Leu | Val | Cys | His | Leu |
|---|---|---|---|---|---|---|---|---|---|---|---|---|---|---|---|
| 130 | | | | | 135 | | | | | 140 | | | | | |

| Phe | Val | Ile | Asn | Met | Asp | Glu | Thr | Val | Trp | Thr | Lys | Glu | Tyr | Glu | Gly |
|---|---|---|---|---|---|---|---|---|---|---|---|---|---|---|---|
| 145 | | | | | 150 | | | | | 155 | | | | | 160 |

| Asn | Val | Thr | Trp | Lys | Ile | Lys | Leu | Arg | Ser | Ala | Met | Tyr | His | Ser | Asn |
|---|---|---|---|---|---|---|---|---|---|---|---|---|---|---|---|
| | | | 165 | | | | | 170 | | | | | 175 | | |

| Met | Thr | Leu | Thr | Met | Leu | Ala | Asn | Phe | Val | Pro | Leu | Thr | Leu | Thr | Leu |
|---|---|---|---|---|---|---|---|---|---|---|---|---|---|---|---|
| | | | 180 | | | | | 185 | | | | | 190 | | |

| Ile | Ser | Phe | Leu | Leu | Leu | Ile | Cys | Ser | Leu | Cys | Lys | His | Leu | Lys | Lys |
|---|---|---|---|---|---|---|---|---|---|---|---|---|---|---|---|
| | | 195 | | | | | 200 | | | | | 205 | | | |

| Met | Gln | Leu | His | Gly | Lys | Gly | Ser | Gln | Asp | Pro | Ser | Thr | Lys | Val | His |
|---|---|---|---|---|---|---|---|---|---|---|---|---|---|---|---|
| | 210 | | | | | 215 | | | | | 220 | | | | |

| Ile | Lys | Ala | Leu | Gln | Thr | Val | Thr | Ser | Phe | Leu | Leu | Leu | Cys | Ala | Ile |
|---|---|---|---|---|---|---|---|---|---|---|---|---|---|---|---|
| 225 | | | | | 230 | | | | | 235 | | | | | 240 |

| Tyr | Phe | Leu | Ser | Met | Ile | Ile | Ser | Val | Cys | Asn | Leu | Gly | Arg | Leu | Glu |
|---|---|---|---|---|---|---|---|---|---|---|---|---|---|---|---|
| | | | | 245 | | | | | 250 | | | | | 255 | |

| Lys | Gln | Pro | Val | Phe | Met | Phe | Cys | Gln | Ala | Ile | Ile | Phe | Ser | Tyr | Pro |
|---|---|---|---|---|---|---|---|---|---|---|---|---|---|---|---|
| | | | 260 | | | | | 265 | | | | | 270 | | |

| Ser | Thr | His | Pro | Phe | Ile | Leu | Ile | Leu | Gly | Asn | Lys | Lys | Leu | Lys | Gln |
|---|---|---|---|---|---|---|---|---|---|---|---|---|---|---|---|
| | | 275 | | | | | 280 | | | | | 285 | | | |

| Ile | Phe | Leu | Ser | Val | Leu | Arg | His | Val | Arg | Tyr | Trp | Val | Lys | Asp | Arg |
|---|---|---|---|---|---|---|---|---|---|---|---|---|---|---|---|
| | 290 | | | | | 295 | | | | | 300 | | | | |

| Ser | Leu | Arg | Leu | His | Arg | Phe | Thr | Arg | Gly | Ala | Leu | Cys | Val | Phe |
|---|---|---|---|---|---|---|---|---|---|---|---|---|---|---|
| 305 | | | | | 310 | | | | | 315 | | | | |

<210> SEQ ID NO 27
<211> LENGTH: 900
<212> TYPE: DNA
<213> ORGANISM: Homo sapiens

<400> SEQUENCE: 27

```
atgataactt ttctgcccat catattttcc attctagtag tggttacatt tgttattgga      60
aattttgcta atggcttcat agcgttggtg aattccaccg agtgggtgaa gagacaaaag     120
atctcctttg ctgaccaaat tgtcactgct ctggcggtct ccagagttgg tttgctctgg     180
gtgttattat taaattggta ttcaactgtg ttgaatccag cttttttatag tgtagagtta    240
agaactactg cttataatat ctgggcagta accggccatt tcagcaactg gcctgctact     300
agcctcagca tattttattt gctcaagatt gccaatttct ccaaccttat ttttcttcgc     360
ttaaagagga gagttaagag tgtcattctg gtggtgctgt tggggccttt gctatttttg     420
gcttgtcatc tttttgtggt aaacatgaat cagattgtat ggacaaaaga atatgaagga     480
aacatgactt ggaagatcaa attgaggcgt gcaatgtacc tttcagatac gactgtaacc     540
atgctagcaa acttagtacc ctttactgta accctgatat cttttctgct gttagtctgt     600
tctctgtgta acatctcaa gaagatgcag ctccatggca aaggatctca agatcccagt      660
accaaggtcc acataaaagt tttgcaaact gtgatctcct tcttcttgtt atgtgccatt     720
tactttgtgt ctgtaataat atcagtttgg agttttaaga atctggaaaa caaacctgtc     780
ttcatgttct gccaagctat tggattcagc tgttcttcag cccacccgtt catcctgatt     840
tggggaaaca agaagctaaa gcagacttat ctttcagttt tgtggcaaat gaggtactga     900
```

<210> SEQ ID NO 28
<211> LENGTH: 299
<212> TYPE: PRT
<213> ORGANISM: Homo sapiens

<400> SEQUENCE: 28

```
Met Ile Thr Phe Leu Pro Ile Ile Phe Ser Ile Leu Val Val Val Thr
  1               5                  10                  15

Phe Val Ile Gly Asn Phe Ala Asn Gly Phe Ile Ala Leu Val Asn Ser
                 20                  25                  30

Thr Glu Trp Val Lys Arg Gln Lys Ile Ser Phe Ala Asp Gln Ile Val
             35                  40                  45

Thr Ala Leu Ala Val Ser Arg Val Gly Leu Leu Trp Val Leu Leu Leu
         50                  55                  60

Asn Trp Tyr Ser Thr Val Leu Asn Pro Ala Phe Tyr Ser Val Glu Leu
 65                  70                  75                  80

Arg Thr Thr Ala Tyr Asn Ile Trp Ala Val Thr Gly His Phe Ser Asn
                 85                  90                  95

Trp Pro Ala Thr Ser Leu Ser Ile Phe Tyr Leu Leu Lys Ile Ala Asn
                100                 105                 110

Phe Ser Asn Leu Ile Phe Leu Arg Leu Lys Arg Val Lys Ser Val
            115                 120                 125

Ile Leu Val Val Leu Leu Gly Pro Leu Leu Phe Leu Ala Cys His Leu
        130                 135                 140

Phe Val Val Asn Met Asn Gln Ile Val Trp Thr Lys Glu Tyr Glu Gly
145                 150                 155                 160

Asn Met Thr Trp Lys Ile Lys Leu Arg Arg Ala Met Tyr Leu Ser Asp
                165                 170                 175

Thr Thr Val Thr Met Leu Ala Asn Leu Val Pro Phe Thr Val Thr Leu
            180                 185                 190

Ile Ser Phe Leu Leu Leu Val Cys Ser Leu Cys Lys His Leu Lys Lys
        195                 200                 205
```

```
Met Gln Leu His Gly Lys Gly Ser Gln Asp Pro Ser Thr Lys Val His
    210                 215                 220
Ile Lys Val Leu Gln Thr Val Ile Ser Phe Phe Leu Leu Cys Ala Ile
225                 230                 235                 240
Tyr Phe Val Ser Val Ile Ile Ser Val Trp Ser Phe Lys Asn Leu Glu
                245                 250                 255
Asn Lys Pro Val Phe Met Phe Cys Gln Ala Ile Gly Phe Ser Cys Ser
            260                 265                 270
Ser Ala His Pro Phe Ile Leu Ile Trp Gly Asn Lys Lys Leu Lys Gln
        275                 280                 285
Thr Tyr Leu Ser Val Leu Trp Gln Met Arg Tyr
        290                 295
```

<210> SEQ ID NO 29
<211> LENGTH: 1002
<212> TYPE: DNA
<213> ORGANISM: Homo sapiens

<400> SEQUENCE: 29

```
atgttgactc taactcgcat ccgcactgtg tcctatgaag tcaggagtac atttctgttc    60
atttcagtcc tggagtttgc agtggggttt ctgaccaatg ccttcgtttt cttggtgaat   120
ttttgggatg tagtgaagag gcagccactg agcaacagtg attgtgtgct gctgtgtctc   180
agcatcagcc ggcttttcct gcatggactg ctgttcctga gtgctatcca gcttacccac   240
ttccagaagt tgagtgaacc actgaaccac agctaccaag ccatcatcat gctatggatg   300
attgcaaacc aagccaacct ctggcttgct gcctgcctca gcctgcttta ctgctccaag   360
ctcatccgtt tctctcacac cttcctgatc tgcttggcaa gctgggtctc aggaagatc   420
tcccagatgc tcctgggtat tattctttgc tcctgcatct gcactgtcct ctgtgtttgg   480
tgctttttta gcagacctca cttcacagtc acaactgtgc tattcatgaa taacaataca   540
aggctcaact ggcagattaa agatctcaat ttatttat cctttctctt ctgctatctg   600
tggtctgtgc ctccttcct attgtttctg gtttcttctg ggatgctgac tgtctccctg   660
ggaaggcaca tgaggacaat gaaggtctat accagaaact ctcgtgaccc cagcctggag   720
gcccacatta aagccctcaa gtctcttgtc tccttttct gcttctttgt gatatcatcc   780
tgtgctgcct tcatctctgt gcccctactg attctgtggc gcgacaaaat aggggtgatg   840
gtttgtgttg ggataatggc agcttgtccc tctgggcatg cagccgtcct gatctcaggc   900
aatgccaagt tgaggagagc tgtgatgacc attctgctct gggctcagag cagcctgaag   960
gtaagagccg accacaaggc agattcccgg acactgtgct ga                     1002
```

<210> SEQ ID NO 30
<211> LENGTH: 333
<212> TYPE: PRT
<213> ORGANISM: Homo sapiens

<400> SEQUENCE: 30

```
Met Leu Thr Leu Thr Arg Ile Arg Thr Val Ser Tyr Glu Val Arg Ser
1               5                   10                  15
Thr Phe Leu Phe Ile Ser Val Leu Glu Phe Ala Val Gly Phe Leu Thr
                20                  25                  30
Asn Ala Phe Val Phe Leu Val Asn Phe Trp Asp Val Val Lys Arg Gln
            35                  40                  45
Pro Leu Ser Asn Ser Asp Cys Val Leu Leu Cys Leu Ser Ile Ser Arg
```

```
                    50                  55                  60
Leu Phe Leu His Gly Leu Leu Phe Leu Ser Ala Ile Gln Leu Thr His
 65                  70                  75                  80

Phe Gln Lys Leu Ser Glu Pro Leu Asn His Ser Tyr Gln Ala Ile Ile
                 85                  90                  95

Met Leu Trp Met Ile Ala Asn Gln Ala Asn Leu Trp Leu Ala Ala Cys
             100                 105                 110

Leu Ser Leu Leu Tyr Cys Ser Lys Leu Ile Arg Phe Ser His Thr Phe
         115                 120                 125

Leu Ile Cys Leu Ala Ser Trp Val Ser Arg Lys Ile Ser Gln Met Leu
     130                 135                 140

Leu Gly Ile Ile Leu Cys Ser Cys Ile Cys Thr Val Leu Cys Val Trp
145                 150                 155                 160

Cys Phe Phe Ser Arg Pro His Phe Thr Val Thr Val Leu Phe Met
                 165                 170                 175

Asn Asn Asn Thr Arg Leu Asn Trp Gln Ile Lys Asp Leu Asn Leu Phe
             180                 185                 190

Tyr Ser Phe Leu Phe Cys Tyr Leu Trp Ser Val Pro Pro Phe Leu Leu
         195                 200                 205

Phe Leu Val Ser Ser Gly Met Leu Thr Val Ser Leu Gly Arg His Met
     210                 215                 220

Arg Thr Met Lys Val Tyr Thr Arg Asn Ser Arg Asp Pro Ser Leu Glu
225                 230                 235                 240

Ala His Ile Lys Ala Leu Lys Ser Leu Val Ser Phe Phe Cys Phe Phe
                 245                 250                 255

Val Ile Ser Ser Cys Ala Ala Phe Ile Ser Val Pro Leu Leu Ile Leu
             260                 265                 270

Trp Arg Asp Lys Ile Gly Val Met Val Cys Val Gly Ile Met Ala Ala
         275                 280                 285

Cys Pro Ser Gly His Ala Ala Val Leu Ile Ser Gly Asn Ala Lys Leu
     290                 295                 300

Arg Arg Ala Val Met Thr Ile Leu Leu Trp Ala Gln Ser Ser Leu Lys
305                 310                 315                 320

Val Arg Ala Asp His Lys Ala Asp Ser Arg Thr Leu Cys
                 325                 330

<210> SEQ ID NO 31
<211> LENGTH: 966
<212> TYPE: DNA
<213> ORGANISM: Homo sapiens

<400> SEQUENCE: 31
atgactaaac tctgcgatcc tgcagaaagt gaattgtcgc catttctcat caccttaatt      60
ttagcagttt tacttgctga atacctcatt ggtatcattg caaatggttt catcatggct     120
atacatgcag ctgaatgggt tcaaaataag gcagtttcca caagtggcag gatcctggtt     180
ttcctgagtg tatccagaat agctctccaa agcctcatga tgttagaaat taccatcagc     240
tcaacctccc taagttttta ttctgaagac gctgtatatt atgcattcaa aataagtttt     300
atattcttaa attttgtag cctgtggttt gctgcctggc tcagtttctt ctactttgtg     360
aagattgcca atttctccta ccccctttc ctcaaactga ggtggagaat tactggattg     420
ataccctggc ttctgtggct gtccgtgttt atttccttca gtcacagcat gttctgcatc     480
aacatctgca ctgtgtattg taacaattct ttccctatcc actcctccaa ctccactaag     540
```

-continued

```
aaaacatact tgtctgagat caatgtggtc ggtctggctt ttttcttttaa cctggggatt    600 gtgactcctc tgatcatgtt catcctgaca gccaccctgc tgatcctctc tctcaagaga    660
cacaccctac acatgggaag caatgccaca gggtccaacg accccagcat ggaggctcac    720 atggggggcca tcaaagctat cagctacttt ctcattctct acattttcaa tgcagttgct    780
ctgtttatct acctgtccaa catgtttgac atcaacagtc tgtggaataa tttgtgccag    840
atcatcatgg ctgcctaccc tgccagccac tcaattctac tgattcaaga taaccctggg    900
ctgagaagag cctggaagcg gcttcagctt cgacttcatc tttacccaaa agagtggact    960
ctgtga                                                               966
```

<210> SEQ ID NO 32
<211> LENGTH: 321
<212> TYPE: PRT
<213> ORGANISM: Homo sapiens

<400> SEQUENCE: 32

```
Met Thr Lys Leu Cys Asp Pro Ala Glu Ser Glu Leu Ser Pro Phe Leu
 1               5                  10                  15

Ile Thr Leu Ile Leu Ala Val Leu Leu Ala Glu Tyr Leu Ile Gly Ile
            20                  25                  30

Ile Ala Asn Gly Phe Ile Met Ala Ile His Ala Ala Glu Trp Val Gln
        35                  40                  45

Asn Lys Ala Val Ser Thr Ser Gly Arg Ile Leu Val Phe Leu Ser Val
    50                  55                  60

Ser Arg Ile Ala Leu Gln Ser Leu Met Met Leu Glu Ile Thr Ile Ser
65                  70                  75                  80

Ser Thr Ser Leu Ser Phe Tyr Ser Glu Asp Ala Val Tyr Tyr Ala Phe
                85                  90                  95

Lys Ile Ser Phe Ile Phe Leu Asn Phe Cys Ser Leu Trp Phe Ala Ala
           100                 105                 110

Trp Leu Ser Phe Phe Tyr Phe Val Lys Ile Ala Asn Phe Ser Tyr Pro
       115                 120                 125

Leu Phe Leu Lys Leu Arg Trp Arg Ile Thr Gly Leu Ile Pro Trp Leu
   130                 135                 140

Leu Trp Leu Ser Val Phe Ile Ser Phe Ser His Ser Met Phe Cys Ile
145                 150                 155                 160

Asn Ile Cys Thr Val Tyr Cys Asn Asn Ser Phe Pro Ile His Ser Ser
                165                 170                 175

Asn Ser Thr Lys Lys Thr Tyr Leu Ser Glu Ile Asn Val Val Gly Leu
           180                 185                 190

Ala Phe Phe Phe Asn Leu Gly Ile Val Thr Pro Leu Ile Met Phe Ile
       195                 200                 205

Leu Thr Ala Thr Leu Leu Ile Leu Ser Leu Lys Arg His Thr Leu His
   210                 215                 220

Met Gly Ser Asn Ala Thr Gly Ser Asn Asp Pro Ser Met Glu Ala His
225                 230                 235                 240

Met Gly Ala Ile Lys Ala Ile Ser Tyr Phe Leu Ile Leu Tyr Ile Phe
                245                 250                 255

Asn Ala Val Ala Leu Phe Ile Tyr Leu Ser Asn Met Phe Asp Ile Asn
           260                 265                 270

Ser Leu Trp Asn Asn Leu Cys Gln Ile Ile Met Ala Ala Tyr Pro Ala
       275                 280                 285

Ser His Ser Ile Leu Leu Ile Gln Asp Asn Pro Gly Leu Arg Arg Ala
```

```
                290               295               300
            Trp Lys Arg Leu Gln Leu Arg Leu His Leu Tyr Pro Lys Glu Trp Thr
            305                 310                 315                 320

Leu

<210> SEQ ID NO 33
<211> LENGTH: 972
<212> TYPE: DNA
<213> ORGANISM: Homo sapiens

<400> SEQUENCE: 33
atggcaacgg tgaacacaga tgccacagat aaagacatat ccaagttcaa ggtcaccttc      60
actttggtgg tctccggaat agagtgcatc actggcatcc ttgggagtgg cttcatcacg     120
gccatctatg gggctgagtg gccaggggc aaaacactcc ccactggtga ccgcattatg      180
ttgatgctga gcttttccag gctcttgcta cagatttgga tgatgctgga gaacattttc     240
agtctgctat tccgaattgt ttataaccaa aactcagtgt atatcctctt caaagtcatc     300
actgtctttc tgaaccattc caatctctgg tttgctgcct ggctcaaagt cttctattgt     360
cttagaattg caaacttcaa tcatcctttg ttcttcctga tgaagaggaa aatcatagtg     420
ctgatgcctt ggcttctcag gctgtcagtg ttggtttcct taagcttcag cttcctctc     480 tcgagagatg tcttcaatgt gtatgtgaat agctccattc ctatccctc ctccaactcc     540 acggagaaga agtacttctc tgagaccaat atggtcaacc tggtattttt ctataacatg     600
gggatcttcg ttcctctgat catgttcatc ctggcagcca ccctgctgat cctctctctc     660
aagagacaca ccctacacat gggaagcaat gccacagggt ccagggaccc cagcatgaag     720
gctcacatag gggccatcaa agccaccagc tactttctca tcctctacat tttcaatgca     780
attgctctat ttcttccac gtccaacatc tttgacactt acagttcctg gaatattttg     840
tgcaagatca tcatggctgc ctaccctgcc ggccactcag tacaactgat cttgggcaac     900
cctgggctga agagcctg gaagcggttt cagcaccaag ttcctcttta cctaaaaggg     960
cagactctgt ga                                                         972

<210> SEQ ID NO 34
<211> LENGTH: 323
<212> TYPE: PRT
<213> ORGANISM: Homo sapiens

<400> SEQUENCE: 34

Met Ala Thr Val Asn Thr Asp Ala Thr Asp Lys Asp Ile Ser Lys Phe
  1               5                  10                  15

Lys Val Thr Phe Thr Leu Val Val Ser Gly Ile Glu Cys Ile Thr Gly
                 20                  25                  30

Ile Leu Gly Ser Gly Phe Ile Thr Ala Ile Tyr Gly Ala Glu Trp Ala
             35                  40                  45

Arg Gly Lys Thr Leu Pro Thr Gly Asp Arg Ile Met Leu Met Leu Ser
         50                  55                  60

Phe Ser Arg Leu Leu Leu Gln Ile Trp Met Met Leu Glu Asn Ile Phe
 65                  70                  75                  80

Ser Leu Leu Phe Arg Ile Val Tyr Asn Gln Asn Ser Val Tyr Ile Leu
                     85                  90                  95

Phe Lys Val Ile Thr Val Phe Leu Asn His Ser Asn Leu Trp Phe Ala
                100                 105                 110

Ala Trp Leu Lys Val Phe Tyr Cys Leu Arg Ile Ala Asn Phe Asn His
```

```
            115                 120                 125
Pro Leu Phe Phe Leu Met Lys Arg Lys Ile Ile Val Leu Met Pro Trp
130                 135                 140

Leu Leu Arg Leu Ser Val Leu Val Ser Leu Ser Phe Ser Phe Pro Leu
145                 150                 155                 160

Ser Arg Asp Val Phe Asn Val Tyr Val Asn Ser Ser Ile Pro Ile Pro
                165                 170                 175

Ser Ser Asn Ser Thr Glu Lys Lys Tyr Phe Ser Glu Thr Asn Met Val
            180                 185                 190

Asn Leu Val Phe Phe Tyr Asn Met Gly Ile Phe Val Pro Leu Ile Met
        195                 200                 205

Phe Ile Leu Ala Ala Thr Leu Leu Ile Leu Ser Leu Lys Arg His Thr
210                 215                 220

Leu His Met Gly Ser Asn Ala Thr Gly Ser Arg Asp Pro Ser Met Lys
225                 230                 235                 240

Ala His Ile Gly Ala Ile Lys Ala Thr Ser Tyr Phe Leu Ile Leu Tyr
                245                 250                 255

Ile Phe Asn Ala Ile Ala Leu Phe Leu Ser Thr Ser Asn Ile Phe Asp
            260                 265                 270

Thr Tyr Ser Ser Trp Asn Ile Leu Cys Lys Ile Ile Met Ala Ala Tyr
        275                 280                 285

Pro Ala Gly His Ser Val Gln Leu Ile Leu Gly Asn Pro Gly Leu Arg
290                 295                 300

Arg Ala Trp Lys Arg Phe Gln His Gln Val Pro Leu Tyr Leu Lys Gly
305                 310                 315                 320

Gln Thr Leu

<210> SEQ ID NO 35
<211> LENGTH: 930
<212> TYPE: DNA
<213> ORGANISM: Homo sapiens

<400> SEQUENCE: 35
atgataactt ttctacccat cattttttcc agtctggtag tggttacatt tgttattgga      60
aattttgcta atggcttcat agcactggta aattccattg agtggttcaa gagacaaaag     120 atctccttttg ctgaccaaat tctcactgct ctggcggtct ccagagttgg tttgctctgg    180
gtattattat taaactggta ttcaactgtg ttgaatccag cttttaatag tgtagaagta    240
agaactactg cttataatat ctgggcagtg atcaaccatt tcagcaactg gcttgctact    300
accctcagca tattttattt gctcaagatt gccaatttct ccaactttat ttttcttcac    360
ttaaagagga gagttaagag tgtcattctg gtgatgttgt tggggccttt gctattttg     420 gcttgtcatc tttttgtgat aaacatgaat gagattgtgc ggacaaaaga atttgaagga    480
aacatgactt ggaagatcaa attgaagagt gcaatgtact tttcaaatat gactgtaacc    540
atggtagcaa acttagtacc cttcactctg accctactat cttttatgct gttaatctgt    600
tctttgtgta acatctcaa gaagatgcag ctccatggta aaggatctca agatcccagc     660
accaaggtcc acataaaagc tttgcaaact gtgatctcct tcctcttgtt atgtgccatt    720
tactttctgt ccataatgat atcagtttgg agttttggaa gtctggaaaa caaacctgtc   780
ttcatgttct gcaaagctat tagattcagc tatccttcaa tccacccatt catcctgatt    840
tggggaaaca agaagctaaa gcagactttt ctttcagttt tttggcaaat gaggtactgg    900
gtgaaaggag agaagacttc atctccatag                                     930
```

<210> SEQ ID NO 36
<211> LENGTH: 309
<212> TYPE: PRT
<213> ORGANISM: Homo sapiens

<400> SEQUENCE: 36

Met Ile Thr Phe Leu Pro Ile Phe Ser Ser Leu Val Val Thr
1               5                   10                  15

Phe Val Ile Gly Asn Phe Ala Asn Gly Phe Ile Ala Leu Val Asn Ser
                20                  25                  30

Ile Glu Trp Phe Lys Arg Gln Lys Ile Ser Phe Ala Asp Gln Ile Leu
            35                  40                  45

Thr Ala Leu Ala Val Ser Arg Val Gly Leu Leu Trp Val Leu Leu Leu
        50                  55                  60

Asn Trp Tyr Ser Thr Val Leu Asn Pro Ala Phe Asn Ser Val Glu Val
65                  70                  75                  80

Arg Thr Thr Ala Tyr Asn Ile Trp Ala Val Ile Asn His Phe Ser Asn
                85                  90                  95

Trp Leu Ala Thr Thr Leu Ser Ile Phe Tyr Leu Leu Lys Ile Ala Asn
                100                 105                 110

Phe Ser Asn Phe Ile Phe Leu His Leu Lys Arg Arg Val Lys Ser Val
            115                 120                 125

Ile Leu Val Met Leu Leu Gly Pro Leu Leu Phe Leu Ala Cys His Leu
        130                 135                 140

Phe Val Ile Asn Met Asn Glu Ile Val Arg Thr Lys Glu Phe Glu Gly
145                 150                 155                 160

Asn Met Thr Trp Lys Ile Lys Leu Lys Ser Ala Met Tyr Phe Ser Asn
                165                 170                 175

Met Thr Val Thr Met Val Ala Asn Leu Val Pro Phe Thr Leu Thr Leu
            180                 185                 190

Leu Ser Phe Met Leu Leu Ile Cys Ser Leu Cys Lys His Leu Lys Lys
        195                 200                 205

Met Gln Leu His Gly Lys Gly Ser Gln Asp Pro Ser Thr Lys Val His
210                 215                 220

Ile Lys Ala Leu Gln Thr Val Ile Ser Phe Leu Leu Leu Cys Ala Ile
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
        275                 280                 285

Thr Phe Leu Ser Val Phe Trp Gln Met Arg Tyr Trp Val Lys Gly Glu
    290                 295                 300

Lys Thr Ser Ser Pro
305

<210> SEQ ID NO 37
<211> LENGTH: 930
<212> TYPE: DNA
<213> ORGANISM: Homo sapiens

<400> SEQUENCE: 37
atgacaactt ttatacccat cattttttcc agtgtggtag tggttctatt tgttattgga      60

```
aattttgcta atggcttcat agcattggta aattccattg agcgggtcaa gagacaaaag      120
atctcttttg ctgaccagat tctcactgct ctggcggtct ccagagttgg tttgctctgg      180
gtattattat taaattggta ttcaactgtg tttaatccag cttttatag tgtagaagta       240 agaactactg cttataatgt ctgggcagta accggccatt tcagcaactg gcttgctact      300
agcctcagca tattttattt gctcaagatt gccaatttct ccaaccttat ttttcttcac      360
ttaaagagga gagttaagag tgtcattctg gtgatgctgt tggggccttt actattttg       420 gcttgtcaac tttttgtgat aaacatgaaa gagattgtac ggacaaaaga atatgaagga      480
aacttgactt ggaagatcaa attgaggagt gcagtgtacc tttcagatgc gactgtaacc      540
acgctaggaa acttagtgcc cttcactctg accctgctat gttttttgct gttaatctgt      600
tctctgtgta acatctcaa gaagatgcag ctccatggta aaggatctca agatcccagc       660
accaaggtcc acataaaagc tttgcaaact gtgatctttt cctcttgtt atgtgccgtt       720 tactttctgt ccataatgat atcagtttgg agttttggga gtctggaaaa caaacctgtc      780
ttcatgttct gcaaagctat tagattcagc tatccttcaa tccacccatt catcctgatt      840
tggggaaaca agaagctaaa gcagactttt ctttcagttt tgcggcaagt gaggtactgg      900
gtgaagggag agaagccttc atctccatag                                       930
```

```
<210> SEQ ID NO 38
<211> LENGTH: 309
<212> TYPE: PRT
<213> ORGANISM: Homo sapiens

<400> SEQUENCE: 38
```

| Met | Thr | Thr | Phe | Ile | Pro | Ile | Ile | Phe | Ser | Ser | Val | Val | Val | Leu |
|---|---|---|---|---|---|---|---|---|---|---|---|---|---|---|
| 1 | | | | 5 | | | | | 10 | | | | | 15 |

| Phe | Val | Ile | Gly | Asn | Phe | Ala | Asn | Gly | Phe | Ile | Ala | Leu | Val | Asn | Ser |
|---|---|---|---|---|---|---|---|---|---|---|---|---|---|---|---|
| | | | 20 | | | | | 25 | | | | | 30 | | |

| Ile | Glu | Trp | Val | Lys | Arg | Gln | Lys | Ile | Ser | Phe | Ala | Asp | Gln | Ile | Leu |
|---|---|---|---|---|---|---|---|---|---|---|---|---|---|---|---|
| | | 35 | | | | | 40 | | | | | 45 | | | |

| Thr | Ala | Leu | Ala | Val | Ser | Arg | Val | Gly | Leu | Leu | Trp | Val | Leu | Leu | Leu |
|---|---|---|---|---|---|---|---|---|---|---|---|---|---|---|---|
| | 50 | | | | | 55 | | | | | 60 | | | | |

| Asn | Trp | Tyr | Ser | Thr | Val | Phe | Asn | Pro | Ala | Phe | Tyr | Ser | Val | Glu | Val |
|---|---|---|---|---|---|---|---|---|---|---|---|---|---|---|---|
| 65 | | | | | 70 | | | | | 75 | | | | | 80 |

| Arg | Thr | Thr | Ala | Tyr | Asn | Val | Trp | Ala | Val | Thr | Gly | His | Phe | Ser | Asn |
|---|---|---|---|---|---|---|---|---|---|---|---|---|---|---|---|
| | | | | 85 | | | | | 90 | | | | | 95 | |

| Trp | Leu | Ala | Thr | Ser | Leu | Ser | Ile | Phe | Tyr | Leu | Leu | Lys | Ile | Ala | Asn |
|---|---|---|---|---|---|---|---|---|---|---|---|---|---|---|---|
| | | | 100 | | | | | 105 | | | | | 110 | | |

| Phe | Ser | Asn | Leu | Ile | Phe | Leu | His | Leu | Lys | Arg | Arg | Val | Lys | Ser | Val |
|---|---|---|---|---|---|---|---|---|---|---|---|---|---|---|---|
| | | 115 | | | | | 120 | | | | | 125 | | | |

| Ile | Leu | Val | Met | Leu | Leu | Gly | Pro | Leu | Leu | Phe | Leu | Ala | Cys | Gln | Leu |
|---|---|---|---|---|---|---|---|---|---|---|---|---|---|---|---|
| | 130 | | | | | 135 | | | | | 140 | | | | |

| Phe | Val | Ile | Asn | Met | Lys | Glu | Ile | Val | Arg | Thr | Lys | Glu | Tyr | Glu | Gly |
|---|---|---|---|---|---|---|---|---|---|---|---|---|---|---|---|
| 145 | | | | | 150 | | | | | 155 | | | | | 160 |

| Asn | Met | Thr | Trp | Lys | Ile | Lys | Leu | Arg | Ser | Ala | Val | Tyr | Leu | Ser | Asp |
|---|---|---|---|---|---|---|---|---|---|---|---|---|---|---|---|
| | | | | 165 | | | | | 170 | | | | | 175 | |

| Ala | Thr | Val | Thr | Thr | Leu | Gly | Asn | Leu | Val | Pro | Phe | Thr | Leu | Thr | Leu |
|---|---|---|---|---|---|---|---|---|---|---|---|---|---|---|---|
| | | | 180 | | | | | 185 | | | | | 190 | | |

| Leu | Cys | Phe | Leu | Leu | Leu | Ile | Cys | Ser | Leu | Cys | Lys | His | Leu | Lys | Lys |
|---|---|---|---|---|---|---|---|---|---|---|---|---|---|---|---|
| | | 195 | | | | | 200 | | | | | 205 | | | |

| Met | Gln | Leu | His | Gly | Lys | Gly | Ser | Gln | Asp | Pro | Ser | Thr | Lys | Val | His |
|---|---|---|---|---|---|---|---|---|---|---|---|---|---|---|---|
| | 210 | | | | | 215 | | | | | 220 | | | | |

Ile Lys Val Leu Gln Thr Val Ile Phe Phe Leu Leu Cys Ala Ile
225                 230                 235                 240

Tyr Phe Leu Ser Ile Met Ile Ser Val Trp Ser Phe Gly Ser Leu Glu
                245                 250                 255

Asn Lys Pro Val Phe Met Phe Cys Lys Ala Ile Arg Phe Ser Tyr Pro
            260                 265                 270

Ser Ile His Pro Phe Ile Leu Ile Trp Gly Asn Lys Lys Leu Lys Gln
            275                 280                 285

Thr Phe Leu Ser Val Leu Arg Gln Val Arg Tyr Trp Val Lys Gly Glu
        290                 295                 300

Lys Pro Ser Ser Pro
305

<210> SEQ ID NO 39
<211> LENGTH: 900
<212> TYPE: DNA
<213> ORGANISM: Homo sapiens

<400> SEQUENCE: 39
atgatgtgtt ttctgctcat catttcatca attctggtag tgtttgcatt tgttcttgga      60
aatgttgcca atggcttcat agccctagta aatgtcattg actgggttaa cacacgaaag     120
atctcctcag ctgagcaaat tctcactgct ctggtggtct ccaggattgg tttactctgg     180
gtcatgttat tcctttggta tgcaactgtg tttaattctg ctttatatgg tttagaagta     240
agaattgttg cttctaatgc ctgggctgta acgaaccatt tcagcatgtg gcttgctgct     300
agcctcagca tattttgttt gctcaagatt gccaatttct ccaaccttat ttctctccac     360
ctaaagaaga gaattaagag tgttgttctg tgatactgt tggggccctt ggtatttctg      420
atttgtaatc ttgctgtgat aaccatggat gagagagtgt ggacaaaaga atatgaagga     480
aatgtgactt ggaagatcaa attgaggaat gcaatacacc tttcaagctt gactgtaact     540
actctagcaa acctcatacc ctttactctg agcctaatat gttttctgct gttaatctgt     600
tctctttgta acatctcaa gaagatgcgg ctccatagca aaggatctca agatcccagc      660
accaaggtcc atataaaagc tttgcaaact gtgacctcct tcctcatgtt atttgccatt     720
tactttctgt gtataatcac atcaacttgg aatcttagga cacagcagag caaacttgta     780
ctcctgcttt gccaaactgt tgcaatcatg tatccttcat ccactcatt catcctgatt      840
atgggaagta ggaagctaaa acagaccttt cttttcagttt tgtggcagat gacacgctga     900

<210> SEQ ID NO 40
<211> LENGTH: 299
<212> TYPE: PRT
<213> ORGANISM: Homo sapiens

<400> SEQUENCE: 40

Met Met Cys Phe Leu Leu Ile Ile Ser Ser Ile Leu Val Val Phe Ala
1               5                   10                  15

Phe Val Leu Gly Asn Val Ala Asn Gly Phe Ile Ala Leu Val Asn Val
                20                  25                  30

Ile Asp Trp Val Asn Thr Arg Lys Ile Ser Ser Ala Glu Gln Ile Leu
            35                  40                  45

Thr Ala Leu Val Val Ser Arg Ile Gly Leu Leu Trp Val Met Leu Phe
        50                  55                  60

Leu Trp Tyr Ala Thr Val Phe Asn Ser Ala Leu Tyr Gly Leu Glu Val
65                  70                  75                  80

```
Arg Ile Val Ala Ser Asn Ala Trp Ala Val Thr Asn His Phe Ser Met
                85                  90                  95

Trp Leu Ala Ala Ser Leu Ser Ile Phe Cys Leu Leu Lys Ile Ala Asn
            100                 105                 110

Phe Ser Asn Leu Ile Ser Leu His Leu Lys Lys Arg Ile Lys Ser Val
        115                 120                 125

Val Leu Val Ile Leu Leu Gly Pro Leu Val Phe Leu Ile Cys Asn Leu
    130                 135                 140

Ala Val Ile Thr Met Asp Glu Arg Val Trp Thr Lys Glu Tyr Glu Gly
145                 150                 155                 160

Asn Val Thr Trp Lys Ile Lys Leu Arg Asn Ala Ile His Leu Ser Ser
                165                 170                 175

Leu Thr Val Thr Thr Leu Ala Asn Leu Ile Pro Phe Thr Leu Ser Leu
            180                 185                 190

Ile Cys Phe Leu Leu Leu Ile Cys Ser Leu Cys Lys His Leu Lys Lys
        195                 200                 205

Met Arg Leu His Ser Lys Gly Ser Gln Asp Pro Ser Thr Lys Val His
    210                 215                 220

Ile Lys Ala Leu Gln Thr Val Thr Ser Phe Leu Met Leu Phe Ala Ile
225                 230                 235                 240

Tyr Phe Leu Cys Ile Ile Thr Ser Thr Trp Asn Leu Arg Thr Gln Gln
                245                 250                 255

Ser Lys Leu Val Leu Leu Cys Gln Thr Val Ala Ile Met Tyr Pro
            260                 265                 270

Ser Phe His Ser Phe Ile Leu Ile Met Gly Ser Arg Lys Leu Lys Gln
        275                 280                 285

Thr Phe Leu Ser Val Leu Trp Gln Met Thr Arg
    290                 295
```

<210> SEQ ID NO 41
<211> LENGTH: 900
<212> TYPE: DNA
<213> ORGANISM: Homo sapiens

<400> SEQUENCE: 41

```
atgataactt ttctatacat ttttttttca attctaataa tggttttatt tgttctcgga      60
aactttgcca atggcttcat agcactggta aatttcattg actgggtgaa gagaaaaaag     120
atctcctcag ctgaccaaat tctcactgct ctggcggtct ccagaattgg tttgctctgg     180
gcattattat taaattggta tttaactgtg ttgaatccag cttttttatag tgtagaatta     240
agaattactt cttataatgc ctgggttgta accaaccatt tcagcatgtg gcttgctgct     300
aacctcagca tatttttattt gctcaagatt gccaatttct ccaaccttct ttttcttcat     360
ttaaagagga gagttaggag tgtcattctg gtgatactgt ggggactttg atatttttg      420
gtttgtcatc ttcttgtggc aaacatggat gagagtatgt gggcagaaga atatgaagga     480
aacatgactg ggaagatgaa attgaggaat acagtacatc tttcatattt gactgtaact     540
accctatgga gcttcatacc ctttactctg tccctgatat cttttctgat gctaatctgt     600
tctctgtgta aacatctcaa gaagatgcag ctccatggag aaggatcgca agatctcagc     660
accaaggtcc acataaaagc tttgcaaact ctgatctcct tcctcttgtt atgtgccatt     720
ttctttctat tcctaatcgt ttcggttttgg agtcctagga ggctgcggaa tgacccggtt     780
gtcatggtta gcaaggctgt tggaaacata tatcttgcat tcgactcatt catcctaatt     840
```
tggagaacca agaagctaaa acacaccttt cttttgattt tgtgtcagat taggtgctga    900

<210> SEQ ID NO 42
<211> LENGTH: 299
<212> TYPE: PRT
<213> ORGANISM: Homo sapiens

<400> SEQUENCE: 42

Met Ile Thr Phe Leu Tyr Ile Phe Phe Ser Ile Leu Ile Met Val Leu
 1               5                  10                  15

Phe Val Leu Gly Asn Phe Ala Asn Gly Phe Ile Ala Leu Val Asn Phe
             20                  25                  30

Ile Asp Trp Val Lys Arg Lys Ile Ser Ser Ala Asp Gln Ile Leu
         35                  40                  45

Thr Ala Leu Ala Val Ser Arg Ile Gly Leu Leu Trp Ala Leu Leu Leu
     50                  55                  60

Asn Trp Tyr Leu Thr Val Leu Asn Pro Ala Phe Tyr Ser Val Glu Leu
 65                  70                  75                  80

Arg Ile Thr Ser Tyr Asn Ala Trp Val Val Thr Asn His Phe Ser Met
                 85                  90                  95

Trp Leu Ala Ala Asn Leu Ser Ile Phe Tyr Leu Leu Lys Ile Ala Asn
            100                 105                 110

Phe Ser Asn Leu Leu Phe Leu His Leu Lys Arg Arg Val Arg Ser Val
        115                 120                 125

Ile Leu Val Ile Leu Leu Gly Thr Leu Ile Phe Leu Val Cys His Leu
    130                 135                 140

Leu Val Ala Asn Met Asp Glu Ser Met Trp Ala Glu Glu Tyr Glu Gly
145                 150                 155                 160

Asn Met Thr Gly Lys Met Lys Leu Arg Asn Thr Val His Leu Ser Tyr
                165                 170                 175

Leu Thr Val Thr Thr Leu Trp Ser Phe Ile Pro Phe Thr Leu Ser Leu
            180                 185                 190

Ile Ser Phe Leu Met Leu Ile Cys Ser Leu Cys Lys His Leu Lys Lys
        195                 200                 205

Met Gln Leu His Gly Glu Gly Ser Gln Asp Leu Ser Thr Lys Val His
    210                 215                 220

Ile Lys Ala Leu Gln Thr Leu Ile Ser Phe Leu Leu Leu Cys Ala Ile
225                 230                 235                 240

Phe Phe Leu Phe Leu Ile Val Ser Val Trp Ser Pro Arg Arg Leu Arg
                245                 250                 255

Asn Asp Pro Val Val Met Val Ser Lys Ala Val Gly Asn Ile Tyr Leu
                260                 265                 270

Ala Phe Asp Ser Phe Ile Leu Ile Trp Arg Thr Lys Leu Lys His
        275                 280                 285

Thr Phe Leu Leu Ile Leu Cys Gln Ile Arg Cys
    290                 295

<210> SEQ ID NO 43
<211> LENGTH: 924
<212> TYPE: DNA
<213> ORGANISM: Homo sapiens

<400> SEQUENCE: 43
atgcaagcag cactgacggc cttcttcgtg ttgctcttta gcctgctgag tcttctgggg    60
attgcagcga atggcttcat tgtgctggtg ctgggcaggg agtggctgcg atatgcagg    120

```
ttgctgccct tggatatgat cctcattagc ttgggtgcct cccgcttctg cctgcagttg    180
gttgggacgg tgcacaactt ctactactct gcccagaagg tcgagtactc tgggggtctc    240
ggccgacagt tcttccatct acactggcac ttcctgaact cagccacctt ctggttttgc    300
agctggctca gtgtcctgtt ctgtgtgaag attgctaaca tcacacactc caccttcctg    360
tggctgaagt ggaggttccc agggtgggtg ccctggctcc tgttgggctc tgtcctgatc    420
tccttcatca taaccctgct gttttttttgg gtgaactacc ctgtatatca agaattttta    480
attagaaaat tttctgggaa catgacctac aagtggaata caaggataga acatactat     540 ttcccatccc tgaaactggt catctggtca attccttttt ctgttttttct ggtctcaatt    600 atgctgttaa ttaattctct gaggaggcat actcagagaa tgcagcacaa cgggcacagc    660
ctgcaggacc ccagcaccca ggctcacacc agagctctga agtccctcat ctccttcctc    720
attctttatg ctctgtcctt tctgtccctg atcattgatg ccgcaaaatt tatctccatg    780
cagaacgact tttactggcc atggcaaatt gcagtctacc tgtgcatatc tgtccatccc    840
ttcatcctca tcttcagcaa cctcaagctt cgaagcgtgt tctcgcagct cctgttgttg    900 gcaagggggct tctgggtggc ctag                                          924
```

<210> SEQ ID NO 44
<211> LENGTH: 307
<212> TYPE: PRT
<213> ORGANISM: Homo sapiens

<400> SEQUENCE: 44

```
Met Gln Ala Ala Leu Thr Ala Phe Phe Val Leu Leu Phe Ser Leu Leu
  1               5                  10                  15

Ser Leu Leu Gly Ile Ala Ala Asn Gly Phe Ile Val Leu Val Leu Gly
             20                  25                  30

Arg Glu Trp Leu Arg Tyr Gly Arg Leu Leu Pro Leu Asp Met Ile Leu
         35                  40                  45

Ile Ser Leu Gly Ala Ser Arg Phe Cys Leu Gln Leu Val Gly Thr Val
     50                  55                  60

His Asn Phe Tyr Tyr Ser Ala Gln Lys Val Glu Tyr Ser Gly Gly Leu
 65                  70                  75                  80

Gly Arg Gln Phe Phe His Leu His Trp His Phe Leu Asn Ser Ala Thr
                 85                  90                  95

Phe Trp Phe Cys Ser Trp Leu Ser Val Leu Phe Cys Val Lys Ile Ala
            100                 105                 110

Asn Ile Thr His Ser Thr Phe Leu Trp Leu Lys Trp Arg Phe Pro Gly
            115                 120                 125

Trp Val Pro Trp Leu Leu Leu Gly Ser Val Leu Ile Ser Phe Ile Ile
        130                 135                 140

Thr Leu Leu Phe Phe Trp Val Asn Tyr Pro Val Tyr Gln Glu Phe Leu
145                 150                 155                 160

Ile Arg Lys Phe Ser Gly Asn Met Thr Tyr Lys Trp Asn Thr Arg Ile
                165                 170                 175

Glu Thr Tyr Tyr Phe Pro Ser Leu Lys Leu Val Ile Trp Ser Ile Pro
            180                 185                 190

Phe Ser Val Phe Leu Val Ser Ile Met Leu Leu Ile Asn Ser Leu Arg
        195                 200                 205

Arg His Thr Gln Arg Met Gln His Asn Gly His Ser Leu Gln Asp Pro
    210                 215                 220

Ser Thr Gln Ala His Thr Arg Ala Leu Lys Ser Leu Ile Ser Phe Leu
```

```
225             230             235             240
Ile Leu Tyr Ala Leu Ser Phe Leu Ser Leu Ile Ile Asp Ala Ala Lys
                245                 250                 255

Phe Ile Ser Met Gln Asn Asp Phe Tyr Trp Pro Trp Gln Ile Ala Val
                260                 265                 270

Tyr Leu Cys Ile Ser Val His Pro Phe Ile Leu Ile Phe Ser Asn Leu
                275                 280                 285

Lys Leu Arg Ser Val Phe Ser Gln Leu Leu Leu Ala Arg Gly Phe
                290                 295                 300

Trp Val Ala
305

<210> SEQ ID NO 45
<211> LENGTH: 930
<212> TYPE: DNA
<213> ORGANISM: Homo sapiens

<400> SEQUENCE: 45
atgataactt ttctgcccat catttttcc  attctaatag tggttacatt tgtgattgga    60
aattttgcta atggcttcat agcattggta aattccattg agtggttcaa gagacaaaag   120 atctctttg  ctgaccaaat tctcactgct ctggcagtct ccagagttgg tttactctgg   180
gtattagtat taaattggta tgcaactgag ttgaatccag cttttaacag tatagaagta   240
agaattactg cttacaatgt ctgggcagta atcaaccatt tcagcaactg gcttgctact   300
agcctcagca tattttattt gctcaagatt gccaatttct ccaaccttat ttttcttcac   360
ttaaagagga gagttaagag tgttgttctg gtgatactat ggggcctttt gctattttg    420 gtttgtcatc ttttgtgat  aaacatgaat cagattatat ggacaaaaga atatgaagga   480
aacatgactt ggaagatcaa actgaggagt gcaatgtacc tttcaaatac aacggtaacc   540
atcctagcaa acttagttcc cttcactctg accctgatat cttttctgct gttaatctgt   600
tctctgtgta acatctcaa  aaagatgcag ctccatggca aaggatctca agatcccagc   660
atgaaggtcc acataaaagc tttgcaaact gtgacctcct tcctcttgtt atgtgccatt   720
tactttctgt ccataatcat gtcagtttgg agttttgaga gtctgaaaaa caaacctgtc   780
ttcatgttct gcgaagctat tgcattcagc tatccttcaa cccacccatt catcctgatt   840
tggggaaaca gaagctaaa  gcagactttt ctttcagttt tgtggcatgt gaggtactgg   900
gtgaaaggag agaagccttc atcttcatag                                    930

<210> SEQ ID NO 46
<211> LENGTH: 309
<212> TYPE: PRT
<213> ORGANISM: Homo sapiens

<400> SEQUENCE: 46

Met Ile Thr Phe Leu Pro Ile Ile Phe Ser Ile Leu Ile Val Val Thr
1               5                   10                  15

Phe Val Ile Gly Asn Phe Ala Asn Gly Phe Ile Ala Leu Val Asn Ser
                20                  25                  30

Ile Glu Trp Phe Lys Arg Gln Lys Ile Ser Phe Ala Asp Gln Ile Leu
                35                  40                  45

Thr Ala Leu Ala Val Ser Arg Val Gly Leu Leu Trp Val Leu Val Leu
        50                  55                  60

Asn Trp Tyr Ala Thr Glu Leu Asn Pro Ala Phe Asn Ser Ile Glu Val
65              70                  75                  80
```

-continued

```
Arg Ile Thr Ala Tyr Asn Val Trp Ala Val Ile Asn His Phe Ser Asn
                85                  90                  95

Trp Leu Ala Thr Ser Leu Ser Ile Phe Tyr Leu Leu Lys Ile Ala Asn
            100                 105                 110

Phe Ser Asn Leu Ile Phe Leu His Leu Lys Arg Arg Val Lys Ser Val
        115                 120                 125

Val Leu Val Ile Leu Leu Gly Pro Leu Leu Phe Leu Val Cys His Leu
    130                 135                 140

Phe Val Ile Asn Met Asn Gln Ile Ile Trp Thr Lys Glu Tyr Glu Gly
145                 150                 155                 160

Asn Met Thr Trp Lys Ile Lys Leu Arg Ser Ala Met Tyr Leu Ser Asn
                165                 170                 175

Thr Thr Val Thr Ile Leu Ala Asn Leu Val Pro Phe Thr Leu Thr Leu
            180                 185                 190

Ile Ser Phe Leu Leu Leu Ile Cys Ser Leu Cys Lys His Leu Lys Lys
        195                 200                 205

Met Gln Leu His Gly Lys Gly Ser Gln Asp Pro Ser Met Lys Val His
    210                 215                 220

Ile Lys Ala Leu Gln Thr Val Thr Ser Phe Leu Leu Cys Ala Ile
225                 230                 235                 240

Tyr Phe Leu Ser Ile Ile Met Ser Val Trp Ser Phe Glu Ser Leu Glu
                245                 250                 255

Asn Lys Pro Val Phe Met Phe Cys Glu Ala Ile Ala Phe Ser Tyr Pro
            260                 265                 270

Ser Thr His Pro Phe Ile Leu Ile Trp Gly Asn Lys Lys Leu Lys Gln
        275                 280                 285

Thr Phe Leu Ser Val Leu Trp His Val Arg Tyr Trp Val Lys Gly Glu
    290                 295                 300

Lys Pro Ser Ser Ser
305
```

<210> SEQ ID NO 47
<211> LENGTH: 957
<212> TYPE: DNA
<213> ORGANISM: Homo sapiens

<400> SEQUENCE: 47

```
atgaatggag accacatggt tctaggatct tcggtgactg acaagaaggc catcatcttg    60
gttaccattt tactccttt  acgcctggta gcaatagcag caatggctt  catcactgct   120
gctctgggcg tggagtgggt gctacggaga atgttgttgc cttgtgataa gttattggtt   180
agcctagggg cctctcgctt ctgtctgcag tcagtggtaa tgggtaagac catttatgtt   240
ttcttgcatc cgatggcctt cccatacaac cctgtactgc agtttctagc tttccagtgg   300
gacttcctga tgctgccac  cttatggtcc tctacctggc tcagtgtctt ctattgtgtg   360
aaaattgcta ccttcaccca ccctgtcttc ttctggctaa agcacaagtt gtctgggtgg   420
ctaccatgga tgctcttcag ctctgtaggg ctctccagct tcaccaccat tctatttttc   480
ataggcaacc acagaatgta tcagaactat ttaaggaacc atctacaacc ttggaatgtc   540
actggcgata gcatacggag ctactgtgag aaattctatc tcttccctct aaaaatgatt   600
acttggacaa tgcccactgc tgtcttttc  atttgcatga ttttgctcat cacatctctg   660
ggaagacaca ggaagaaggc tctccttaca acctcaggat ccgagagcc  cagtgtgcag   720
gcacacataa aggctctgct ggctctcctc tcttttgcca tgctcttcat ctcatatttc   780
```

-continued

```
ctgtcactgg tgttcagtgc tgcaggtatt tttccacctc tggactttaa attctgggtg      840
tgggagtcag tgatttatct gtgtgcagca gttcacccca tcattctgct cttcagcaac      900
tgcaggctga gagctgtgct gaagagtcgc cgttcctcaa ggtgtgggac accttga         957
```

<210> SEQ ID NO 48
<211> LENGTH: 318
<212> TYPE: PRT
<213> ORGANISM: Homo sapiens

<400> SEQUENCE: 48

```
Met Asn Gly Asp His Met Val Leu Gly Ser Ser Val Thr Asp Lys Lys
  1               5                  10                  15

Ala Ile Ile Leu Val Thr Ile Leu Leu Leu Arg Leu Val Ala Ile
             20                  25                  30

Ala Gly Asn Gly Phe Ile Thr Ala Ala Leu Gly Val Glu Trp Val Leu
         35                  40                  45

Arg Arg Met Leu Leu Pro Cys Asp Lys Leu Leu Val Ser Leu Gly Ala
     50                  55                  60

Ser Arg Phe Cys Leu Gln Ser Val Val Met Gly Lys Thr Ile Tyr Val
 65                  70                  75                  80

Phe Leu His Pro Met Ala Phe Pro Tyr Asn Pro Val Leu Gln Phe Leu
                 85                  90                  95

Ala Phe Gln Trp Asp Phe Leu Asn Ala Ala Thr Leu Trp Ser Ser Thr
            100                 105                 110

Trp Leu Ser Val Phe Tyr Cys Val Lys Ile Ala Thr Phe Thr His Pro
        115                 120                 125

Val Phe Phe Trp Leu Lys His Lys Leu Ser Gly Trp Leu Pro Trp Met
    130                 135                 140

Leu Phe Ser Ser Val Gly Leu Ser Ser Phe Thr Thr Ile Leu Phe Phe
145                 150                 155                 160

Ile Gly Asn His Arg Met Tyr Gln Asn Tyr Leu Arg Asn His Leu Gln
                165                 170                 175

Pro Trp Asn Val Thr Gly Asp Ser Ile Arg Ser Tyr Cys Glu Lys Phe
            180                 185                 190

Tyr Leu Phe Pro Leu Lys Met Ile Thr Trp Thr Met Pro Thr Ala Val
        195                 200                 205

Phe Phe Ile Cys Met Ile Leu Leu Ile Thr Ser Leu Gly Arg His Arg
    210                 215                 220

Lys Lys Ala Leu Leu Thr Thr Ser Gly Phe Arg Glu Pro Ser Val Gln
225                 230                 235                 240

Ala His Ile Lys Ala Leu Leu Ala Leu Leu Ser Phe Ala Met Leu Phe
                245                 250                 255

Ile Ser Tyr Phe Leu Ser Leu Val Phe Ser Ala Ala Gly Ile Phe Pro
            260                 265                 270

Pro Leu Asp Phe Lys Phe Trp Val Trp Glu Ser Val Ile Tyr Leu Cys
        275                 280                 285

Ala Ala Val His Pro Ile Ile Leu Leu Phe Ser Asn Cys Arg Leu Arg
    290                 295                 300

Ala Val Leu Lys Ser Arg Arg Ser Ser Arg Cys Gly Thr Pro
305                 310                 315
```

<210> SEQ ID NO 49
<211> LENGTH: 900
<212> TYPE: DNA

<213> ORGANISM: Homo sapiens

<400> SEQUENCE: 49

```
atgcttcggt tattctattt ctctgctatt attgcctcag ttattttaaa ttttgtagga      60
atcattatga atctgtttat tacagtggtc aattgcaaaa cttgggtcaa aagccataga     120
atctcctctt ctgataggat tctgttcagc ctgggcatca ccaggtttct tatgctggga     180
ctatttctgg tgaacaccat ctacttcgtc tcttcaaata cggaaaggtc agtctacctg     240
tctgctttt  ttgtgttgtg tttcatgttt ttggactcga gcagtgtctg gtttgtgacc     300
ctgctcaata tcttgtactg tgtgaagatt actaacttcc aacactcagt gtttctcctg     360
ctgaagcgga atatctcccc aaagatcccc aggctgctgc tggcctgtgt gctgatttct     420
gctttcacca cttgcctgta catcacgctt agccaggcat cacctttcc tgaacttgtg     480
actacgagaa ataacacatc atttaatatc agtgagggca tcttgtcttt agtggtttct     540
ttggtcttga gctcatctct ccagttcatc attaatgtga cttctgcttc cttgctaata     600
cactccttga ggagacatat acagaagatg cagaaaaatg ccactggttt ctggaatccc     660
cagacggaag ctcatgtagg tgctatgaag ctgatggtct atttcctcat cctctacatt     720
ccatattcag ttgctaccct ggtccagtat ctccccttt  atgcagggat ggatatgggg     780
accaaatcca tttgtctgat ttttgccacc ctttactctc caggacattc tgttctcatt     840
attatcacac atcctaaact gaaacaaca  gcaagaaga  ttctttgttt caaaaatag      900
```

<210> SEQ ID NO 50
<211> LENGTH: 299
<212> TYPE: PRT
<213> ORGANISM: Homo sapiens

<400> SEQUENCE: 50

```
Met Leu Arg Leu Phe Tyr Phe Ser Ala Ile Ile Ala Ser Val Ile Leu
 1               5                  10                  15

Asn Phe Val Gly Ile Ile Met Asn Leu Phe Ile Thr Val Val Asn Cys
            20                  25                  30

Lys Thr Trp Val Lys Ser His Arg Ile Ser Ser Ser Asp Arg Ile Leu
        35                  40                  45

Phe Ser Leu Gly Ile Thr Arg Phe Leu Met Leu Gly Leu Phe Leu Val
    50                  55                  60

Asn Thr Ile Tyr Phe Val Ser Ser Asn Thr Glu Arg Ser Val Tyr Leu
65                  70                  75                  80

Ser Ala Phe Phe Val Leu Cys Phe Met Phe Leu Asp Ser Ser Ser Val
                85                  90                  95

Trp Phe Val Thr Leu Leu Asn Ile Leu Tyr Cys Val Lys Ile Thr Asn
            100                 105                 110

Phe Gln His Ser Val Phe Leu Leu Leu Lys Arg Asn Ile Ser Pro Lys
        115                 120                 125

Ile Pro Arg Leu Leu Leu Ala Cys Val Leu Ile Ser Ala Phe Thr Thr
    130                 135                 140

Cys Leu Tyr Ile Thr Leu Ser Gln Ala Ser Pro Phe Pro Glu Leu Val
145                 150                 155                 160

Thr Thr Arg Asn Asn Thr Ser Phe Asn Ile Ser Glu Gly Ile Leu Ser
                165                 170                 175

Leu Val Val Ser Leu Val Leu Ser Ser Ser Leu Gln Phe Ile Ile Asn
            180                 185                 190

Val Thr Ser Ala Ser Leu Leu Ile His Ser Leu Arg Arg His Ile Gln
```

```
                195                 200                 205
Lys Met Gln Lys Asn Ala Thr Gly Phe Trp Asn Pro Gln Thr Glu Ala
    210                 215                 220

His Val Gly Ala Met Lys Leu Met Val Tyr Phe Leu Ile Leu Tyr Ile
225                 230                 235                 240

Pro Tyr Ser Val Ala Thr Leu Val Gln Tyr Leu Pro Phe Tyr Ala Gly
                245                 250                 255

Met Asp Met Gly Thr Lys Ser Ile Cys Leu Ile Phe Ala Thr Leu Tyr
            260                 265                 270

Ser Pro Gly His Ser Val Leu Ile Ile Ile Thr His Pro Lys Leu Lys
        275                 280                 285

Thr Thr Ala Lys Lys Ile Leu Cys Phe Lys Lys
    290                 295

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

Leu Pro Phe Asn Gln Leu
 1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide

<400> SEQUENCE: 52

Leu Pro Phe Ser Gln Leu
 1               5

<210> SEQ ID NO 53
<211> LENGTH: 20
<212> TYPE: PRT
<213> ORGANISM: Artificial Sequence
<220> FEATURE:
<223> OTHER INFORMATION: Synthetic peptide

<400> SEQUENCE: 53

Tyr Gln Glu Pro Val Leu Gly Pro Val Arg Gly Val Arg Gly Pro Phe
 1               5                  10                  15

Pro Ile Ile Val
            20

<210> SEQ ID NO 54
<211> LENGTH: 13
<212> TYPE: PRT
<213> ORGANISM: Artificial Sequence
<220> FEATURE:
<223> OTHER INFORMATION: Synthetic peptide

<400> SEQUENCE: 54

Pro Val Leu Gly Pro Val Arg Gly Phe Pro Ile Ile Val
 1               5                  10

<210> SEQ ID NO 55
<211> LENGTH: 10
<212> TYPE: PRT
```

-continued

```
<213> ORGANISM: Artificial Sequence
<220> FEATURE:
<223> OTHER INFORMATION: Synthetic peptide

<400> SEQUENCE: 55

Pro Val Arg Gly Pro Phe Pro Ile Ile Val
 1               5                   10

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide

<400> SEQUENCE: 56

Arg Gly Pro Phe Pro Ile Ile Val
 1               5

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

Tyr Gln Glu Pro Val Leu Gly Pro Val Arg Gly Pro Phe Pro Ile Ile
 1               5                   10                  15

Val

<210> SEQ ID NO 58
<211> LENGTH: 14
<212> TYPE: PRT
<213> ORGANISM: Artificial Sequence
<220> FEATURE:
<223> OTHER INFORMATION: Synthetic peptide

<400> SEQUENCE: 58

Pro Val Leu Gly Pro Val Arg Gly Pro Phe Pro Ile Ile Val
 1               5                   10

<210> SEQ ID NO 59
<211> LENGTH: 17
<212> TYPE: PRT
<213> ORGANISM: Artificial Sequence
<220> FEATURE:
<223> OTHER INFORMATION: Synthetic peptide

<400> SEQUENCE: 59

Tyr Gln Glu Pro Val Leu Gly Pro Val Arg Glu Pro Phe Pro Ile Ile
 1               5                   10                  15

Val
```

IDENTIFICATION OF BITTER LIGANDS THAT SPECIFICALLY ACTIVATE HUMAN T2R RECEPTORS AND RELATED ASSAYS FOR IDENTIFYING HUMAN BITTER TASTE MODULATORS

RELATED APPLICATIONS

This application claims priority to and is a divisional of U.S. Ser. No. 13/019,580 filed Feb. 2, 2011, which is a continuation of U.S. Ser. No. 11/766,974 filed Jun. 22, 2007, now U.S. Pat. No. 7,883,856, which is a continuation-in-part of U.S. Ser. No. 11/555,617 filed on Nov. 1, 2006, now U.S. Pat. No. 8,030,008, which is in turn is a continuation-in-part of U.S. Ser. No. 10/191,058 filed Jul. 10, 2002, now U.S. Pat. No. 7,338,771 all of which applications are incorporated by reference in their entireties herein. These applications relate to the identification of hT2Rs and the use thereof in assays for the identification of ligands that activate specific T2Rs. These ligands are useful for modulating taste perception, particularly bitter taste.

SEQUENCE LISTING

This application includes as part of its disclosure a biological sequence listing text file which is being submitted via EFS-Web. Said biological sequence listing is contained in the file named "43268o2611.txt" having a size of 100,875 bytes that was created Apr. 2, 2014, which is hereby incorporated by reference in its entirety.

FIELD OF THE INVENTION

The present invention relates to the elucidation of bitter compounds that activate a number of previously reported human G-protein coupled receptors (GPCRs) in the T2R family that are involved in bitter taste perception. Specifically, the invention involves the discovery of bitter ligands that specifically bind and activate hT2R1, hT2R3, hT2R4, hT2R5, hT2R7, hT2R8, hT2R9, hT2R10, hT2R13, hT2R14, hT2R16, hT2R44, hT2R50, hT2R51, hT2R54, hT2R55, hT2R61, hT2R64, hT2R65, hT2R67, hT2R71, hT2R75, and hT2R76. Therefore, the above-identified human T2Rs may be used to identify compounds that modulate, preferably block, the bitter taste associated with these and other ligands.

More specifically, the present discoveries indicate that the subject human taste receptors, fragments, or variants or chimeras thereof, including orthologs, splice variants, single nucleotide polymorphisms (SNPS), and genetically engineered mutants thereof, are useful in assays, preferably high throughput cell-based assays, for identifying compounds that modulate (preferably block) the bitter taste of bitter ligands, as well as structurally related compounds and other compounds that activate these receptors. Compounds identified using these assays may be used as additives in foods, beverages or medicinal products to improve the taste thereof. Additionally, the invention relates to modified foods, beverages and medicinals that are treated and formulated in order to reduce or eliminate bitter compounds that activate the subject T2Rs.

Also, the present invention relates to the use of the subject T2R genes and the corresponding polypeptides and cells which express same in therapeutic screens, e.g., for identifying compounds that can be used to modulate gastrointestinal functions such as food sensing, absorption, regulation of gastrointestinal hormone and peptide secretion, transport and absorption, responses to toxins in the lingual and gastrointestinal systems, treatment of gastrointestinal and metabolic disorders such as eating disorders, diabetes, obesity, and the like.

DESCRIPTION OF THE RELATED ART

One of the basic taste modalities that humans can recognize is bitter. The physiology of bitter taste until quite recently was very poorly understood. Recent studies have started to shed light on the biology of taste (Lindemann, Nature (2001)). It is now known that many bitter compounds produce bitter taste by interacting with cell surface receptors. These receptors belong to the family of seven transmembrane domain receptors that interact with intracellular G proteins. A novel family of GPCRs, termed T2Rs, has been identified in humans and rodents (Adler et al., Cell 100(6):693-702 (2000); Chandrashekar et al., Cell 100(6): 703-711 (2000); Matsunami H, Montmayeur J P, Buck L B. Nature 404(6778): 601-4 (2000)). Several lines of evidence prior to the subject invention suggested that T2Rs mediate responses to bitter compounds. First, T2R genes are specifically expressed in subset of taste receptor cells of the tongue and palate epithelia. Second, the gene for one of the human T2Rs (hT2R1) is located in a chromosomal locus that is linked to sensitivity to bitter compound 6-n-propyl-2-thiouracil in humans (Adler et al., (Id.) (2000)). Third, one of the mouse T2Rs (mT2R5) is located in a chromosomal locus that is linked to sensitivity to bitter compound cycloheximide in mice. It was also shown that mT2R5 can activate gustducin, G protein specifically expressed in taste cells and linked to bitter stimuli transduction (Wong et al., Nature 381:796-800 (1996)). Gustducin activation by mT2R5 occurs only in response to cycloheximide (Chandrashekar et al., (Id.) (2000). Thus, it has been proposed that mT2R family mediates bitter taste response in mice, whereas hT2R family mediates bitter taste response in humans. Only one human T2R was suggested as having identified bitter ligand—hT2R4 was shown as being activated by denatonium (Chandrashekar et al., (Id.) 2000). However, effective denatonium concentrations used in the study (1.5 mM) were unusually high, i.e., is $10^5$-fold higher than the reported bitter threshold for denatonium to humans (Saroli, Naturwissenschaften 71:428-429 (1984)). Thus, no specific bitter ligand was convincingly matched to any hT2R. It has been also suggested that each hT2R is able to bind multiple bitter ligands. This hypothesis is based on the fact that hT2R family consists of only 24 identified members, whereas humans can recognize hundreds of different compounds as bitter. Sequences of hT2Rs have been previously reported and are discloses in published PCT applications by Zuker et al. (WO 01/18050 A2, (2001)) and Adler et al. (WO 01/77676 A1 (2001)) both of which are incorporated by reference in their entirety herein.

One of the difficulties of studying T2R function is that these receptors are not readily expressed in cultured mammalian cell lines. To improve T2R expression an N-terminal sequence from well-expressed GPCR, rhodopsin, was attached to T2R sequences (Chandrashekar et al., (Id.) 2000). This N-terminal tag also allowed easy monitoring of protein expression due to available antibody. In addition, SSTR3 tag (Bufe et al., Nat. Genet. 32:397-400 (2002)), a different N-terminal tag has been used to improve T2R expression. Whereas the incorporation of the rhodopsin tag improved expression of some T2Rs in mammalian cell lines, many of them still were not expressed well enough for functional studies. In a different approach mT2R5 was successfully expressed in insect Sf9 cells and used for functional studies using biochemical GTPγS binding assay (Chandrashekar et al., (Id.) 2000).

In Applicants' earlier patent application, U.S. Ser. No. 09/825,882 now patented, Applicants identified and provided the nucleic acid sequences and polypeptide sequences for a number of then-novel human taste receptors including hT2R51, hT2R54, hT2R55, hT2R61, hT2R63, hT2R64, hT2R65, hT2R67, hT2R71, and hT2R75. Additionally in US Ser. No. Applicants provided the polypeptide and DNA sequence for another identified novel human taste receptor named therein hT2R76.

Also, in U.S. Ser. No. 10/191,058 incorporated by reference herein in its entirety, Applicants discovered ligands that specifically activate three different human T2Rs. Additionally, Applicants recently filed U.S. Ser. No. 11/455,693 which further identified bitter ligands that specifically bind to other human T2Rs, and provided related assays.

Also, relating to practical utilities of the invention it has been reported that both T2Rs and T1Rs taste receptors are expressed in the gastrointestinal system For example, Wu et al., Proc, Natl. Acad. Sci, USA 99(4):2392-7 (2002) report that T2Rs are expressed in enterendocrine cells (STC1 cells) as well as gutducin and transducin subunits and that these cells likely respond to bitter ligands in the gastrointestinal tract. Also, it has been reported by Chen et al., AM J. Physiol. Cell Physol. 291(4):C726-39 (2006) that bitter taste stimuli induce Ca++ signaling and cholecystokinin (CCK) release in enterendocrine STC-1 cells. Also, Rozengurt, A J Phuysiol Gastrointes Liver Physiol 291(2):G171-7 (2006) report that taste receptors in the gut likely play a role in molecular sending the control of digestive funcuos, and hormonal and/or neutronal pathways and that they may play a role in the detection of harmful drugs and survival responses. Further, Stermini Am J Physiol Gastrointest Liver Physiol. 292(2): G457-61 (2007) report that taste receptors in the gut may be involved in gastrointestinal functions such as molecular sensing, nutrient absorption, protection from harmful substances, and further suggest that an understanding of these mechanisms may be relevant to disease states and conditions such as feeding disorders, and inflammation. Further, it has been recently suggested by Mace et al., J. Physiol. 2007 [Epub} that T2Rs and T1Rs activate phospholipase C beta 2, PLC beta2, and that there is likely a molecular intestinal sensing system in the gut similar to that present in lingual cells and that gastrointestinal cells such as brush cells or solitary chemosensory cells expressing taste receptors may result in GLUT2 increase and may play a role in nutrient sensing, and nutrition in the treatment of obesity and diabetes. Also, Cui et al, Curr Pharm Des. 12(35):4591-600 (2006) suggests that T1Rs expressed in the gut may be used in assays for compounds in treating obesity and diabetes as well as artificial sweeteners.

However, notwithstanding what has been reported and the understanding that T2R members regulate bitter taste, and their possible role in gastrointestinal functions there exists a need for the identification of specific ligands which activate human bitter T2R taste receptors. A greater understanding of the binding properties of different T2Rs, particularly human T2Rs, would be highly beneficial as it will greater facilitate the use thereof in selecting compounds having desired taste modulatory properties, i.e., which block or inhibit the taste of specific bitter compounds. Also, it will provide for the identification of compounds for treating and modulating gastrointestinal functions and related diseases such as obesity, diabetes, food absorption, fod sensing, eating disorders, and in the regulation of related hormones and peptides such as GLUT2, cholecystokin et al.

SUMMARY OF THE INVENTION

Toward that end, the present invention relates to the discovery of ligands that specifically bind and/or activate a total of 23 human taste receptors in the T2R family, particularly hT2R1, hT2R3, hT2R4, hT2R5, hT2R7, hT2R8, hT2R9, hT2R10, hT2R13, hT2R14, hT2R16, hT2R44, hT2R50, hT2R51, hT2R54, hT2R55, hT2R61, hT2R64, hT2R65, hT2R67, hT2R71, hT2R75 and hT2R76.

These discoveries were made using cell-based assays that measured the activity of T2Rs using cells that express a particular T2R in the presence and absence of specific bitter ligands. In particular, as described in greater detail infra, HEK cell lines expressing the above-identified specific T2Rs on their surface and which further expressed a chimeric G protein that functionally couple to said T2Rs were used in cell-based assays that detected changes in intracellular calcium concentrations, and were found to be specifically activated by specific bitter compounds whereas other hT2Rs were not activated under similar conditions.

Therefore, the invention embraces the use of these human taste receptors in assays, preferably high-throughput assays, to identify compounds that modulate, preferably block, the activation of these receptors by these and other bitter compounds.

Also, the invention relates to the use of these receptors to identify compounds that elicit a bitter taste.

Further, the present invention relates to the use of the subject T2Rs and corresponding polypeptides and cells which express same in therapeutic screening assays, e.g., for identifying compounds that regulate or modulate gastrointestinal functions such as food and nutrient sensing, food absorption, regulation of digestive hormones and peptides, responses to toxins, and for treating gastrointestinal or metabolic diseases such as obesity, diabetes, and inflamatory or autoimmune gastrointestinal diseases such as IBD, celiac disease, Crohn's disease, et al.

The invention also embraces assays which include an additional step which evaluates the effect of the identified modulating compounds in human or other taste tests, and evaluates the effect of the identified compounds on bitter taste and/or in further in vitro or in vivo clinical tests to evaluate the effect of an identified compound on a specific gastrointestinal, digestive or metabolic function or disease. Also, the invention embraces the use of the identified compounds in foods, beverages and medicines as flavor or taste modulators, i.e., to inhibit bitter taste, e.g., the bitter taste associated with specific beverages and foods or medicaments. Further, the invention embraces the production of food, beverages and medicinals which have been treated to remove compounds that specifically activate bitter taste receptors, e.g., foods and beverages that have been processed to remove or reduce the amount of bitter compounds comprised therein. Still further the present invention embraces medicaments containing identified compounds suitable for treating or preventing metabolic disorders, digestive functions, and gastrointestinal diseases involving T2Rs. Particularly, the present invention contemplates medicaments for treating or modulating conditions such as Crohn's, celiac disease, obesity, diabetes, food sensing, food absorption, digestive hormone or peptide secretion, and the like.

OBJECTS OF THE INVENTION

It is an object of the invention to provide assays that identify compounds which activate or which block or modulate the activation of at least one hT2R selected from hT2R1, hT2R3, hT2R4, hT2R5, hT2R7, hT2R8, hT2R9, hT2R10, hT2R13, hT2R14, hT2R16, hT2R44, hT2R50, hT2R51, hT2R54, hT2R55, hT2R61, hT2R64, hT2R65, hT2R67, hT2R71, hT2R75 and hT2R76 or fragments, variants, orthologs, or chimeras thereof by bitter ligands, including the specific bitter ligands disclosed herein found to specifically bind and activate these human bitter taste receptors.

It is a specific object of the invention to provide assays that identify compounds which activate or which block or modulate the activation and/or binding of hT2R1 or fragments, variants, or chimeras thereof by at least one of chloramphenicol, chloroquine, cyclooctanone, dexmethasone, diltiazem hydrochloride, Ginkgolide A, Lomefloxacin, N-methylthiourea, nitrosaccharin, methylprednisone, oleuropein, omeprazole, oxybutynin chloride, oxyphenonium HBr, peptide-LPFNQL (SEQ ID NO:51), peptide-LPFSQL (SEQ ID NO:52), Peptide-YQEPVLGPVRGVRGPFPIIV (SEQ ID NO:53), peptide PVLGPVRGFPIIV (SEQ ID NO:54), peptide PVRGPFPIIV (SEQ ID NO:55), peptide RGPFPIIV (SEQ ID NO:56), picric acid, prednisone, quinine, sulfamethoxazole, thioacetanilide, thiocarbanilide and other structurally related or bitter compounds.

It is another specific object of the invention to provide assays that identify compounds which activate or which block or modulate the activation and/or binding of hT2R3 or a fragment, ortholog, variant or chimera thereof by at least one of 2' acetylpyrazine, chloroquine or lomefloxacin or other structurally related and bitter compounds.

It is another object of the invention to provide assays that identify compounds which activate or which block or modulate the activation and/or binding of hT2R4 by at least one compound selected from 4-benzylpiperidine, chloroquine, diltiazem hydrochloride, diisobutylamine, 2,6-dimethylpiperidine, doxepin, labetalol HCl, (−)lupinine, 1-methyl-2-quinolinone, methylprednisolone, oleuropein, omeprazole, oxybutynin chloride, oxyphenonium HBr, pirenzepine dihydrochloride, procainamide, quinine, ranitidine, strychnine, theobromine, tolazoline, trimethoprim, and L-tryptophan and other structurally related or bitter compounds.

It is another object of the invention to provide assays that identify compounds which activate or which block or modulate the activation and/or binding to hT2R5 by at least one compound selected from dimethylbiguanide, 1-methyl-2-quinolinone, oleuropein, and 2-picoline and other structurally related and bitter compounds.

It is another object of the invention to provide assays that identify compounds which activate or which block or modulate the activation and/or binding of hT2R7 with at least one compound selected from 2-acetylpyrazine, chloroquine, ethylpyrazine, 1-methyl-2-quinolinone, oxybutynin chloride, oxyphenonium HBr, 2-picoline, pirenzepine dihydrochloride, quinine, strychnine, trimethoprim and other structurally related or bitter compounds.

It is another object of the invention to provide assays that identify compound which activate or which block or modulate the activation and/or binding of hT2R8 with at least one compound selected from acesulfame K, 2-acetylpyrazine, aloin, andrographolide, atropine, chloramphenicol, cycloheximide, cyclooctanone, denatonium benzoate, dexamethasone, diltiazem hydrochloride, enalapril maleate, (−) erythromycin, ethylpyrazine, famotidine, gabapentin, ginkgolide A, goitrin, guaiacol glyceryl ether, lomefloxacin, 1-meth-2-quinolinone, methylprednisolone, nitrophthalene, nitrosaccharin, oleuropein, oxybutynin chloride, oxyphenonium HBr, N'-ethyl-N'-phenylurea, picric acid, pirenzepine dihydrochloride, prednisone, quinacrine, ranitidine, saccharin, sucrose octaacetate, strychnine, tolylurea, and trimethoprim and other structurally related or bitter compounds.

It is another object of the invention to provide assays that identify compounds which activate or which block or modulate the activation and/or binding of hT2R9 by at least one compound selected from ethylpyrazine, ofloxacin, and ranitidine and other structurally related or bitter compounds.

It is another specific object of the invention to provide assays that identify compounds which activate or which block or modulate the activation and/or binding of hT2R10 to at least one compound selected from 2-acetylpyrazine, andrographolide, atropine, brucine, 4-benzylpiperidine, caffeine, chloramphenicol, chloroquine, cinchonine, clarithromycin, clindamycin, cycloheximide, cyclooctanone, denatonium benzoate, dexamethasone, diltiazem hydrochloride, diisobutylamine, 2,6-dimethylpiperidine, doxepin, edrophonium, (−) erythromycin, ethylpyrazine, famotidine, gabapentin, ginkgolide A. goitrin, guaiacol glyceryl ether, (−) lupinine, 1-methyl-2-quinolinone, methylprednisolone, oleuropein, omeprazole, oxybutynin chloride, oxyphenonium HBr, procainamide, prednisone, quassin, quinacrine, quinine, ranitidine, spartein sulfate pentahydrate, sucrose octaacetate, strychnine, tolazoline, tolylurea, trapidil, and trimethoprim, chloride and other structurally related or bitter compounds.

It is another object of the invention to provide assays that identify compounds which activate or which block or modulate the activation and/or binding of hT2R13 to at least one compound selected from 2-acetylpyrazine, atropine, clarithromycin, denatonium benzoate, doxepin, ethylpyrazine, oleuropein, oxyphenonium HBr, and quinacrine and other structurally related or bitter compounds.

It is another object of the invention to provide assays that identify compounds that activate or which block or modulate the activation and/or binding of hT2R14 to at least one compound selected from 2-acetylpyrazine, arisolochic acid, cyclooctanone, dexamethasone, diltiazem hydrochloride, 2,6-dimethylpiperidine, erythromycin, ethylpyrazine, goitrin, guaiacol glyceryl ether, 1-methyl-2-quinolinone, methylprednisolone, nitronaphthalene, nitrosaccharin, oleuropein, omeprazole, oxybutynin chloride, N'-ethyl-N'-phenylurea, 2-picoline, picric acid, quinine, strychnine, theobromine, tolylurea, and trapidil and other structurally related or bitter compounds.

It is another object of the invention to provide assays which identify compounds that activate or which block or modulate the activation and/or binding of hT2R16 to at least one compound selected from 2-acetylpyrazine, amygadalin, arbutin, linamarin, and D-(−)-salicin and other structurally related or bitter compounds.

It is another object of the invention to provide assays which identify compounds that activate or which block or modulate the activation and/or binding of hT2R44 to at least one compound selected from 2-acetylpyrazine or ethylpyrazine and other structurally related or bitter compounds.

It is another object of the invention to provide assays which identify compounds that activate or which block or modulate the activation and/or binding of hT2R50 to at least one compound selected from 2-acetylpyrazine or ethylpyrazine or other structurally related or bitter compounds.

It is another object of the invention to provide assays which identify compounds that activate or which block or modulate the activation and/or binding of hT2R54 to at least one compound selected from acetaminophen, chloroquine, clarithromycin, denatonium benzoate, (−)-epicatechin, (−)-erythromycin, labetalol-HCl, oleuropein, omeprazole, oxybutynin chloride, oxyphenonium HBr, pirenzepine dihydrochloride, procainamide, ranitidine, strychnine, trimethoprim, and L-tryptophan and other structurally related or bitter compounds.

It is another object of the invention to provide assays for identifying compounds that activate or which block or modulate the activation and/or binding of hT2R55 to at least one compound selected from doxepin, linamarin, oxybutynin chloride, quinine, strychnine, and trimethoprim and other structurally related or bitter compounds.

It is another object of the invention to provide assays for identifying compounds that activate or which block or modulate the activation and/or binding of hT2R61 by at least one compound selected from acesulfame K, aloin, aristolochic acid, caffeine, chloramphenicol, chloroquine, denatonium benzoate, nitrooxybutinin chloride, oxyphenonium, peptide-LPFNQL (SEQ ID NO:51), peptide-LPFSQL (SEQ ID NO:52), Picric acid, saccharin, and strychnine and other structurally related or bitter compounds.

It is also an object of the invention to provide assays for identifying compounds that activate or which block or modulate the activation and/or binding of hT2R64 by at least one compound selected from acesulfame k, amino-2-norbornane-carboxylic acid, aristolochic acid, 2,6-dimethylpiperidine, quinine, ranitidine, saccharin, strychnine, and L-tryptophan and other structurally related or bitter compounds.

It is also an object of the invention to provide assays for identifying compounds that activate or which block or modulate the activation and/or binding of hT2R65 by at least one compound selected from 2-acetylpyrazine, ethylpyrazine, and 1-methyl-2-quinolinone and other structurally related or bitter compounds.

It is also an object of the invention to provide assays for identifying compounds that block or modulate the activation and/or binding of hT2R67 by at least one compound selected from 2-acetylpyrazine, andrographolide, ethylpyrazine, and oxybutynin chloride and other structurally related or bitter compounds.

It is also an object of the invention to provide assays for identifying compounds that activate or which block or modulate the activation and/or binding of hT2R71 by at least one compound selected from nitrosaccharin, and picric acid and other structurally related or bitter compounds.

It is another object of the invention to provide assays for identifying compounds that activate or which block or modulate the activation and/or binding of hT2R75 by at least one compound selected from andrographolide, atropine, brucine, 4-benzylpiperidine, caffeine, chloramphenicol, chloroquine, cinchonine, ciprofloxacin denatonium benzoate, dexamethasone, doxepin, enalapril maleate, enoxacin, prednisone, procainamide, quassin, quinine, ranitidine, spartein sulfate pentahydrate, strychnine, sulfamethoxazole, trapidil, and trimethoprim and other structurally related or bitter compounds.

It is another object of the invention to provide assays for identifying compounds that activate or which block or modulate the activation and/or binding of hT2R76 by at least one compound selected from brucine, and other structurally related or bitter compounds It is a specific object of the invention to use cells or cell membranes that comprise or express (stably or transiently) at least one of hT2R1, hT2R3, hT2R4, hT2R5, hT2R7, hT2R8, hT2R9, hT2R10, hT2R13, hT2R14, hT2R16, hT2R44, hT2R50, hT2R51, hT2R54, hT2R55, hT2R61, hT2R64, hT2R65, hT2R67, hT2R71, hT2R75 and hT2R76 or a fragment, variant, ortholog, mutant or chimera thereof in assays to identify compounds that activate or which block or modulate the activation of at least one of said receptor by one of the above-identified bitter compounds or another structurally related or bitter compound.

It is an even more specific object of the invention to use cells, preferably mammalian, amphibian or insect cells, e.g., HEK293T cells that express a G protein that couples thereto, e.g., $G_{\alpha 15}$, $G_{\alpha 16}$, gustducin or a chimera thereof, e.g., $G_{\alpha 16}$ gustducin or transducin chimeric G protein in cell-based assays that detect changes in intracellular calcium order to detect compounds that activate or which modulate, preferably block or inhibit, the activation of one of the afore-mentioned human taste receptors by one of the afore-mentioned bitter compounds or another structurally related or bitter compound.

It is another object of the invention to confirm that the identified compounds modulate, preferably inhibit or block, bitter taste, e.g. that elicited by the afore-identified bitter compounds or other structurally related bitter compounds in human or animal taste tests, preferably human taste tests.

It is another object of the invention to utilize compounds identified in the assays described herein as additives or flavor modulators in compositions in order to inhibit or block the bitter taste elicited by compounds that specifically activate these taste receptors. A preferred object of the invention is to use a compound that inhibits activation of at least one of the above-identified human T2R receptors in order to block the bitter taste of compounds present in some foods, beverages, cosmetics and medicinals.

DETAILED DESCRIPTION OF THE FIGURES

FIG. 1 contains a Table which compares the nomenclature used by different groups in referring to human bitter taste receptors (hT2Rs).

FIGS. 2A-C contains a Table which tabulates the results of calcium imaging experiments which identified specific bitter ligands that bind and specifically activate the hT2Rs identified therein.

FIGS. 3A-B contains a table summarizing the particular bitter ligands tested as well as the concentrations used in the calcium imaging assays the results of which are summarized in FIG. 2.

FIG. 4 compares the functional activity of 2 different hT2R9 alleles (hT2R9A and hT2R9V) in HEK-293 cells using the bitter ligand ofloxacin.

FIG. 5 compares the functional activity of the same 2 hT2R9 alleles using a different expression system comprising the SSTR label and transiently transfected cells and detection of hT2R9 activity using FLIPR and a different bitter ligand (ranitidine).

DETAILED DESCRIPTION OF THE INVENTION

Prior to specifically describing the invention, the following definitions are provided.

The term "T2R" family includes polymorphic variants, alleles, mutants, and homologs that: (1) have about 30-40% amino acid sequence identity, more specifically about 40, 50, 60, 70, 75, 80, 85, 90, 95, 96, 97, 98, or 99% amino acid sequence identity to the T2Rs disclosed infra, and in the Zuker (Id) (2001) and Adler (Id.) (2001) applications incorporated, by reference herein over a window of about 25 amino acids, optimally 50-100 amino acids; (2) specifically bind to antibodies raised against an immunogen comprising an amino acid sequence selected from the group consisting of the T2R sequences disclosed infra, and conservatively modified variants thereof; (3) specifically hybridize (with a size of at least about 100, optionally at least about 500-1000 nucleotides) under stringent hybridization conditions to a sequence selected from the group consisting of the T2R DNA sequences disclosed infra, and conservatively modified variants thereof; (4) comprise a sequence at least about 40% identical to an amino acid sequence selected from the group consisting of the T2R amino acid sequences disclosed infra or (5) are amplified by primers that specifically hybridize under stringent hybridization conditions to the described T2R sequences.

In particular, these "T2R's" include taste receptor GPCRs referred to herein as hT2R1, hT2R3, hT2R4, hT2R5, hT2R7, hT2R8, hT2R9A, hT2R9V, hT2R10, hT2R13, hT2R14, hT2R16, hT2R44, hT2R50, hT2R54, hT2R55, hT2R61, hT2R64, hT2R65, hT2R67, hT2R71, hT2R75, and hT2R76 having the nucleic acid sequences and amino acid sequences provided in this application, and variants, alleles, mutants, orthologs and chimeras thereof which specifically bind to bitter ligands which are identified herein and other structurally related compounds and bitter compounds.

As noted in the Table in FIG. 1 the hT2Rs herein have also been referred to in the literature by other names. Herein when Applicants refer to a T2R sequence the Senomyx nomenclature is intended.

While T2R genes exhibit substantial sequence divergence at both the protein and DNA level, all T2Rs isolated to date have been found to contain certain consensus sequences in particular regions that are identical or which possess or at least 70-75% sequence identity to the T2R consensus sequence identified previously in the Adler et al (WO 01/77676 A1 (2001) and Zuker et al. WO 01/18050 A2, both incorporated by reference in their entirety herein.

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al, Cell, 96:541-51 (1999); Buck & Axel, Cell, 65:175-87 (1991)). These regions can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). These regions are useful for making chimeric proteins and for in vitro assays of the invention, e.g., ligand binding assays. For example chimeric T2Rs can be made by combining the extracellular region of one T2R and the transmembrane region of another T2R of the same or different species.

"Extracellular domains" therefore refers to the domains of T2R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays.

"T2R Expressing Cell" herein encompasses recombinant cells which express a human T2R sequence according to the invention as well as endogenous T2R expressing cells. Such cells are comprised in the lingual and gastrointestinal system and include cells in the oral cavity such as taste buds expressed on the tongue as well as cellin in the gastrointestinal system and associated organs such as brush cells in the gastrointestinal tract, enteroendocrine cells such as STC-1 cells. These cells may also express a G protein such as gustducin, transducin, Galpha15 or Galpha16. Cells which express specific T2Rs can be identified and isolated by known methods such as by FACS cell separation of magnetic bead cell isolation procedures.

"Transmembrane domain," which comprises the seven transmembrane "regions," refers to the domain of T2R polypeptides that lies within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte & Doolittle, J. Mol. Biol., 157:105-32 (1982)), or in Stryer, supra.

"Cytoplasmic domains" refers to the domains of T2R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII). The families of olfactory and certain taste receptors each belong to this superfamily. 7-transmembrane receptor polypeptides have similar and characteristic primary, secondary and tertiary structures, as discussed in further detail below.

The term "ligand-binding region" refers to sequences derived from a chemosensory or taste receptor that substantially incorporates transmembrane domains II to VII (TM II to VII). The region may be capable of binding a ligand, and more particularly, a taste eliciting compound.

The term "plasma membrane translocation domain" or simply "translocation domain" means a polypeptide domain which when incorporated into the amino terminus of a polypeptide coding sequence, can with great efficiency "chaperone" or "translocate" the hybrid ("fusion") protein to the cell plasma membrane. For example a particular "translocation domain" initially derived from the amino terminus of the human rhodopsin receptor polypeptide, a 7-transmembrane receptor can be used. Another translocation domain has been derived from the bovine rhodopsin sequence and is also useful for facilitating translocation. Rhodopsin derived sequences are particularly efficient in translocating 7-transmembrane fusion proteins to the plasma membrane.

"Functional equivalency" means the domain's ability and efficiency in translocating newly translated proteins to the plasma membrane as efficiently as an exemplary translocation domain such as one derived from rhodopsin under similar conditions; relative efficiencies can be measured (in quantitative terms) and compared, as described herein. Domains falling within the scope of the invention can be determined by routine screening for their efficiency in translocating newly synthesized polypeptides to the plasma membrane in a cell (mammalian, *Xenopus*, and the like) with the same efficiency as the twenty amino acid long translocation domain SEQ ID NO:1.

The phrase "functional effects" in the context of assays for testing compounds that modulate T2R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a T2R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T2R gene expression; tissue culture cell T2R expression; transcriptional activation of T2R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T2R proteins receptors are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with extracellular proteins that bind activators or inhibitor (e.g., ebnerin and other members of the hydrophobic carrier family); G Proteins; kinases (e.g., homologs of rhodopsin kinase and beta adrenergic receptor kinases that are involved in deactivation and desensitization of a receptor); and arrestins, which also deactivate and desensitize receptors. Modulators include genetically modified versions of T2R family members, e.g., with altered activity, as well as naturally occurring and synthetic ligands, antagonists, agonists, small chemical molecules and the like.

Such assays for inhibitors and activators include, e.g., expressing T2R family members in cells or cell membranes, applying putative modulator compounds in the presence or absence of compounds that modulate, e.g., bitter compounds, and then determining the functional effects on taste transduction, as described above. Samples or assays comprising T2R family members that are treated with a potential activator, inhibitor, or modulator are compared to control samples without the inhibitor, activator, or modulator to examine the extent of modulation. Control samples (untreated with modulators) are assigned a relative T2R activity value of 100%. Inhibition of a T2R is achieved when the T2R activity value relative to the control is about 80%, optionally 50% or 25-0%. Activation of a T2R is achieved when the T2R activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state. Preferably, "purified," "substantially purified," and "isolated" means that the composition comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated", when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific oligonucleotide primer pairs) for amplifying (e.g., by polymerase chain reaction, PCR) naturally expressed (e.g., genomic or mRNA) or recombinant (e.g., cDNA) nucleic acids of the invention (e.g., taste eliciting compound-binding sequences of the invention) in vivo or in vitro.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

The term "library" means a preparation that is a mixture of different nucleic acid or poly-peptide molecules, such as the library of recombinant generated sensory, particularly taste receptor ligand-binding regions generated by amplification of nucleic acid with degenerate primer pairs, or an isolated collection of vectors that incorporate the amplified ligand-binding regions, or a mixture of cells each randomly transfected with at least one vector encoding an taste receptor.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., Nucleic Acid Res., 19:5081 (1991); Ohtsuka et al., J. Biol. Chem., 260:2605-08 (1985); Rossolini et al., Mol. Cell. Probes, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "translocation domain," "ligand-binding region", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gin/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W. H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding regions, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$ for —C(=O)—NH—), aminomethylene (CH$_2$NH), ethylene, olefin (CH.dbd.CH), ether (CH$_2$O), thioether (CH$_2$—S), tetrazole (CN$_4$), thiazole, retroamide, thioamide, or ester (see, e.g., Spatola, Chemistry and Biochemistry of Amino Acids, Peptides and Proteins, Vol. 7, 267-357, Marcell Dekker, Peptide Backbone Modifications, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T2R" antibody is an antibody or antibody fragment that specifically binds a polypeptide encoded by a T2R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein.

For example, polyclonal antibodies raised to a T2R family member from specific species such as rat, mouse, or human can be selected to obtain only those polyclonal antibodies that are specifically immunoreactive with the T2R polypeptide or an immunogenic portion thereof and not with other proteins, except for orthologs or polymorphic variants and alleles of the T2R polypeptide. This selection may be achieved by subtracting out antibodies that cross-react with T2R molecules from other species or other T2R molecules. Antibodies can also be selected that recognize only T2R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa, HEK-293, and the like, e.g., cultured cells, explants, and cells in vivo.

Based on the foregoing, the present invention provides assays for identifying compounds that modulate, preferably block, the specific activation of the previously identified human bitter taste receptor by bitter compounds, e.g., the bitter compounds identified in FIGS. 2 and 3 and structurally related and other bitter compounds. Particularly, the invention provides cell-based assays for identifying compounds that modulate (e.g., block) the activation of hT2R1, hT2R3, hT2R4, hT2R5, hT2R7, hT2R8, hT2R9, hT2R10, hT2R13, hT2R14, hT2R14, hT2R16, hT2R44, hT2R50, hT2R51, hT2R54, hT2R55, hT2R61, hT2R64, hT2R65, hT2R67, hT2R71, hT2R75, hT2R76 by one of the bitter ligands shown to activate these specific taste receptors identified in FIG. 2 or another structurally related or another bitter compound. These compounds will modulate bitter taste associated with these taste receptors in human subjects. This will be confirmed in taste tests.

That the above taste receptors specifically respond to at least one of the bitter ligands contained in FIG. 2 was determined essentially using the HEK293 expression system and calcium imaging methods reported in other publications as well as patent applications filed by the present Assignee, e.g., U.S. Ser. Nos. 10/191,058 and 09/825,882, both incorporated by reference in their entireties herein. More particularly, the present inventors transfected HEK293 cells with a particular hT2R tagged with a rhodopsin 35 amino acid tag (SEQ ID NO:1) together with a chimeric G protein (G16gust44) which comprises the $G_{\alpha 16}$ G protein sequence modified by the replacement of carboxy-44 amino acid residues with those of gustducin, and recorded responses of these cells to specific bitter ligands by calcium imaging methods.

Specifically, the inventors used a mammalian cell-based assay to monitor hT2R activities. For calcium imaging assays, cells were seeded into 48-well tissue culture plates. 24 hours later the cells were transiently transfected with an expression plasmid (pEAK10) containing an hT2R nucleic acid sequence, and a plasmid (pEAK10) containing a chimeric G protein (G16gust44). Another 24 hours later the cells were incubated with a fluorescent dye specific for calcium (Fluo-4; Molecular Probes). The loaded cells are exposed o different bitter molecules, and the activation of an hT2R leads t activation of G16gust44, which in turn leads to calcium mobilization inside within the cells. This increase in calcium concentration changes the fluorescence properties of the calcium dye inside the cells. These changes are monitored using fluorescence microscopy.

The inventors also used the automated fluorimetric aiming system FLIPR using a slightly different protocol. A HEK293 cell line stably expressing G16gust44 was transfected with a hT2R expression plasmid, 24 hours later, the cells are loaded and analyzed on FLIPR.

After a ligand is identified for a particular hT2R, a HEK293 cell line stably expressing both the hT2R and G16gust44 are generated facilitating future screening assays to identify other ligands that activate the particular hT2R or which modulate (block or enhance) the activation of this hT2R by another bitter ligand such as a compound identified in FIG. 2. This avoids the need for transient transfection.

As shown in the Figures such experiments identified ligand-receptor pairs for 23 different hT2Rs. It was found that most tested bitter molecules activated more than 1 hT2R, and also that most hT2Rs are broadly "tuned" to respond to structurally diverse bitter molecules. As noted, all the identified bitter ligands and the concentrations at which they were tested in the calcium imaging assays is contained in FIG. 3. In addition, FIGS. 4 and 5 reveal that different T2R alleles may respond to biter ligands differently and that such allelic variants may affect bitter taste and/or other T2R associated activities in different individuals depending upon what T2R allele(s) they express.

These results indicate that cells which functionally express any one of the identified hT2R taste receptors may be used in assays to identify legends that modulate bitter taste associated with at least one of said particular hT2Rs.

Preferably, these assays will utilize a test cell that expresses a DNA encoding an hT2R having one of the amino acid sequences identified infra. However, it is anticipated that fragments, orthologs, variants or chimeras of these receptor polypeptides which retain the functional properties of these bitter taste receptors, i.e., respond to some bitter compounds, will also be useful in these assays. Examples of such variants include splice variants, single nucleotide polymorphisms, allelic variants, and mutations produced by recombinant or chemical means, or naturally occurring. Means for isolation and expression of T2Rs, which are used in the assays of the present invention and assays which are contemplated for use in the present invention to identify compounds that inhibit activation of these receptors, are set forth below.

Isolation and Expression of T2Rs

Isolation and expression of the T2Rs, or fragments or variants thereof, of the invention can be effected by well-established cloning procedures using probes or primers constructed based on the T2R nucleic acids sequences disclosed in the application. Related T2R sequences may also be identified from human or other species genomic databases using the sequences disclosed herein and known computer-based search technologies, e.g., BLAST sequence searching. In a particular embodiment, the pseudogenes disclosed herein can be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

Alternatively, these nucleic acids can be synthesized in vitro by well-known chemical synthesis techniques, as described in, e.g., Carruthers, Cold Spring Harbor Symp. Quant. Biol. 47:411-18 (1982); Adams, Am. Chem. Soc., 105:661 (1983); Belousov, Nucleic Acids Res. 25:3440-3444 (1997); Frenkel, Free Radic. Biol. Med. 19:373-380 (1995); Blommers, Biochemistry 33:7886-7896 (1994); Narang, Meth. Enzymol. 68:90 (1979); Brown, Meth. Enzymol. 68:109 (1979); Beaucage, Tetra. Lett. 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: A Laboratory Manual (2nd ed.), Vols. 1-3, Cold Spring Harbor Laboratory (1989); Ausubel, ed., Current Protocols in Molecular Biology, John Wiley & Sons, Inc., New York (1997); Tijssen, ed., Laboratory Techniques in Biochemistry and Molecular Biology: Hybridization With Nucleic Acid Probes, Part I, Theory and Nucleic Acid Preparation, Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acids encoding a T2R ligand-binding region. The nucleic acids described herein can also be cloned or measured quantitatively using amplification techniques. Amplification methods are also well known in the art, and include, e.g., polymerase chain reaction (PCR) (Innis ed., PCR Protocols, a Guide to Methods and Applications, Academic Press, N.Y. (1990); Innis ed., PCR Strategies, Academic Press, Inc., N.Y. (1995)); ligase chain reaction (LCR) (Wu, Genomics, 4:560 (1989); Landegren, Science, 241:1077 (1988); Barringer, Gene, 89:117 (1990)); transcription amplification (Kwoh, PNAS, 86:1173 (1989)); self-sustained sequence replication (Guatelli, PNAS, 87:1874 (1990)); Q Beta replicase amplification (Smith, J. Clin. Microbiol., 35:1477-91 (1997)); automated Q-beta replicase amplification assay (Burg, Mol. Cell. Probes, 10:257-71 (1996)); and other RNA polymerase mediated techniques (e.g., NASBA, Cangene, Mississauga, Ontario). See also, Berger, Methods Enzymol., 152:307-16 (1987); Sambrook; Ausubel; U.S. Pat. Nos. 4,683,195 and 4,683,202; Sooknanan, Biotechnology, 13:563-64 (1995).

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp E1 sites were designed into the exemplary primer pairs of the invention. These particular restriction sites have a sequence that, when ligated, are "in-frame" with respect to the 7-membrane receptor "donor" coding sequence into which they are spliced (the ligand-binding region coding sequence is internal to the 7-membrane polypeptide, thus, if it is desired that the construct be translated downstream of a restriction enzyme splice site, out of frame results should be avoided; this may not be necessary if the inserted ligand-binding region comprises substantially most of the transmembrane VII region). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs may be designed to selectively amplify ligand-binding regions of T2R proteins. These binding regions may vary for different ligands; thus, what may be a minimal binding region for one ligand, may be too limiting for a second potential ligand. Thus, binding regions of different sizes comprising different domain structures may be amplified; for example, transmembrane (TM) domains II through VII, III through VII, III through VI or II through VI, or variations thereof (e.g., only a subsequence of a particular domain, mixing the order of the domains, and the like), of a 7-transmembrane T2R.

As domain structures and sequence of many 7-membrane T2R proteins are known, the skilled artisan can readily select domain-flanking and internal domain sequences as model sequences to design degenerate amplification primer pairs. For example, a nucleic acid sequence encoding domain regions II through VII can be generated by PCR amplification using a primer pair. To amplify a nucleic acid comprising transmembrane domain I (TM I) sequence, a degenerate primer can be designed from a nucleic acid that encodes the amino acid sequence of the T2R family consensus sequence 1 described above. Such a degenerate primer can be used to generate a binding region incorporating TM I through TM III, TM I through TM IV, TM I through TM V, TM I through TM VI or TM I through TM VII). Other degenerate primers can be designed based on the other T2R family consensus sequences provided herein. Such a degenerate primer can be used to generate a binding region incorporating TM III through TM IV, TM III through TM V, TM III through TM VI or TM III through TM VII.

Paradigms to design degenerate primer pairs are well known in the art. For example, a COnsensus-DEgenerate Hybrid Oligonucleotide Primer (CODEHOP) strategy computer program is accessible as http://blocks.fhcrc.org/codehop.html, and is directly linked from the BlockMaker multiple sequence alignment site for hybrid primer prediction beginning with a set of related protein sequences, as known taste receptor ligand-binding regions (see, e.g., Rose, Nucleic Acids Res., 26:1628-35 (1998); Singh, Biotechniques, 24:318-19 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, Nucleic Acids Res., 25:4866-71 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, Nat. Struct. Biol., 5:950-54 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, PNAS, 95:4258-63 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T2R polypeptides and polymorphic variants, alleles, and interspecies homologs thereof, by detecting expressed homologs immunologically with antisera or purified antibodies made against a T2R polypeptide, which also recognize and selectively bind to the T2R homolog.

Nucleic acids that encode ligand-binding regions of taste receptors may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from taste receptor-expressing cells.

In one embodiment, hybrid protein-coding sequences comprising nucleic acids encoding T2Rs fused to a translocation sequences may be constructed. Also provided are hybrid T2Rs comprising the translocation motifs and taste eliciting compound-binding regions of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, Biochimie, 80:289-93 (1998)), subtilisin protease recognition motif (see, e.g., Polyak, Protein Eng., 10:615-19 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, Biochemistry, 34:1787-97 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature (see, e.g., Kroll, DNA Cell. Biol. 12:441-53 (1993)).

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Roberts, Nature, 328:731 (1987); Berger supra; Schneider, Protein Exper. Purif., 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences (see, e.g., Blondelet-Rouault, Gene, 190:315-17 (1997); Aubrecht, J. Pharmacol. Exp. Ther., 281:992-97 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T2R ligand-binding region within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, Protein Sci., 2:55-70 (1993). Other alignment and modeling algorithms are well known in the art (see, e.g., Peitsch, Receptors Channels, 4:161-64 (1996); Kyte & Doolittle, J. Md. Biol., 157:105-32 (1982); and Cronet, Protein Eng., 6:59-64 (1993).

The present invention also includes not only the nucleic acid molecules and polypeptides having the specified nucleic and amino acid sequences, but also fragments thereof, particularly fragments of, e.g., 40, 60, 80, 100, 150, 200, or 250 nucleotides, or more, as well as polypeptide fragments of, e.g., 10, 20, 30, 50, 70, 100, or 150 amino acids, or more. Optionally, the nucleic acid fragments can encode an antigenic polypeptide that is capable of binding to an antibody raised against a T2R family member. Further, a protein fragment of the invention can optionally be an antigenic fragment that is capable of binding to an antibody raised against a T2R family member.

Also contemplated are chimeric proteins, comprising at least 10, 20, 30, 50, 70, 100, or 150 amino acids, or more, of one of at least one of the T2R polypeptides described herein, coupled to additional amino acids representing all or part of another GPCR, preferably a member of the 7 transmembrane superfamily. These chimeras can be made from the instant receptors and another GPCR, or they can be made by combining two or more of the present receptors. In one embodiment, one portion of the chimera corresponds to, or is derived from the transmembrane domain of a T2R polypeptide of the invention. In another embodiment, one portion of the chimera corresponds to, or is derived from the one or more of the transmembrane regions of a T2R polypeptide described herein, and the remaining portion or portions can come from another GPCR. Chimeric receptors are well known in the art, and the techniques for creating them and the selection and boundaries of domains or fragments of G Protein-Coupled Receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

For example, a region such as a ligand-binding region, an extracellular domain, a transmembrane domain, a transmembrane domain, a cytoplasmic domain, an N-terminal domain, a C-terminal domain, or any combination thereof, can be covalently linked to a heterologous protein. For instance, a T2R transmembrane region can be linked to a heterologous GPCR transmembrane domain, or a heterologous GPCR extracellular domain can be linked to a T2R transmembrane region. Other heterologous proteins of choice can include, e.g., green fluorescent protein, .beta.-galactosidase polypeptides, glutamate receptor, and the rhodopsin polypeptides, e.g., N-terminal fragments of rhodopsin e.g., bovine rhodopsin.

It is also within the scope of the invention to use different host cells for expressing the T2Rs, fragments, or variants of the invention. To obtain high levels of expression of a cloned gene or nucleic acid, such as cDNAs encoding the T2Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. Preferably, eukaryotic expression systems are used to express the subject hT2R receptor.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T2R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Assays for Detection of Compounds that Modulate the Activity of a hT2R According to the Invention Methods and compositions for determining whether a test compound specifically binds to a T2R polypeptide of the invention, both in vitro and in vivo are described below. Many aspects of cell physiology can be monitored to assess the effect of ligand-binding to a naturally occurring or chimeric T2Rs. These assays may be performed on intact cells expressing a T2R polypeptide, on permeabilized cells, or on membrane fractions produced by standard methods.

Taste receptors bind taste eliciting compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

The subject hT2R proteins or polypeptides of the assay will typically be selected from a polypeptide having a sequence contained in the sequence listing preceding the claims herein or fragments or conservatively modified variants thereof.

Alternatively, the T2R proteins or polypeptides of the assay can be derived from a eukaryotic host cell, and can include an amino acid sequence having a certain percentage amino acid sequence identity to these hT2R polypeptides or conservatively modified variants thereof. Generally, the amino acid sequence identity will be at least 30% preferably 30-40%, more specifically 50-60, 70%, 75%, 80%, 85%, 90%, 95%, 96%, 97%, 98%, or 99%. Optionally, the T2R proteins or polypeptides of the assays can comprise a region of a T2R polypeptide, such as an extracellular domain, transmembrane region, cytoplasmic domain, ligand-binding domain, and the like. Optionally, as exemplified herein the T2R polypeptide, or a portion thereof, can be covalently linked to a heterologous protein to create a chimeric protein used in the assays described herein.

Modulators of T2R activity may be tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

Detection of Modulators

Compositions and methods for determining whether a test compound specifically binds to a T2R receptor of the invention, both in vitro and in vivo, are described below. Many aspects of cell physiology can be monitored to assess the effect of ligand binding to a T2R polypeptide of the invention. These assays may be performed on intact cells expressing a chemosensory receptor, on permeabilized cells, or on membrane fractions produced by standard methods or in vitro using de novo synthesized proteins.

In vivo, taste receptors bind to taste modulatory compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Alternatively, the T2R proteins or polypeptides of the assay can be derived from a eukaryotic host cell and can include an amino acid subsequence having amino acid sequence identity to the T2R polypeptides disclosed herein, or fragments or conservatively modified variants thereof. Generally, the amino acid sequence identity will be at least 35 to 50%, or optionally 75%, 85%, 90%, 95%, 96%, 97%, 98%, or 99%. Optionally, the T2R proteins or polypeptides of the assays can comprise a domain of a T2R protein, such as an extracellular domain, transmembrane region, transmembrane domain, cytoplasmic domain, ligand-binding domain, and the like. Further, as described above, the T2R protein or a domain thereof can be covalently linked to a heterologous protein to create a chimeric protein used in the assays described herein.

Modulators of T2R receptor activity are tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

1. In Vitro Binding Assays

Taste transduction can also be examined in vitro with soluble or solid state reactions, using the T2R polypeptides of the invention. In a particular embodiment, T2R ligand-binding domains can be used in vitro in soluble or solid state reactions to assay for ligand binding.

It is possible that the ligand-binding domain may be formed by the N-terminal domain together with additional portions of the extracellular domain, such as the extracellular loops of the transmembrane domain.

In vitro binding assays have been used with other GPCRs, such as the metabotropic glutamate receptors (see, e.g., Han and Hampson, J. Biol. Chem. 274:10008-10013 (1999)). These assays might involve displacing a radioactively or fluorescently labeled ligand, measuring changes in intrinsic fluorescence or changes in proteolytic susceptibility, etc.

Ligand binding to a T2R polypeptide according to the invention can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

In a preferred embodiment of the invention, a [35S]GTPγS binding assay is used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively labeled [35S]GTPγS to the G protein in the presence of a putative ligand. Typically, membranes containing the chemosensory receptor of interest are mixed with a G protein. Potential inhibitors and/or activators and [35S]GTPγS are added to the assay, and binding of [35S]GTPγS to the G protein is measured. Binding can be measured by liquid scintillation counting or by any other means known in the art, including scintillation proximity assays (SPA). In other assays formats, fluorescently labeled GTPγS can be utilized.

2. Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T2R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor taste eliciting compound-binding which may activate or inhibit the chemosensory receptors of the invention, fluorescence-labeled taste eliciting compounds or auto-fluorescent taste eliciting compounds may be used.

Fluorescence polarization (P) is defined as:

$$P = \frac{[Int_{par} - Int_{prep}]}{[Int_{par} + Int_{perp}]}$$

Where. $Int_{par}$ is the intensity of the emission light parallel to the excitation light plane and $Int_{perp}$ is the intensity of the emission light perpendicular to the excitation light plane. P, being a ratio of light intensities, is a dimensionless number. For example, the Beacon™ and Beacon 2000™. System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236-240 incorporated by reference, which gives a thorough explanation of this equation. Summarily, the Perrin equation states that polarization is directly proportional to the rotational relaxation time, the time that it takes a molecule to rotate through an angle of approximately 68.5°. Rotational relaxation time is related to viscosity (eta.), absolute temperature (T), molecular volume (V), and the gas constant (R) by the following equation:

$$2(\text{Rotational Relaxation Time})=3VRT$$

The rotational relaxation time is small (≃ nanosecond) for small molecules (e.g. fluorescein) and large (≃100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

B. A. Solid State and Soluble High Throughput Assays

In yet another embodiment, the invention provides soluble assays using a T2R polypeptide; or a cell or tissue expressing a T2R polypeptide. In another embodiment, the invention provides solid phase based in vitro assays in a high throughput format, where the T2R polypeptide, or cell or tissue expressing the T2R polypeptide is attached to a solid phase substrate or a taste stimulating compound and contacted with a T2R receptor, and binding detected using an appropriate tag or antibody raised against the T2R receptor.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc., 85:2149-2154 (1963) (describing solid phase synthesis of, e.g., peptides); Geysen et al., J. Immun. Meth., 102:259-274 (1987) (describing synthesis of solid phase components on pins); Frank & Doring, Tetrahedron, 44:60316040 (1988) (describing synthesis of various peptide sequences on cellulose disks); Fodor et al., Science, 251:767-777 (1991); Sheldon et al., Clinical Chemistry, 39(4):718-719 (1993); and Kozal et al., Nature Medicine, 2(7):753759 (1996) (all describing arrays of biopolymers fixed to solid substrates). Non-chemical approaches for fixing tag binders to substrates include other common methods, such as heat, cross-linking by UV radiation, and the like.

3. Cell-Based Assays

In one preferred embodiment, a T2R protein is expressed in a eukaryotic cell either in unmodified forms or as chimeric, variant or truncated receptors with or preferably without a heterologous, chaperone sequence that facilitates its maturation and targeting through the secretory pathway. Such T2R polypeptides can be expressed in any eukaryotic cell, such as HEK-293 cells. Preferably, the cells comprise a functional G protein, e.g., $G_{\alpha 15}$, or a chimeric $G_{\alpha 16}$, gustducin or transducin or a chimeric G protein such as G16gust44 that is capable of coupling the chimeric receptor to an intracellular signaling pathway or to a signaling protein such as phospholipase C. Activation of T2R receptors in such cells can be detected using any standard method, such as by detecting changes in intracellular calcium by detecting FURA-2 dependent fluorescence in the cell. Such an assay is the basis of the experimental findings presented in this application.

Activated GPCR receptors often are substrates for kinases that phosphorylate the C-terminal tail of the receptor (and possibly other sites as well). Thus, activators will promote the transfer of $^{32}P$ from radiolabeled ATP to the receptor, which can be assayed with a scintillation counter. The phosphorylation of the C-terminal tail will promote the binding of arrestin-like proteins and will interfere with the binding of G proteins. For a general review of GPCR signal transduction and methods of assaying signal transduction, see, e.g., Methods in Enzymology, vols. 237 and 238 (1994) and volume 96 (1983); Bourne et al., Nature, 10:349:117-27 (1991); Bourne et al., Nature, 348:125-32 (1990); Pitcher et al., Annu. Rev. Biochem., 67:653-92 (1998).

T2R modulation may be assayed by comparing the response of T2R polypeptides treated with a putative T2R modulator to the response of an untreated control sample or a sample containing a known "positive" control. Such putative T2R modulators can include molecules that either inhibit or activate T2R polypeptide activity. In one embodiment, control samples treated with a compound that activates the T2R are assigned a relative T2R activity value of 100. Inhibition of a T2R polypeptide is achieved when the T2R activity value relative to the control sample is about 90%, optionally 50%, optionally 25-0%. Activation of a T2R polypeptide is achieved when the T2R activity value relative to the control is 110%, optionally 150%, 200-500%, or 1000-2000%.

Changes in ion flux may be assessed by determining changes in ionic polarization (i.e., electrical potential) of the cell or membrane expressing a T2R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., New Engl. J. Med., 336:1575-1595 (1997)). Whole cell currents are conveniently determined using the standard. Other known assays include: radiolabeled ion flux assays and fluorescence assays using voltage-sensitive dyes (see, e.g., Vestergarrd-Bogind et al., J. Membrane Biol., 88:67-75 (1988); Gonzales & Tsien, Chem. Biol., 4:269-277 (1997); Daniel et al., J. Pharmacol. Meth., 25:185-193 (1991); Holevinsky et al., J. Membrane Biology, 137:59-70 (1994)).

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as Ca2+, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein-coupled receptors, promiscuous G proteins such as $G_{\alpha 15}$ and $G_{\alpha 16}$ can be used in the assay of choice (Wilkie et al., Proc. Nat'l Acad. Sci., 88:10049-10053 (1991)). Alternatively, other G proteins such as gustducin, transducin and chimeric G proteins such as $G\alpha 16gust44$ or Galpha16t25 may be used.

Receptor activation initiates subsequent intracellular events, e.g., increases in second messengers. Activation of some G protein-coupled receptors stimulates the formation of inositol triphosphate (IP3) through phospholipase C-mediated hydrolysis of phosphatidylinositol (Berridge & Irvine, Nature, 312:315-21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both calcium release from intracellular stores and extracellular calcium entry via plasma membrane ion channels.

In a preferred embodiment, T2R polypeptide activity is measured by expressing T2R gene in a heterologous cell with a promiscuous G protein that links the receptor to a phospholipase C signal transduction pathway (see Offermanns & Simon, J. Biol. Chem., 270:15175-15180 (1995)). Preferably, the cell line is HEK-293 (which does not normally express T2R genes) and the promiscuous G protein is $G_{\alpha 15}$ (Offermanns & Simon, supra) or a chimeric G protein such as $G\alpha 16gust44$. Modulation of taste transduction is assayed by measuring changes in intracellular $Ca^{2+}$ levels, which change in response to modulation of the T2R signal transduction pathway via administration of a molecule that associates with the T2R polypeptide. Changes in $Ca^{2+}$ levels are optionally measured using fluorescent $Ca^{2+}$ indicator dyes and fluorimetric imaging.

In another embodiment, phosphatidyl inositol (PI) hydrolysis can be analyzed according to U.S. Pat. No. 5,436, 128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

Other receptor assays can involve determining the level of intracellular cyclic nucleotides, e.g., cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. In one embodiment, the changes in intracellular cAMP or cGMP can be measured using immunoassays. The method described in Offermanns & Simon, J. Bio. Chem., 270:15175-15180 (1995), may be used to determine the level of cAMP. Also, the method described in Felley-Bosco et al., Am. J. Resp. Cell and Mol. Biol., 11:159-164 (1994), may be used to determine the level of cGMP. Further, an assay kit for measuring cAMP and/or cGMP is described in U.S. Pat. No. 4,115,538, herein incorporated by reference.

In another embodiment, transcription levels can be measured to assess the effects of a test compound on signal transduction. A host cell containing T2R polypeptide of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, luciferase, beta-galactosidase, beta-lactamase and alkaline phosphatase. Furthermore, the protein of interest can be used as an indirect reporter via attachment to a second reporter such as green fluorescent protein (see, e.g., Mistili & Spector, Nature Biotechnology, 15:961-964 (1997)).

The amount of transcription is then compared to the amount of transcription in either the same cell in the absence of the test compound, or it may be compared with the amount of transcription in a substantially identical cell that lacks the T2R polypeptide(s) of interest. A substantially identical cell may be derived from the same cells from which the recombinant cell was prepared but which had not been modified by introduction of heterologous DNA. Any difference in the amount of transcription indicates that the test compound has in some manner altered the activity of the T2R polypeptide of interest.

4. Transgenic Non-Human Animals Expressing Chemosensory Receptors

Non-human animals expressing one or more taste receptor sequences of the invention can also be used for receptor assays. Such expression can be used to determine whether a test compound specifically binds to a mammalian taste transmembrane receptor complex in vivo by contacting a non-human animal stably or transiently transfected with nucleic acids encoding chemosensory receptors or ligand-binding regions thereof with a test compound and determining whether the animal reacts to the test compound by specifically binding to the receptor polypeptide complex.

Animals transfected or infected with the vectors of the invention are particularly useful for assays to identify and characterize taste stimuli that can bind to a specific or sets of receptors. Such vector-infected animals expressing human taste receptor sequences can be used for in vivo screening of taste stimuli and their effect on, e.g., cell physiology (e.g., on taste neurons), on the CNS, or behavior.

Means to infect/express the nucleic acids and vectors, either individually or as libraries, are well known in the art. A variety of individual cell, organ, or whole animal parameters can be measured by a variety of means. The T2R sequences of the invention can be for example expressed in animal taste tissues by delivery with an infecting agent, e.g., adenovirus expression vector.

The endogenous taste receptor genes can remain functional and wild-type (native) activity can still be present. In other situations, where it is desirable that all taste receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, Transgenic Res 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, Hum. Mol. Genet. 7:53-62 (1998); Moreadith, J. Mol. Med. 75:208-216 (1997); Tojo, Cytotechnology 19:161-165 (1995); Mudgett, Methods Mol. Biol. 48:167-184 (1995); Longo, Transgenic Res. 6:321-328 (1997); U.S. Pat. Nos. 5,616,491; 5,464,764; 5,631,153; 5,487,992; 5,627,059; 5,272,071; WO 91/09955; WO 93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T2R gene sequences can replace the orthologs T2R in the mouse genome. In this way, a mouse expressing a human or rat T2R is produced. This mouse can then be used to analyze the function of human or rat T2Rs, and to identify ligands for such T2Rs.

Modulators

The compounds tested as modulators of a T2R family member can be any small chemical compound, or a biological entity, such as a protein, sugar, nucleic acid or lipid. Alternatively, modulators can be genetically altered versions of a T2R family member. Typically, test compounds may be small chemical molecules and peptides. Essentially any chemical compound can be used as a potential modulator or ligand in the assays of the invention, although most often compounds can be dissolved in aqueous or organic (especially DMSO-based) solutions are used. The assays may be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual consumer products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res., 37:487-93 (1991) and Houghton et al., Nature, 354:84-88 (1991)). Other chemistries for generating chemical diversity libraries can also be used. Such chemistries include, but are not limited to: peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs et al., PNAS., 90:6909-13 (1993)), vinylogous polypeptides (Hagihara et al., J. Amer. Chem. Soc., 114:6568 (1992)), nonpeptidal peptidomimetics with glucose scaffolding (Hirschmann et al., J. Amer. Chem. Soc., 114:9217-18 (1992)), analogous organic syntheses of small compound libraries (Chen et al., J. Amer. Chem. Soc., 116:2661 (1994)), oligocarbamates (Cho et al., Science, 261:1303 (1993)), peptidyl phosphonates (Campbell et al., J. Org. Chem., 59:658 (1994)), nucleic acid libraries (Ausubel, Berger, and Sambrook, all supra), peptide nucleic acid libraries (U.S. Pat. No. 5,539,083), antibody libraries (Vaughn et al., Nature Biotechnology, 14(3):309-14 (1996) and PCT/US96/10287), carbohydrate libraries (Liang et al., Science, 274:1520-22 (1996) and U.S. Pat. No. 5,593, 853), small organic molecule libraries (benzodiazepines, Baum, C&EN, January 18, page 33 (1993); thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T2R modulators can be used in any food product, confectionery, pharmaceutical composition, or ingredient thereof to thereby modulate the taste of the product, composition, or ingredient in a desired manner. For instance, T2R modulators that enhance bitter taste sensation can be added to provide a bitter taste to a product or composition, while T2R modulators which block bitter taste sensations can be added to block the bitter taste of a product or composition. Also, the invention provides means of identifying bitter compounds found in foods, beverages and medicinals and producing taste improved foods, beverages and medicinals lacking or having a reduced quantity thereof.

Use of Compounds Identified by the Invention

Compounds identified according to the invention may be added to foods, beverages, cosmetics or medicinal compositions to modulate, preferably block bitter taste triggered by activation at least one of one of hT2R1, hT2R3, hT2R4, hT2R5, hT2R7, hT2R8, hT2R9A, hT2R9V, hT2R10, hT2R13, hT2R14, hT2R16, hT2R44, hT2R44, hT2R54, hT2R55, hT2R61, hT2R64, hT2R65, hT2R67, hT2R71, hT2R75 and hT2R76, and hT2R54 by at least one of the bitter compounds contained in FIG. 2 or structurally related compounds or other bitter compounds, e.g., compounds found in foods and beverages or medicinals or cosmetics that elicit a bitter taste perception.

As noted previously, preferably, the taste modulatory properties, preferably bitter taste blocking properties of compounds identified in the subject T2R cell-based assays will be confirmed in human or animal taste tests, preferably human taste tests.

Kits

T2R genes and their homologs are useful tools for identifying taste receptor cells, for forensics and paternity determinations, and for examining taste transduction. T2R family member-specific reagents that specifically hybridize to T2R nucleic acids, such as T2R probes and primers, and T2R specific reagents that specifically bind to a T2R protein, e.g., T2R antibodies are used to examine taste cell expression and taste transduction regulation.

Nucleic acid assays for the presence of DNA and RNA for a T2R family member in a sample include numerous techniques are known to those skilled in the art, such as southern analysis, northern analysis, dot blots, RNase protection, S1 analysis, amplification techniques such as PCR, and in situ hybridization. In situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., Biotechniques, 4:230250 (1986); Haase et al., Methods in Virology, vol. VII, 189-226 (1984); and Names et al., eds., Nucleic Acid Hybridization: A Practical Approach (1987). In addition, a T2R protein can be detected with the various immunoassay techniques described above. The test sample is typically compared to both a positive control (e.g., a sample expressing a recombinant T2R protein) and a negative control.

The present invention also provides for kits for screening for modulators of T2R family members. Such kits can be prepared from readily available materials and reagents. For example, such kits can comprise any one or more of the following materials: T2R nucleic acids or proteins, reaction tubes, and instructions for testing T2R activity. Optionally, the kit contains a functional T2R polypeptide. A wide variety of kits and components can be prepared according to the present invention, depending upon the intended user of the kit and the particular needs of the user.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Example 1

In this example, HEK-293 cells were produced that stably or transiently express one of hT2R1, hT2R3, hT2R4, hT2R5, hT2R7, hT2R8, hT2R9, hT2R10, hT2R13, hT2R14, hT2R16, hT2R44, hT2R50, hT2R51, hT2R54, hT2R55, hT2R61, hT2R64, hT2R65, hT2R67, hT2R71, hT2R75 and hT2R76 and a chimeric G protein that couples therewith (sequences for these hT2Rs and chimeric G protein are contained in the Sequence Listing preceding the claims) and these cells were screened against different bitter ligands to identify compounds that specifically activate each of these bitter taste receptors.

More specifically, activation of these receptors by different bitter ligands is measured in a cell-based assay detecting changes in intracellular calcium concentration. In brief, human embryonic kidney cells are seeded into 48-well tissue culture plates. 24 hours later these seeded HEK-293 cells are transiently transfected with an expression plasmid (pEAK10) containing a sequence encoding a chimeric G protein (G16gust44) (SEQ ID NO:2) and are also are transiently transfected with a pEAK10 expression plasmid containing a particular hT2R nucleic acid sequence either by $Ca^{2+}$ phosphate or lipid-based systems. Additionally, the hT2R sequences contained in the pEAK10 plasmid are each engineered to contain a Rho-35 tag or a SSTR-3 tag upstream of the hT2R sequence and therefor express an N-terminal tag of 35 amino acids of the rhodopsin protein (SEQ ID NO:1) or of 45 amino acids of SSTR-3 protein.

After another 24 hours the transiently transfected cells are incubated with a fluorescent dye specific for calcium (Fluo-4; Molecular Probes). These loaded cells are then exposed to different bitter molecules. Activation of the hT2R by a bitter ligand results in the activation of G16gust44, which leads to calcium mobilization within the cells. Thereupon this change in intracellular calcium causes the fluorescent dye to emit a detectable change in the fluorescence which is monitored using fluorescence microscopy. Particularly, this increase in calcium concentration changes the fluorescence properties of the calcium dye inside the cells and these changes are monitored using fluorescence microscopy and a specifically designed software (Imaging Workbench, Axon).

Also, the assay can be performed with the automated fluorimetric imaging system (FLIPR) using a slightly different protocol. In this protocol an HEK293 cell line stably expressing G16gust44 was transfected with an hT2R expression plasmid and 24 hours later the cells are dye loaded and analyzed on FLIPR.

Additionally, once a ligand is identified for a particular hT2R using this approach, a HEK-293 cell line is generated that stably expresses the particular hT2R and the chimeric G protein G16gust44 thereby A large number of bitter ligands were assayed against the above-identified hT2Rs at the concentrations set forth therein. The results of these assays for each of the hT2Rs are summarized in FIG. 2. It can be seen that each of the tested hT2Rs was found to be specifically activated by at least one bitter ligand. As can be seen from the tabulated results, typically, a particular hT2R responds to a number of different bitter ligands having divergent structures. Also the results in FIG. 2 show that many of the bitter ligands specifically activate more than one hT2R. The concentrations used for these bitter ligands are contained in FIG. 3.

Example 2 hT2R9 Allelic Variants and Assays

The deorphaning of hT2R9 and of other human T2R is reported in the previous example. This example relates specifically to the hT2R9 sequences contained in Sequence in the Sequence Listing that precedes the claims herein. With respect thereto it has been reported by Kim et al (Hum Mutat. 2005 September; 26:199-204) that there are 2 haplotypes of hT2R9. The protein and DNA sequences of both T2R9 haplotypes (hT2R9A and hT2R9V) are contained in SEQ ID NO: 13-16 in the Sequence Listing. The one we refer to as hT2R9V, appears to be a non-functional allele with the bitter ligands tested, while the other allele, hT2R9A, is functional with tested bitter ligands. The 2 alleles differ by one amino acid residue at amino acid position 187, while hT2R9A contains an Ala residue, hT2R9V instead contains a Val residue. According to Kim et al (Hum Mutat. 2005 September; 26:199-204), those 2 haplotypes represent about 91% of the human population (hT2R9V 55.5%, and hT2R9A 35.5%).

As described in the foregoing example 23 different human taste receptors were successfully deorphaned including hT2R9. The 2 major haplotypes of hT2R9 are referred to here as hT2R9V and hT2R9A. The nucleic and amino acid sequences corresponding thereto are contained in the Sequence Listing that precedes the claims.

The hT2R9V sequence was initially cloned. Thereafter, hT2R9A sequence was cloned and both were expressed using a Rho-tagged expression vector and the same HEK-293 cell-based assays for identifying T2R9 ligands. Both of these hT2R9 sequences were evaluated in these assays using the same ligands. It was observed that hT2R9A demonstrated activity when contacted with ofloxacin whereas hT2R9V or mock-transfected HEK-293 cells did not under the same assay conditions (See FIG. 4).

In addition the same T2R9 sequences were assayed using a different expression construct containing a SSTR3 tag. (Bufe et al., Nat. Genet. 32:397-400 (2002)). These results generated the dose-dependent curves contained in FIG. 5 using transiently transfected cells and FLIPR. These results were in accord with the previous experiment and suggest that hT2R9A is functional, i.e., it responds to specific bitter ligands whereas hT2R9V does not respond to the same bitter ligands. As noted above, T2Rs and T1Rs are both known to be expressed in gastrointestinal cells and are believed to potentially play a role in digestive and metabolic functions and diseases. Therefore, either or both of these T2R9 alleles may be useful in therapeutic screening assays. Also, such allelic variation in hT2R sequences including hT2R9 may be involved in the disparate responses to bitter ligands in some individuals, e.g., between the group of people carrying hT2R9A versus the group who are homozygous for the hT2R9V allele.

---

(a) SEQUENCES OF CHIMERIC G PROTEIN AND hT2R GENES AND POLYPEPTIDES

---

```
Protein Sequence of the Rhodopsin tag: (SEQ ID NO: 1)
MNGTEGPNFYVPFSNKTGVVRSPFEAPQYYLAEPW Protein Sequence of G16gust44: (SEQ ID NO: 2)
MARSLTWRCCPWCLTEDEKAAARVDQEINRILLEQKKQDRGELKLLLLGPGESGKSTFIKQMRIIHGAGYSEEERKGFRPLVYQNI
FVSMRAMIEAMERLQIPFSRPESKHHASLVMSQDPYKVTTFEKRYAAAMQWLWRDAGIRACYERRREFHLLDSAVYYLSHLERITE
EGYVPTAQDVLRSRMPTTGINEYCFSVQKTNLRIVDVGGQKSERKKWIHCFENVIALIYLASLSEYDQCLEENNQENRMKESLALF
GTILELPWFKSTSVILFLNKTDILEEKIPTSHLATYFPSFQGPKQDAEAAKRFILDMYTRNYTGCVDGPEGSNLKKEDKEIYSHMT
CATDTQNVKFVFDAVTDIIIKENLKDCGLF hT2R1 sequences
DNA-(SEQ ID NO: 3)
ATGCTAGAGTCTCACCTCATTATCTATTTTCTTCTTGCAGTGATACAATTTCTTCTTGGGATTTTCACAAATGGCATCAT
TGTGGTGGTGAATGGCATTGACTTGATCAAGCACAGAAAAATGGCTCCGCTGGATCTCCTTCTTTCTTGTCTGGCAGTTT
CTAGAATTTTTCTGCAGTTGTTCATCTTCTACGTTAATGTGATTGTTATCTTCTTCATAGAATTCATCATGTGTTCTGCG
AATTGTGCAATTCTCTTATTTATCAATGAATTGGAACTTTGGCTTGCCACATGGCTCGGCGTTTTCTATTGTGCCAAGGT
TGCCAGCGTCCGTCACCCACTCTTCATCTGGTTGAAGATGAGGATATCCAAGCTGGTCCCATGGATGATCCTGGGGTCTC
TGCTATATGTATCTATGATTTGTGTTTTCCATAGCAAATATGCAGGGTTTATGGTCCCATACTTCCTAAGGAAATTTTTC
TCCCAAAATGCCACAATTCAAAAAGAAGATACACTGGCTATACAGATTTTCTCTTTTGTTGCTGAGTTCTCAGTGCCATT
GCTTATCTTCCTTTTTGCTGTTTTGCTCTTGATTTTCTCTCTGGGGAGGCACACCCGGCAAATGAGAAACACAGTGGCCG
GCAGCAGGGTTCCTGGCAGGGGTGCACCCATCAGCGCGTTGCTGTCTATCCTGTCCTTCCTGATCCTCTACTTCTCCCAC
TGCATGATAAAAGTTTTTCTCTCTTCTCTAAAGTTTCACATCAGAAGGTTCATCTTTCTGTTCTTCATCCTTGTGATTGG
TATATACCCTTCTGGACACTCTCTCATCTTAATTTTAGGAAATCCTAAATTGAAACAAAATGCAAAAAAGTTCCTCCTCC
ACAGTAAGTGCTGTCAGTGA Protein-(SEQ ID NO: 4)
MLESHLIIYFLLAVIQFLLGIFTNGIIVVVNGIDLIKHRKMAPLDLLLSCLAVSRIFLQLFIFYVNVIVIFFIEFIMCSA
NCAILLFINELELWLATWLGVFYCAKVASVRHPLFIWLKMRISKLVPWMILGSLLYVSMICVFHSKYAGFMVPYFLRKFF
SQNATIQKEDTLAIQIFSFVAEFSVPLLIFLFAVLLLIFSLGRHTRQMRNTVAGSRVPGRGAPISALLSILSFLILYFSH
CMIKVFLSSLKFHIRRFIFLFFILVIGIYPSGHSLILILGNPKLKQNAKKFLLHSKCCQ hT2R3 sequences
DNA-(SEQ ID NO: 5)
ATGATGGGACTCACCGAGGGGGTGTTCCTGATTCTGTCTGGCACTCAGTTCACACTGGGAATTCTGGTCAATTGTTTCAT
TGAGTTGGTCAATGGTAGCAGCTGGTTCAAGACCAAGAGAATGTCTTTGTCTGACTTCATCATCACCACCCTGGCACTCT
TGAGGATCATTCTGCTGTGTATTATCTTGACTGATAGTTTTTAATAGAATTCTCTCCCAACACACATGATTCAGGGATA
ATAATGCAAATTATTGATGTTTCCTGGACATTTACAAACCATCTGAGCATTTGGCTTGCCACCTGTCTTGGTGTCCTCTA
CTGCCTGAAAATCGCCAGTTTCTCTCACCCCACATTCCTCTGGCTCAAGTGGAGAGTTTCTAGGGTGATGGTATGGATGC
TGTTGGGTGCACTGCTCTTATCCTGTGGTAGTACCGCATCTCTGATCAATGAGTTTAAGCTCTATTCTGTCTTTAGGGGA
ATTGAGGCCACCAGGAATGTGACTGAACACTTCAGAAAGAAGAGGAGTGAGTATTATCTGATCCATGTTCTTGGGACTCT
GTGGTACCTGCCCTCCCTTAATTGTGTCCCTGGCCTCCTACTCTTTGCTCATCTTCTCCCTGGGGAGGCACACACGGCAGA
```

| (a) SEQUENCES OF CHIMERIC G PROTEIN AND hT2R GENES AND POLYPEPTIDES |
|---|

```
TGCTGCAAAATGGGACAAGCTCCAGAGATCCAACCACTGAGGCCCACAAGAGGGCCATCAGAATCATCCTTTCCTTCTTC
TTTCTCTTCTTACTTTACTTTCTTGCTTTCTTAATTGCATCATTTGGTAATTTCCTACCAAAAACCAAGATGGCTAAGAT
GATTGGCGAAGTAATGACAATGTTTTATCCTGCTGGCCACTCATTTATTCTCATTCTGGGGAACAGTAAGCTGAAGCAGA
CATTTGTAGTGATGCTCCGGTGTGAGTCTGGTCATCTGAAGCCTGGATCCAAGGGACCCATTTTCTCTTAG

Protein-
MMGLTEGVFLILSGTQFTLGILVNCFIELVNGSSWFKTKRMSLSDFIITTLALLRIILLCIILTDSFLIEFSPNTHDSGI
IMQIIDVSWTFTNHLSIWLATCLGVLYCLKIASFSHPTFLWLKWRVSRVMVWMLLGALLLSCGSTASLINEFKLYSVFRG
IEATRNVTEHFRKKRSEYYLIHVLGTLWYLPPLIVSLASYSLLIFSLGRHTRQMLQNGTSSRDPTTEAHKRAIRIILSFF
FLFLLYFLAFLIASFGNFLPKTKMAKMIGEVMTMFYPAGHSFILILGNSKLKQTFVVMLRCESGHLKPGSKGPIFS hT2R4 sequences:
DNA-(SEQ ID NO: 5)
ATGCTTCGGTTATTCTATTTCTCTGCTATTATTGCCTCAGTTATTTTAAATTTTGTAGGAATCATTATGAATCTGTTTAT
TACAGTGGTCAATTGCAAAACTTGGGTCAAAAGCCATAGAATCTCCTCTTCTGATAGGATTCTGTTCAGCCTGGGCATCA
CCAGGTTTCTTATGCTGGGACTATTTCTGGTGAACACCATCTACTTCGTCTTCAAATACGGAAAGGTCAGTCTACCTG
TCTGCTTTTTTTGTGTTGTGTTTCATGTTTTTGGACTCGAGCAGTGTCTGGTTTGTGACCcTGCTCAATATCTTGTACTG
TGTGAAGATTACTAACTTCCAACACTCAGTGTTTCTCCTGCTGAAGCGGAATATCTCCCAAAGATCCCCAGGCTGCTGC
TGGCCTGTGTGCTGATTCTGCTTTCACCCACTTGCCTGTACATCACGCTTAGCCAGGCATCACCTTTTCCTGAACTTGTG
ACTACGAGAAATAACACATCATTTAATATCAGTGAGGGCATCTTGTCTTTAGTGGTTTCTTTGGTCTTGAGCTCATCTCT
CCAGTTCATCATTAATGTGACTTCTGCTTCCTTGCTAATACACTCCTGAGGAGACATATACAGAAGATGCAGAAAAATG
CCACTGGTTTCTGGAATCCCCAGACGGAAGCTCATGTAGGTGCTATGAAGCTGATGGTCTATTTCCTCATCCTCTACATT
CCATATTCAGTTGCTACCCTGGTCCAGTATCTCCCCTTTTATGCAGGGATGGATATGGGGACCAAATCCATTTGTCTGAT
TTTTGCCACCCTTTACTCTCCAGGACATTCTGTTCATTATTATCACACATCCTAAACTGAAAACAACAGCAAAGAAGA
TTCTTTGTTTCAAAAAATAG Protein-(SEQ ID NO: 6)
MLRLFYFSAIIASVILNFVGIIMNLFITVVNCKTWVKSHRISSSDRILFSLGITRFLMLGLFLVNTIYFVSSNTERSVYL
SAFFVLCFMFLDSSSVWFVTLLNILYCVKITNFQHSVFLLLKRNISPKIPRLLLACVLISAFTTCLYITLSQASPFPELV
TTRNNTSFNISEGILSLVVSLVLSSSLQFIINVTSASLLIHSLRRHIQKMQKNATGFWNPQTEAHVGAMKLMVYFLILYI
PYSVATLVQYLPFYAGMDMGTKSICLIFATLYSPGHSVLIIITHPKLKTTAKKILCFKK hT2R5 sequences:
DNA-(SEQ ID NO: 7)
ATGCTGAGCGCTGGCCTAGGACTGCTGATGCTGGTGGCAGTGGTTGAATTTCTCATCGGTTTAATTGGAAATGGAATCCT
GGTGGTCTGGAGTTTTAGAGAATGGATCAGAAAATTCAACTGGTCCTCATATAACCTCATTATCCTGGGCCTGGCTGGCT
GCCGATTTCTCCTGCAGTGGCTGATCATTTTGGACTTAAGCTTGTTTCCAGAGCAGCCGTTGGCTTCGCTAT
CTTAGTATCTTCTGGGTCCTGGTAAGCCAGGCCAGCTTATGGTTTGCCACCTTCCTCAGTGTCTTCTATTGCAAGAAGAT
CACGACCTTCGATCGCCCGGCCTACTTGTGGCTGAAGCAGAGGGCCTATAACCTGAGTCTCTGGTGCCTTCTGGGCTACT
TTATAATCAATTTGTTACTTACAGTCCAAATTGGCTTAACATTCTATCATCCTCCCAAGGAAACAGCAGCATTCGGTAT
CCCTTTGAAAGCTGGCAGTACCTGTATGCATTTCAGCTCAATTCAGGAAGTTATTTGCCTTTAGTGGTGTTTCTTGTTTC
CTCTGGGATGCTCATTGTCTCTTTGTATACACACCACCAAGAAGATGAAGGTCCATTCAGCTGGTAGGAGGGATGTCCGGG
CCAAGGCTCACATCACTGCGCTGAAGTCCTTGGGCTGCTTCCTCTTACTTCACCTGGTTTATATCATGGCCAGCCCCTTC
TCCATCACCTCCAAGACTTATCCTCCTGATCTCACCAGTGTCTTCATCTGGGAGACACTCATGGCAGCCTATCCTTCTCT
TCATTCTCTCATATTGATCATGGGGATTCCTAGGGTGAAGCAGACTTGTCAGAAGATCCTGTGGAAGACAGTGTGTGCTC
GGAGATGCTGGGGCCCATGA Protein-(SEQ ID NO: 8)
MLSAGLGLLMLVAVVEFLIGLIGNGILVVWSFREWIRKFNWSSYNLIILGLAGCRFLLQWLIILDLSLFPLFQSSRWLRY
LSIFWVLVSQASLWFATFLSVFYCKKITTFDRPAYLWLKQRAYNLSLWCLLGYFIINLLLTVQIGLTFYHPPQGNSSIRY
PFESWQYLYAFQLNSGSYLPLVVFLVSSGMLIVSLYTHHKKMKVHSAGRRDVRAKAHITALKSLGCFLLLHLVYIMASPF
SITSKTYPPDLTSVFIWETLMAAYPSLHSLILIMGIPRVKQTCQKILWKTVCARRCWGP hT2R7 sequences:
DNA-(SEQ ID NO: 9)
ATGGCAGATAAAGTGCAGACTACTTTATTGTTCTTAGCAGTTGGAGAGTTTTCAGTGGGGATCTTAGGGAATGCATTCAT
TGGATTGGTAAACTGCATGGACTGGGTCAAGAAGAGGAAAATTGCCTCCATTGATTTAATCCTCACAAGTCTGGCCATAT
CCAGAATTTGTCTATTGTGCGTAATACTATTAGATTGTTTTATATTGGTGCTATATCCAGATGTCTATGCCACTGGTAAA
GAAATGAGAATCATTGACTTCTTCTGGACACTAACCAATCATTTAAGTATCTGGTTTGCAACCTGCCTCAGCATTTACTA
TTTCTTCAAGATAGGTAATTTCTTTCACCCACTTTTCCTCTGGATGAAGTGGAGAATTGACAGGGTGATTTCCTGGATTC
TACTGGGTGCGTGGTTCTCTCTGTGTTTATTAGCCTTCCAGCCACTGAGAATTTGAACGCTGATTTCAGGTTTTGTGTG
AAGGCAAAGAGGAAAACAAACTTAACTTGGAGTTGCAGAGTAAATAAACTCAACATGCTTCTACCAAGTTATTTCTCAA
CCTGGCAACGCTGCTCCCCTTTTGTGTGTGCCTAATGTCCTTTTTCCTCTTGATCCTCTCCCTGCGGAGACATATCAGGC
GAATGCAGCTCAGTGCCACAGGGTGCAGAGACCCCAGCACAGAAGCCATGTGAGAGCCCTGAAAGCTGTCATTTCCTTC
CTTCTCCTCTTTATTGCCTACTATTTGTCCTTTCTCATTGCCACCTCCAGCTACTTTATGCCAGAGACGGAATTAGCTGT
GATTTTTGGTGAGTCCATAGCTCTAATCTACCCCTCAAGTCATTCATTTATCCTAATACTGGGGAACAATAAATTAAGAC
ATGCATCTCTAAAGGTGATTTGGAAAGTAATGTCTATTCTAAAAGGAAGAAAATTCCAACAACATAAACAAATCTGA Protein-(SEQ ID NO: 10)
MADKVQTTLLFLAVGEFSVGILGNAFIGLVNCMDWVKKRKIASIDLILTSLAISRICLLCVILLDCFILVLYPDVYATGK
EMRIIDFFWTLTNHLSIWFATCLSIYYFFKIGNFFHPLFLWMKWRIDRVISWILLGCVVLSVFISLPATENLNADFRFCV
KAKRKTNLTWSCRVNKTQHASTKLFLNLATLLPFCVCLMSFFLLILSLRRHIRRMQLSATGCRDPSTEAHVRALKAVISF
LLLFIAYYLSFLIATSSYFMPETELAVIFGESIALIYPSSHSFILILGNNKLRHASLKVIWKVMSILKGRKFQQHKQI
```

| (a) SEQUENCES OF CHIMERIC G PROTEIN AND hT2R GENES AND POLYPEPTIDES |
|---| hT2R8 sequences:
DNA-(SEQ ID NO: 11)
ATGTTCAGTCCTGCAGATAACATCTTTATAATCCTAATAACTGGAGAATTCATACTAGGAATATTGGGGAATGGATACAT
TGCACTAGTCAACTGGATTGACTGGATTAAGAAGAAAAAGATTTCCACAGTTGACTACATCCTTACCAATTTAGTTATCG
CCAGAATTTGTTTGATCAGTGTAATGGTTGTAAATGGCATTGTAATAGTACTGAACCCAGATGTTTATACAAAAAATAAA
CAACAGATAGTCATTTTTACCTTCTGGACATTTGCCAACTACTTAAATATGTGGATTACCACCTGCCTTAATGTCTTCTA
TTTTCTGAAGATAGCCAGTTCCTCTCATCCACTTTTTCTCTGGCTGAAGTGGAAAATTGATATGGTGGTGCACTGGATCC
TGCTGGGATGCTTTGCCATTTCCTTGTTGGTCAGCCTTATAGCAGCAATAGTACTGAGTTGTGATTATAGGTTTCATGCA
ATTGCCAAACATAAAAGAAACATTACTGAAATGTTCCATGTGAGTAAAATACCATACTTTGAACCCTtaACTCTCTTTAA
CCTGTTTGCAATTGTCCCATTTATTGTGTCACTGATATCATTTTTCCTTTTAGTAAGATCTTTATGGAGACATACCAAGC
AAATAAAACTCTATGCTACCGGCAGTAGAGACCCCAGCACAGAAGTTCATGTGAGAGCCATTAAAACTATGACTTCATTT
ATCTTCTTTTTTTTCCTATACTATATTTCTTCTATTTTGATGACCTTTAGCTATCTTATGACAAAATACAAGTTAGCTGT
GGAGTTTGGAGAGATTGCAGCAATTCTCTACCCCTTGGGTCACTCACTTATTTTAATTGTTTTAAATAATAAACTGAGGC
AGACATTTGTCAGAATGCTGACATGTAGAAAAATTGCCTGCATGATATGA Protein-(SEQ ID NO: 12)
MFSPADNIFIILITGEFILGILGNGYIALVNWIDWIKKKKISTVDYILTNLVIARICLISVMVVNGIVIVLNPDVYTKNK
QQIVIFTFWTFANYLNMWITTCLNVFYFLKIASSSHPLFLWLKWKIDMVVHWILLGCFAISLLVSLIAAIVLSCDYRFHA
IAKHKRNITEMFHVSKIPYFEPLTLFNLFAIVPFIVSLISFFLLVRSLWRHTKQIKLYATGSRDPSTEVHVRAIKTMTSF
IFFFLYYISSILMTFSYLMTKYKLAVEFGEIAAILYPLGHSLILIVLNNKLRQTFVRMLTCRKIACMI hT2R9 sequences:
hT2R9V
cDNA-(SEQ ID NO: 13)
ATGCCAAGTGCAATAGAGGCAATATATATTATTTTAATTGCTGGTGAATTGACCATAGGGATTTGGGGAAATGGATTCAT
TGTACTAGTTAACTGCATTGACTGGCTCAAAAGAAGAGATATTTCCTTGATTGACATCATCCTGATCAGCTTGGCCATCT
CCAGAATCTGTCTGCTGTGTGTAATATCATTAGATGGCTTCTTTATGCTGCTCTTTCCAGGTACATATGGCAATAGCGTG
CTAGTAAGCATTGTGAATGTTGTCTGGACATTTGCCAATAATTCAAGTCTCTGGTTTACTTCTTGCCTCAGTATCTTCTA
TTTACTCAAGATAGCCAATATATCGCACCCATTTTTCTTCTGGCTGAAGCTAAAGATCAACAAGGTCATGCTTGCGATTC
TTCTGGGGTCCTTTCTTATCTCTTTAATTATTAGTGTTCCAAAGAATGATGATATGTGGTATCACCTTTTCAAAGTCAGT
CATGAAGAAAACATTACTTGGAAATTCAAAGTGAGTAAAATTCCAGGTACTTTCAAACAGTTAACCCTGAACCTGGGGGT
GATGGTTCCCTTTATCCTTTGCCTGATCTCATTTTTCTTGTTACTTTTCTCCCTAGTTAGACACACCAAGGAGATTCGAC
TGCATGCTACAGGGTTCAGAGACCCCAGTACAGAGGCCCACATGAGGGCCATAAAGGCAGTGATCATCTTTCTGCTCCTC
CTCATCGTGTACTACCCAGTCTTTCTTGTTATGACCTCTAGCGCTCTGATTCCTCAGGGAAAATTAGTGTTGATGATTGG
TGACATAGTAACTGTCATTTTCCCATCAAGCCATTCATTCATTCTAATTATGGGAAATAGCAAGTTGAGGGAAGCTTTTC
TGAAGATGTTAAGATTTGTGAAGTGTTTCCTTAGAAGAAGAAAGCCTTTTGTTCCATAG Protein (SEQ ID NO: 14)
MPSAIEAIYIILIAGELTIGIWGNGFIVLVNCIDWLKRRDISLIDIILISLAISRICLLCVISLDGFFMLLFPGTYGNSV
LVSIVNVVWTFANNSSLWFTSCLSIFYLLKIANISHPFFFWLKLKINKVMLAILLGSFLISLIISVPKNDDMWYHLFKVS
HEENITWKFKVSKIPGTFKQLTLNLGVMVPFILCLISFFLLLFSLVRHTKQRLHATGFRDPSTEAHMRAIKAVIIFLLL
LIVYYPVFLVMTSSALIPQGKLVLMIGDIVTVIFTSSHSFILIMGNSKLREAFLKMLRFVKCFLRRRKPFVP hT2R9A
cDNA-(SEQ ID NO: 15)
ATGCCAAGTGCAATAGAGGCAATATATATTATTTTAATTGCTGGTGAATTGACCATAGGGATTTGGGGAAATGGATTCAT
TGTACTAGTTAACTGCATTGACTGGCTCAAAAGAAGAGATATTTCCTTGATTGACATCATCCTGATCAGCTTGGCCATCT
CCAGAATCTGTCTGCTGTGTGTAATATCATTAGATGGCTTCTTTATGCTGCTCTTTCCAGGTACATATGGCAATAGCGTG
CTAGTAAGCATTGTGAATGTTGTCTGGACATTTGCCAATAATTCAAGTCTCTGGTTTACTTCTTGCCTCAGTATCTTCTA
TTTACTCAAGATAGCCAATATATCGCACCCATTTTTCTTCTGGCTGAAGCTAAAGATCAACAAGGTCATGCTTGCGATTC
TTCTGGGGTCCTTTCTTATCTCTTTAATTATTAGTGTTCCAAAGAATGATGATATGTGGTATCACCTTTTCAAAGTCAGT
CATGAAGAAAACATTACTTGGAAATTCAAAGTGAGTAAAATTCCAGGTACTTTCAAACAGTTAACCCTGAACCTGGGGGC
GATGGTTCCCTTTATCCTTTGCCTGATCTCATTTTTCTTGTTACTTTTCTCCCTAGTTAGACACACCAAGCAGATTCGAC
TGCATGCTACAGGGTTCAGAGACCCCAGTACAGAGGCCCACATGAGGGCCATAAAGGCAGTGATCATCTTTCTGCTCCTC
CTCATCGTGTACTACCCAGTCTTTCTTGTTATGACCTCTAGCGCTCTGATTCCTCAGGGAAAATTAGTGTTGATGATTGG
TGACATAGTAACTGTCATTTTCCCATCAAGCCATTCATTCATTCTAATTATGGGAAATAGCAAGTTGAGGGAAGCTTTTC
TGAAGATGTTAAGATTTGTGAAGTGTTTCCTTAGAAGAAGAAAGCCTTTTGTTCCATAG Protein-(SEQ ID NO: 16)
MPSAIEAIYIILIAGELTIGIWGNGFIVLVNCIDWLKRRDISLIDIILISLAISRICLLCVISLDGFFMLLFPGTYGNSV
LVSIVNVVWTFANNSSLWFTSCLSIFYLLKIANISHPFFFWLKLKINKVMLAILLGSFLISLIISVPKNDDMWYHLFKVS
HEENITWKFKVSKIPGTFKQLTLNLGVMAPFILCLISFFLLLFSLVRHTKQIRLHATGFRDPSTEAHMRAIKAVIIFLLL
LIVYYPVFLVMTSSALIPQGKLVLMIGDIVTVIFPSSHSFILIMGNSKLREAFLKMLRFVKCFLRRRKPFVP hT2R10 sequences:
DNA-(SEQ ID NO: 17)
ATGCTACGTGTAGTGGAAGGCATCTTCATTTTTGTTGTAGTTAGTGAGTCAGTGTTTGGGGTTTTGGGGAATGGATTTAT
TGGACTTGTAAACTGCATTGACTGTGCCAAGAATAAGTTATCTACGATTGGCTTTATTCTCACCGGCTTAGCTATTTCAA
GAATTTTCTGATATGGATAATAATTACAGATGGATTTATACAGATATTCTCTCCAAATATATATGCCTCCGGTAACCTA
ATTGAATATATTAGTTACTTTGGGTAATTGGTAATCAATCAAGTATGTGGTTTGCCACCAGCCTCAGCATCTTCTATTT
CCTGAAGATAGCAAATTTTTCCAACTACATATTTCTCTGGTTGAAGAGCAGAACAAATATGGTTCTTCCCTTCATGATAG
TATTCTTACTTATTTCATCGTTACTTAATTTTGCATACATTGCGAAGATTCTTAATGATTATAAAACGAAGAATGACACA
GTCTGGGATCTCAACATGTATAAAAGTGAATACTTTATcAAgCAGATTTTGCTAAATCTGGGAGTCATTTTCTTCTTTAC
ACTATCCCTAATTACATGTATTTTTTTAATCATTTCCCTTTGGAGACACAACAGGCAGATGCAATCGAATGTGACAGGAT
TGAGAGACTCCAACACAGAAGCTCATGTGAAGGCAATGAAAGTTTTGATATCTTTCATCATCCTCTTTATCTTGTATTTT

(a) SEQUENCES OF CHIMERIC G PROTEIN AND hT2R GENES AND POLYPEPTIDES

ATAGGCATGGCCATAGAAATATCATGTTTTACTGTGCGAGAAAACAAACTGCTGCTTATGTTTGGAATGACAACCACAGC
CATCTATCCCTGGGGTCACTCATTTATCTTAATTCTAGGAAACAGCAAGCTAAAGCAAGCCTCTTTGAGGGTACTGCAGC
AATTGAAGTGCTGTGAGAAAAGGAAAAATCTCAGAGTCACATAG

Protein-(SEQ ID NO: 18)
MLRVVEGIFIFVVVSESVFGVLGNGFIGLVNCIDCAKNKLSTIGFILTGLAISRIFLIWIIITDGFIQIFSPNIYASGNL
IEYISYFWVIGNQSSMWFATSLSIFYFLKIANFSNYIFLWLKSRTNMVLPFMIVFLLISSLLNFAYIAKILNDYKTKNDT
VWDLNMYKSEYFIKQILLNLGVIFFFTLSLITCIFLIISLWRHNRQMQSNVTGLRDSNTEAHVKAMKVLISFIILFILYF
IGMAIEISCFTVRENKLLLMFGMTTTAIYPWGHSFILILGNSKLKQASLRVLQQLKCCEKRKNLRVT DNA-(SEQ ID NO: 19)
ATGGAAAGTGCCCTGCCGAGTATCTTCACTCTTGTAATAATTGCAGAATTCATAATTGGGAATTTGAGCAATGGATTTAT
AGTACTGATCAACTGCATTGACTGGGTCAGTAAAAGAGAGCTGTCCTCAGTCGATAAACTCCTCATTATCTTGGCAATCT
CCAGAATTGGGCTGATCTGGGAAATATTAGTAAGTTGGTTTTTAGCTCTGCATTATCTAGCCATATTTGTGTCTGGAACA
GGATTAAGAATTATGATTTTTAGCTGGATAGTTTCTAATCACTTCAATCTCTGGCTTGCTACAATCTTCAGCATCTTTTA
TTTGCTCAAAATAGCGAGTTTCTCTAGCCCTGCTTTTCTCTATTTGAAGTGGAGAGGTAAACAAAGTGATTCTGATGATAC
TGCTAGGAACCTTGGTCTTCTTATTTTTAAATCTGATACAAATAAACATGCATATAAAAGACTGGCTGGACCGATATGAA
AGAAACACAACTTGGAATTTCAGTATGAGTGACTTTGAAACATTTTCAGTGTCGGTCAAATTCACTATGACTATGTTCAG
TCTAACACCATTTACTGTGGCCTTCATCTCTTTTCTCCTGTTAATTTTCTCCCTGCAaAAACATCTCCAGAAAATGCAAC
TCAATTACAAAGGACACAGAGACCCCAGGACCAAGGTCCATAGAGCAAGGTTCCTTGAAAATTGTGATCTCATTCCTTTATTC
TATGCTAGTTTCTTTCTATGTGTTCTCATATCATGGATTTCTGAGCTGTATCAGAGCACAGTGATCTACATGCTTTGTGA
GACGATTGGAGTCTTCTCTCCTTCAAGCCACTCCTTTCTTCTGATTCTAGGAAACGCTAAGTTAAGACAGGCCTTTCTTT
TGGTGGCAGCTAAGGTATGGGCTAAACGATGA Protein-(SEQ ID NO: 20)
MESALPSIFTLVIIAEFIIGNLSNGFIVLINCIDWVSKRELSSVDKLLIILAISRIGLIWEILVSWFLALHYLAIFVSGT
GLRIMIFSWIVSNHFNLWLATIFSIFYLLKIASFSSPAFLYLKWRVNKVILMILLGTLVFLFLNLIQINMHIKDWLDRYE
RNTTWNFSMSDFETFSVSVKFTMTMFSLTPFTVAFISFLLLIFSLQKHLQKMQLNYKGHRDPRTKVHTNALKIVISFLLF
YASFFLCVLISWISELYQSTVIYMLCETIGVFSPSSHSFLLILGNAKLRQAFLLVAAKVWAKR hT2R14 sequences:
DNA-(SEQ ID NO: 21)
ATGGGTGGTGTCATAAAGAGCATATTTACATTCGTTTTAATTGTGGAATTTATAATTGGAAATTTAGGAAATAGTTTCAT
AGCACTGGTGAACTGTATTGACTGGGTCAAGGGAAGAAAGATCTCTTCGGTTGATCGGATCCTCACTGCTTTGGCAATCT
CTCGAATTAGCCTGGTTTGGTTAATATTCGGAAGCTGGTGTGTGTCTGTGTTTTTCCCAGCTTTATTTGCCACTGAAAAA
ATGTTCAGAATGCTTACTAATATCTGGACAGTGATCAATCATTTTTAGTGTCTGGTTAGCTACAGGCCTCGGTACTTTTA
TTTTCTCAAGATAGCCAATTTTTCTAACTCTATTTTTCTCTACCTAAAGTGGAGaGTTAAAAAGGTGGTTTTGGTGCTGC
TTCTTGTGACTTCGGTCTTCTTGTTTTTAAATATTGCACTGATAAACATCCATATAAATGCCAGTATCAATGGATACAGA
AGAAACAAGACTTGCAGTTCTGATTCAAGTAACTTTACACGATTTTCCAGTCTTATTGTATTAACCAGCACTGTGTTCAT
TTTCATACCCTTTACTTTGTCCCTGGCAATGTTTCTTCTCCTCATCTTCTCCATGTGGAAACATCGCAAGAAGATGCAGC
ACACTGTCAAAATATCCGGAGACGCCAGCACCAAAGCCCACAGAGGAGTTAAAAGTGTGATCACTTTCTTCCTACTCTAT
GCCATTTTCTCTCTGTCTTTTTTCATATCAGTTTGGACCTCTGAAAGGTTGGAGGAAAATCTAATTATTCTTTCCCAGGT
GATGGGAATGGCTTATCCTTCATGTCACTCATGTGTTCTGATTCTTGGAAACAAGAAGCTGAGACAGGCCTCTCTGTCAG
TGCTACTGTGGCTGAGGTACATGTTCAAAGATGGGGAGCCCTCAGGTCACAAAGAATTTAGAGAATCATCTTGA Protein-(SEQ ID NO: 22)
MGGVIKSIFTFVLIVEFIIGNLGNSFIALVNCIDWVKGRKISSVDRILTALAISRISLVWLIFGSWCVSVFFPALFATEK
MFRMLTNIWTVINHFSVWLATGLGTFYFLKIANFSNSIFLYLKWRVKKVVLVLLLVTSVFLFLNIALINIHINASINGYR
RNKTCSSDSSNFTRFSSLIVLTSTVFIFIPFTLSLAMFLLLIFSMWKHRKKMQHTVKISGDASTKAHRGVKSVITFFLLY
AIFSLSFFISVWTSERLEENLIILSQVMGMAYPSCHSCVLILGNKKLRQASLSVLLWLRYMFKDGEPSGHKEFRESS hT2R16 sequences:
DNA-(SEQ ID NO: 23)
ATGATACCCATCCAACTCACTGTCTTCTTCATGATCATCTATGTGCTTGAGTCCTTGACAATTATTGTGCAGAGCAGCCT
AATTGTTGCAGTGCTGGGCAGAGAATGGCTGCAAGTCAGAAGGCTGATGCCTGTGGACATGATTCTCATCAGCCTGGGCA
TCTCTCGCTTCTGTCTACAGTGGGCATCAATGCTGAACAATTTTTGCTCCTATTTTAATTTGAATTATGTACTTTGCAAC
TTAACAATCACCTGGCAATTTTTAATATCCTTACATTCTGGTTAAACAGCCTTTACCGTGTCTTACTGCATCAAGGT
CTCTTCTTTCACCCCATCACATCTTTCTCTGGCTGAGGTGGAGAATTTTGAGGTTGTTTCCCTGGATATTACTGGGTTCTC
TGATGATTACTTGTGTAACAATCATCCCTTCAGCTATTGGGAATTACATTCAAATTCAGTTACTCACCATGGAGCATCTA
CCAAGAAACAGCACTGTAACTGACAAACTTGAAAATTTTCATCAGTATCAGTTCCAGGCTCATACAGTTGCATTGGTTAT
TCCTTTCATCCTGTTCCTGGCCTCCACCATCTTTCTCATGGCATCACTGACCAAGCAGATACAACATCATGCACTGGTC
ACTGCAATCCAAGCATGAAAGCGCaCTTCACTGCCCTGAGGTCCCTTGCCGCTCTTATTTATTGTGTTTACCTCTTACTTT
CTAACCATACTCATCACCATTATAGGTACTCTATTTGATAAGAGATGTTGGTTATGGGTCTGGGAAGCTTTTGTCTATGC
TTTCATCTTAATGCATTCCACTTCACTGATGCTGAGCAGCCCTACGTTGAAAAGGATTCTAAAGGGAAAGTGCTAG Protein-(SEQ ID NO: 24)
MIPIQLTVFFMIIYVLESLTIIVQSSLIVAVLGREWLQVRRLMPVDMILISLGISRFCLQWASMLNNFCSYFNLNYVLCN
LTITWEFFNILTFWLNSLLTVFYCIKVSSFTHHIFLWLRWRILRLFPWILLGSLMITCVTIIPSAIGNYIQIQLLTMEHL
PRNSTVTDKLENFHQYQFQAHTVALVIPFILFLASTIFLMASLTKQIQHHSTGHCNPSMKAHFTALRSLAVLFIVFTSYF
LTILITIIGTLFDKRCWLWVWEAFVYAFILMHSTSLMLSSPTLKRILKGKC hT2R44 sequences:
DNA-(SEQ ID NO: 25)
ATGATAACTTTTCTGCCCATCATTTTTTCCATTCTAATAGTGGTTATATTTGTGATTGGAAATTTTGCTAATGGCTTCAT
AGCATTGGTAAATTCCATTGAGTGGGTCAAGAGACAAAAGATCTCCTTTGTTGACCAAATTCTCACTGCTCTGGCGGTCT
CCAGAGTTGGTTTGCTCTGGGTGTTATTACTACATTGGTATGCAACTCAGTTGAATCAGCTTTTATAGTGTAGAAGTA
AGAATTACTGCTTATAATGTCTGGGCAGTAACCAACCATTTCAGCAGCTGGCTTGCTACTAGCCTCAGCATGTTTTATTT

| (a) SEQUENCES OF CHIMERIC G PROTEIN AND hT2R GENES AND POLYPEPTIDES |
| --- |

```
GCTCAGGATTGCCAATTTCTCCAACCTTATTTTTCTTCGCATAAAGAGGAGAGTTAAGAGTGTTGTTCTGGTGATACTGT
TGGGGCCTTTGCTATTTTTGGTTTGTCATCTTTTTGTGATAAACATGGATGAGACTGTATGGACAAAAGAATATGAAGGA
AACGTGACTTGGAAGATCAAATTGAGGAGTGCAATGTACCATTCAAATATGACTCTAACCATGCTAGCAAACTTTGTACC
CCTCACTCTGACCCTGATATCTTTTCTGCTGTTAATCTGTTCTCTGTGTAAACATCTCAAGAAGATGCAaCTCCATGGCA
AAGGATCTCAAGATCCCAGCACCAAGGTCCACATAAAAGCTTTGCAAACTGTGACCTCCTTTCTTCGTTATGTGCCATT
TACTTTCTGTCCATGATCATATCAGTTTGTAATTTGGGGAGGCTGGAAAAGCAACCTGTCTTCATGTTCTGCCAAGCTAT
TATATTCAGCTATCCTTCAACCCACCCATTCATCCTGATTTTGGGAAACAAGAAGCTAAAGCAGATTTTTCTTTCAGTTT
TGCGGCATGTGAGGTACTGGGTGAAAGACAGAAGCCTTCGTCTCCATAGATTCACAAGAGGGGCATTGTGTGTCTTCTAG

Protein-(SEQ ID NO: 26)
MITFLPIIFSILIVVIFVIGNFANGFIALVNSIEWVKRQKISFVDQILTALAVSRVGLLWVLLLHWYATQLNPAFYSVEV
RITAYNVWAVTNHFSSWLATSLSMFYLLRIANFSNLIFLRIKRRVKSVVLVILLGPLLFLVCHLFVINMDETVWTKEYEG
NVTWKIKLRSAMYHSNMTLTMLANFVPLTLTLISFLLLICSLCKHLKKMQLHGKGSQDPSTKVHIKALQTVTSFLLLCAI
YFLSMIISVCNLGRLEKQPVFMFCQAIIFSYPSTHPFILILGNKKLKQIFLSVLRHVRYWVKDRSLRLHRFTRGALCVF hT2R50 sequences:
DNA-(SEQ ID NO: 27)
ATGATAACTTTTCTGCCCATCATATTTTCCATTCTAGTAGTGGTTACATTTGTTATTGGAAATTTTGCTAATGGCTTCAT
AGCGTTGGTgAATTCCACCGAGTGGGTGAAGAGACAAAAGATCTCCTTTGCTGACCAAATTGTCACTGCTCTGGCGGTCT
CCAGAGTTGGTTTGCTCTGGGTGTTATTATTAAATTGGTATTCAACTGTGTTGAATCCAGCTTTTTATAGTGTAGAgTTA
AGAACTACTGCTTATAATATCTGGGCAGTAACCGGCCATTTCAGCAACTGGCTGCTACTAGCCTCAGCATATTTTATTT
GCTCAAGATTGCCAATTTCTCCAACCTTATTTTTCTTCGCTTAAAGAGGAGAGTTAAGAGTGTCATTCTGGTGGTGCTGT
TGGGGCCTTTGCTATTTTTGGCTTGTCATCTTTTTGTGGTAAACATGAATCAGATTGTATGGACAAAAGAATATGAAGGA
AACGTGACTTGGAAGATCAAATTGAGGCGTGCAATGTACCTTTCAGATACGACTGTAACCATGCTAGCAAACTTAGTACC
CTTTACTGTAACCCTGATATCTTTTCTGCTGTTAGTCTGTTCTCTGTGTAAACATCTCAAGAAGATGCAGCTCCATGGCA
AAGGATCTCAAGATCCCAGTACCAAGGTCCACATAAAAGTTTTGCAAACTGTGATCTCCTTCTTCTTGTTATGTGCCATT
TACTTTGTGTCTGTAATAATATCAGTTTGGAGTTTTAAGAATCTGGAAAACAAACCTGTCTTCATGTTCTGCCAAGCTAT
TGGATTCAGCTGTTCTTCAGCCCACCCGTTCATCCTGATTTGGGGAAACAAGAAGCTAAAGCAGACTTATCTTTCAGTTT
TGTGGCAAATGAGGTACTGA Protein-(SEQ ID NO: 28)
MITFLPIIFSILVVVTFVIGNFANGFIALVNSTEWVKRQKISFADQIVTALAVSRVGLLWVLLLNWYSTVLNPAFYSVEL
RTTAYNIWAVTGHFSNWPATSLSIFYLLKIANFSNLIFLRLKRRVKSVILVLLGPLLFLACHLFVVNMNQIVWTKEYEG
NMTWKIKLRRAMYLSDTTVTMLANLVPFTVTLISFLLLVCSLCKHLKKMQLHGKGSQDPSTKVHIKVLQTVISFFLLCAI
YFVSVIISVWSFKNLENKPVFMFCQAIGFSCSSAHPFILIWGNKKLKQTYLSVLWQMRY hT2R51 sequences:
DNA-(SEQ ID NO: 29)
ATGTTGACTCTAACTCGCATCCGCACTGTGTCCTATGAAGTCAGGAGTACATTTCTGTTCATTTCAGTCCTGGAGTTTGC
AGTGGGGTTTCTGACCAATGCCTTCGTTTTCTTGGTGAATTTTTGGGATGTAGTGAAGAGGCAGcCACTGAGCAACAGTG
ATTGTGTGCTGCTGTGTCTCAGCATCAGCCGGCTTTTCCTGCATGGACTGCTGTTCCTGAGTGCTATCCAGCTTACCCAC
TTCCAGAAGTTGAGTGAACCACTGAACCACAGCTACCAAGCCATCATCATGCTATGGATGATTGCAAACCAAGCCAACCT
CTGGCTTGCTGCCTGCCTCAGCCTGCTTTACTGCTCCAAGCTCATCCGTTTCTCTCACACCTTCCTGATCTGCTTGGCAA
GCTGGGTCTCCAGGAAGATCTCCCAGATGCTCCTGGGTATTATTCTTTGCTCCTGCATCTGCACTGTCCTCTGTGTTTGG
TGCTTTTTTAGCAGACCTCACTTCACAGTCACAACTGTGCTATTCATGAATAACAATACAAGGCTCAACTGGCAGATTAA
AGATCTCAATTTATTTTATTCCTTTCTTCTGCTATCTGTGGTCTGTGCCTCCTTTCCTATTGTTTCTGGTTTCTTCTG
GGATGCTGACTGTCTCCCTGGGAAGGCACATGAGGACAATGAAGGTCTATACCAGAAACTCTCGTGACCCCAGCCTGGAG
GCCCACATTAAAGCCCTCAAGTCTCTTGCTCTCCTTTTTCTGCTTCTTTGTGATATCATCCTGTGcTGCCTTCATCTCTGT
GCCCCTACTGATTCTGTGGCGCGACAAAATAGGGGTGATGGTTTGTGTTGGGATAATGGCAGCTTGTCCCTCTGGGCATG
CAGCCgTCCTGATCTCAGGCAATGCCAAGTTGAGGAGAGCTGTGATGACCATTCTGCTCTGGGCTCAGAGCAGCCTGAAG
GTAAGAGCCGACCACAAGGCAGATTCCCGGACACTGTGCTGA Protein-(SEQ ID NO: 30)
MLTLTRIRTVSYEVRSTFLFISVLEFAVGFLTNAFVFLVNFWDVVKRQPLSNSDCVLLCLSISRLFLHGLLFLSAIQLTH
FQKLSEPLNHSYQAIIMLWMIANQANLWLAACLSLLYCSKLIRFSHTFLICLASWVSRKISQMLLGIILCSCICTVLCVW
CFFSRPHFTVTTVLFMNNNTRLNWQIKDLNLFYSFLFCYLWSVPPFLLFLVSSGMLTVSLGRHMRTMKVYTRNSRDPSLE
AHIKALKSLVSFFCFFVISSCAAFISVPLLILWRDKIGVMVCVGIMAACPSGHAAVLISGNAKLRRAVMTILLWAQSSLK
VRADHKADSRTLC hT2R54 sequences:
DNA-(SEQ ID NO: 31)
ATGACTAAACTCTGCGATCCTGCAGAAAGTGAATTGTCGCCATTTCTCATCACCTTAATTTTAGCAGTTTTACTTGCTGA
ATACCTCATTGGTATCATTGCAAATGGTTTCATCATGGCTATACATGCAGCTGAATGGGTTCAAAATAAGGCAGTTTCCA
CAAGTGGCAGGATCCTGGTTTTCCTGAGTGTATCCAGAATGGCTCTCCAAAGCCTCATGATGTTAGAAATTACCATCAGC
TCAACCTCCCTAAGTTTTTATTCTGAAGACGCTGTATATTATGCATTCAAAATAAGTTTTATATTCTTAAATTTTTGTAG
CCTGTGGTTTGCTGCCTGGCTCAGTTTCTTCTACTTTGTGAAGATTGCCAATTTCTCCTACCCCTTTTCCTCAAACTGA
GGTGGAGAATTACTGGATTGATACCCTGGCTTCTGTGGCTGTCCGTGTTATTTCCTTCAGTCACAGCATGTTCTGCATC
AACATCTGCACTGTGTATTGTAACAATTCTTTCCCTATCCACTCCTCCAACTCCACTAAGAAAACATACTTGTCTGAGAT
CAATGTGGTCGGTCTGGCTTTTTTCTTTAACCTGGGGATTGGACTCCTCTGATCATGTTCATCTCGACAGCCCACCCTGC
TGATCCTCTCTCTCAAGAGACACACCCTACACATGGGAAGCAATGCCACAGGGTCCAACGACCCCAGCATGGAGGCTCAC
ATGGGGGCCATCAAAGCTATCAGCTACTTTCTCATTCTCTACATTTTCAATGCAGTTGCTCTGTTTATCTACCTGTCCAA
CATGTTTGACATCAACAGTCTGTGGAATAATTTGTGCCAGATCATCATGGCTGCCTACCCTGCCAGCCACTCAATTCTAC
TGATTCAAGATAACCCTGGGCTGAAGAGAGCCTGGAAGCGGCTTCAGCTTCGACTTCATCTTTACCCAAAAGAGTGGACT
CTGTGA
```

| (a) SEQUENCES OF CHIMERIC G PROTEIN AND hT2R GENES AND POLYPEPTIDES |
| --- |

Protein-(SEQ ID NO: 32)
MTKLCDPAESELSPFLITLILAVLLAEYLIGIIANGFIMAIHAAEWVQNKAVSTSGRILVFLSVSRIALQSLMMLEITIS
STSLSFYSEDAVYYAPKISFIFLNFCSLWFAAWLSFFYFVKIANFSYPLFLKLRWRITGLIPWLLWLSVFISFSHSMFCI
NICTVYCNNSFPIHSSNSTKKTYLSEINVVGLAFFFNLGIVTPLIMFILTATLLILSLKRHTLHMGSNATGSNDPSMEAH
MGAIKAISYFLILYIFNAVALFIYLSNMFDINSLWNNLCQIIMAAYPASHSILLIQDNPGLRRAWKRLQLRLHLYPKEWT
L hT2R55 sequences:
DNA-(SEQ ID NO: 33)
ATGGCAACGGTGAACACAGATGCCACAGATAAAGACATATCCAAGTTCAAGGTCACCTTCACTTTGGTGGTCTCCGGAAT
AGAGTGCATCACTGGCATCCTTGGGAGTGGCTTCATCACGGCCATCTATGGAGCTTGGAGTGGGCCAGGGGCAAAACACTCC
CCACTGGTGACCGCATTATGTTGATGCTGAGCTTTTCCAGGCTCTTGCTACAGATTTGGATGATGCTGGAGAACATTTTC
AGTCTGCTATTCCGAATTGTTTATAACCAAAACTCAGTGTATATCCTCTTCAAAGTCATCACTGTCTTTCTGAACCATTC
CAATCTCTGGTTTGCTGCCTGGCTCAAAGTCTTCTATTGTCTTAGAATTGCAAACTTCAATCATCCTTTGTTCTTCCTGA
TGAAGAGGAAAATCATAGTGCTGATGCCTTGGCTTCTCAGGCTGTCAGTGTTGGTTTCCTTAAGCTTCAGCTTTCCTCTC
TCGAGAGATGTCTTCAATGTGTATGTGAATAGCTCCATTCCTATCCCCTCCTCCAACTCCACGGAGAAGAAGTACTTCTC
TGAGACCAATATGGTCAACCTGGTATTTTTCTATAACATGGGGATCTTCGTTCCTCTGATCATGTTCATCCTGGCAGCCA
CCCTGCTGATCCTCTCTCTCAAGAGACACACCCTACACATGGGAAGCAATGCCACAGGGTCCAGGGACCCCAGCATGAAG
GCTCACATAGGGGCCATCAAAGCCACCAGCTACTTTCTCATCCTCTACATTTTCAATGCAATTGCTCTATTTCTTTCCAC
GTCCAACATCTTTGACACTTACAGTTCCTGGAATATTTTGTGCAAGATCATCATGGCTGCCTACCCTGCCGGCCACTCAG
TACAACTGATCTTGGGCAACCCTGGGCTGAGAAGAGCCTGGAAGCGGTTTCAGCACCAAGTTCCTCTTTACCTAAAAGGG
CAGACTCTGTGA Protein-(SEQ ID NO: 34)
MATVNTDATDKDISKFKVTFTLVVSGIECITGILGSGFITAIYGAEWARGKTLPTGDRIMLMLSFSRLLLQIWMMLENIF
SLLFRIVYNQNSVYILPKVITVFLNHSNLWFAAWLKVFYCLRIANFNHPLFFLMKRKIIVLMPWLLRLSVLVSLSFSFPL
SRDVFNVYVNSSIPIPSSNSTEKKYFSETNMVNLVFFYNMGIFVPLIMFILAATLLILSLKRHTLHMGSNATGSRDPSMK
AHIGAIKATSYFLILYIFNAIALFLSTSNIFDTYSSWNILCKIIMAAYPAGHSVQLILGNPGLRRAWKRFQHQVPLYLKG
QTL hT2R61 sequences:
DNA-(SEQ ID NO: 35)
ATGATAACTTTTCTACCCATCATTTTTTCCAGTCTGGTAGTGGTTACATTTGTTATTGGAAATTTTGCTAATGGCTTCAT
AGCACTGGTAAATTCCATTGAGTGGTTCAAGAGACAAAAGATCTCCTTTGCTGACCAAATTCTCACTGCTCTGGCGGTCT
CCAGAGTTGGTTTGCTCTGGGTATTATTATTAAACTGGTATTCAACTGTGTTGAATCCAGCTTTTAATAGTGTAGAAGTA
AGAACTACTGCTTATAATATCTGGGCAGTGATCAACCATTTCAGCAACTGGCTTGCTACTACCCTCAGCATATTTTATTT
GCTCAAGATTGCCAATTTCTCCAACTTTATTTTTCTTCACTTAAAGAGGAGAGTTAAGAGTGTCATTCTGGTGATGTTGT
TGGGGCCTTTGCTATTTTTGGCTTGTCATCTTTTTGTGATAAACATGAATGAGATTGTGCGGACAAAAGAATTTGAAGGA
AACATGACTTGGAAGATCAAATTGAAGAGTGCAATGTACTTTTCAAATATGACTGTAACCATGGTAGCAAACTTAGTACC
CTTCACTCTGACCCTACTATCTTTTATGCTGTTAATCTGTTCTTTGTGTAAACATCTCAAGAAGATGCAGCTCCATGGTA
AAGGATCTCAAGATCCCAGCACCAAGGTCCACATAAAAGCTTTGCAAACTGTGATCTCCTTCCTTCTTGTTATGTGCCATT
TACTTTCTGTCCATAATGATATCAGTTTGGAGTTTTGGAAGTCTGGAAAACAAACCTGTCTTCATGTTCTGCAAAGCTAT
TAGATTCAGCTATCCTTCAATCCACCCATTCATCCTGATTTGGGGAAACAAGAAGCTAAAGCAGACTTTTCTTTCAGTTT
TTTGGCAAATGAGGTACTGGGTGAAAGGAGAGAAGACTTCATCTCCATAG Protein-(SEQ ID NO: 36)
MITFLPIIFSSLVVVTFVIGNFANGFIALVNSIEWFKRQKISFADQILTALAVSRVGLLWVLLLNWYSTVLNPAFNSVEV
RTTAYNIWAVINHFSNWLATTLSIFYLLKIANFSNFIFLHLKRRVKSVILVMLLGPLLFLACHLPVINMNEIVRTKEFEG
NMTWKIKLKSAMYFSNMTVTMVANLVPFTLTLLSFMLLICSLCKHLKKMQLHGKGSQDPSTKVHIKALQTVISFLLLCAI
YFLSIMISVWSFGSLENKPVFMFCKAIRFSYPSIHPFILIWGNKKLKQTFLSVFWQMRYWVKGEKTSSP hT2R64 sequences:
DNA-(SEQ ID NO: 37)
ATGACAACTTTTATACCCATCATTTTTTCCAGTGTGGTAGTGGTTCTATTTGTTATTGGAAATTTTGCTAATGGCTTCAT
AGCATTGGTAAATTCCATTGAGCGGGTCAAGAGACAAAAGATCTCTTTTGCTGACCAGATTCTCACTGCTCTGGCGGTCT
CCAGAGTTGGTTTGCTCTGGGTATTATTATTAAATTGGTATTCAACTGTGTTTAATCCAGCTTTTTATAGTGTAGAAGTA
AGAACTACTGCTTATAATGTCTGGGCAGTAACCGGCCATTTCAGCAACTGGCTTGCTACTAGCCTCAGCATATTTTATTT
GCTCAAGATTGCCAATTTCTCCAACCTTATTTTTCTTCACTTAAAGAGGAGAGTTAAGAGTGTCATTCTGGTGATGCTGT
TGGGGCCTTTACTATTTTTGGCTTGTCAACTTTTTGTGATAAACATGAAAGAGATTGTACGGACAAAAGAATATGAAGGA
AACTTGACTTGGAAGATCAAATTGAGGAGTGCAGTGTACCTTTCAGATGCGACTGTAACCACGCTAGGAAACTTAGTGCC
CTTCACTCTGACCCTGCTATGTTTTTTGCTGTTAATCTGTTCTTTGTGTAAACATCTCAAGAAGATGCAGCTCCATGGTA
AAGGATCTCAAGATCCCAGCACCAAGGTCCACATAAAAGCTTTGCAAACTGTGATCTTTTTCCTTCTTGTTATGTGCCGTT
TACTTTCTGTCCATAATGATATCAGTTTGGAGTTTTGGGAGTCTGGAAAACAAACCTGTCTTCATGTTCTGCAAAGCTAT
TAGATTCAGCTATCCTTCAATCCACCCATTCATCCTGATTTGGGGAAACAAGAAGCTAAAGCAGACTTTTCTTTCAGTTT
TGCGGCAAGTGAGGTACTGGGTGAAGGGAGAGAAGCCTTCATCTCCATAG Protein-(SEQ ID NO: 38)
MTTFIPIIFSSVVVVLFVIGNFANGFIALVNSIEWVKRQKISFADQILTALAVSRVGLLWVLLLNWYSTVFNPAFYSVEV
RTTAYNVWAVTGHFSNWLATSLSIFYLLKIANFSNLIFLHLKRRVKSVILVMLLGPLLFLACQLFVINMKEIVRTKEYEG
NMTWKIKLRSAVYLSDATVTTLGNLVPFTLTLLCFLLLICSLCKHLKKMQLHGKGSQDPSTKVHIKVLQTVIFFLLLCAI
YFLSIMISVWSFGSLENKPVFMFCKAIRFSYPSIHPFILIWGNKKLKQTFLSVLRQVRYWVKGEKPSSP hT2R65 sequences:
DNA-(SEQ ID NO: 39)
ATGATGTGTTTTCTGCTCATCATTTCATCAATTCTGGTAGTGTTTGCATTTGTTCTTGGAAATGTTGCCAATGGCTTCAT
AGCCCTAGTAAATGTCATTGACTGGGTTAACACACGAAAGATCTCCTCAGCTGAGCAAATTCTCACTGCTCTGGTGGTCT
CCAGgATTGGTTTACTCTGGGTCATGTTATTCCTTTGGTATGCAACTGTGTTTAATTCTGCTTTATATGGTTTAGAAGTA

| (a) SEQUENCES OF CHIMERIC G PROTEIN AND hT2R GENES AND POLYPEPTIDES |
|---|
| AGAATTGTTGCTTCTAATGCCTGGGCTGTAACGAACCATTTCAGCATGTGGCTTGCTGCTAGCCTCAGCATATTTTGTTT
GCTCAAGATTGCCAATTTCTCCAACCTTATTTCTCTCCACCTAAAGAAGAGAATTAAGAGTGTTGTTCTGGTGATACTGT
TGGGGCCCTTGGTATTTCTGATTTGTAATCTTGCTGTGATAACCATGGATGAGAGAGTGTGGACAAAAGAATATGAAGGA
AATGTGACTTGGAAGATCAAATTGAGGAATGCAATACACCTTTCAAGCTTGACTGTAACTACTCTAGCAAACCTCATACC
CTTTACTCTGAGCCTAATATGTTTTCTGCTGTTAATCTGTTCTCTTTGTAAACATCTCAAGAAGATGCGGCTCCATAGCA
AAGGATCTCAAGATCCCAGCACCAAGGTCCATATAAAAGCTTTGCAAACTGTGACCTCCTTCCTCATGTTATTTGCCATT
TACTTTCTGTGTATAATCACATCAACTTGGAATCTTAGGACACAGCAGAGCAAACTTGTACTCCTGCTTTGCCAAACTGT
TGCAATCATGTATCCTTCATTCCACTCATTCATCCTGATTATGGGAAGTAGGAAGCTAAAACAGACCTTTCTTTCAGTTT
TGTGGCAGATGACACGCTGA

Protein-(SEQ ID NO: 40)
MMCFLLIISSILVVFAFVLGNVANGFIALVNVIDWVNTRKISSAEQILTALVVSRIGLLWVMLFLWYATVFNSALYGLEV
RIVASNAWAVTNHFSMWLAASLSIFCLLKIANFSNLISLHLKKRIKSVVLVILLGPLVFLICNLAVITMDERVWTKEYEG
NVTWKIKLRNAIHLSSLTVTTLANLIPFTLSLICFLLLICSLCKHLKKMRLHSKGSQDPSTKVHIKALQTVTSFLMLFAI
YFLCIITSTWNLRTQQSKLVLLLCQTVAIMYPSFHSFILIMGSRKLKQTFLSVLWQMTR hT2R67 sequences:
DNA-(SEQ ID NO: 41)
ATGATAACTTTTCTATACATTTTTTTTCAATTCTAATAATGGTTTTATTTGTTCTCGGAAACTTTGCCAATGGCTTCAT
AGCACTGGTAAATTTCATTGACTGGGTGAAGAGAAAAAAGATCTCCTCAGCTGACCAAATTCTCACTGCTCTGGCGGTCT
CCAGAATTGGTTTGCTCTGGGCATTATTATTAAATTGGTATTTAACTGTGTTGAATCCAGCTTTTTATAGTGTAGAATTA
AGAATTACTTCTTATAATGCCTGGGTTGTAACCAACCATTTCAGCATGTGGCTTGCTGCTAACCTCAGCATATTTTATTT
GCTCAAGATTGCCAATTTCTCCAACCTTCTTTTTCTTCATTTAAAGAGGAGAGTTAGGAGTGTCATTCTGGTGATACTGT
TGGGGACTTTGATATTTTTGGTTTGTCATCTTCTTGTGGCAAACATGGATGAGAGTATGTGGGCAGAAGAATATGAAGGA
AACATGACTGGGAAGATGAAATTGAGGAATACAGTACATCTTTCATATTTGACTGTAACTACCCTATGGAGCTTCATACC
CTTTACTCTGTCCCTGATATCTTTTCTGATGCTAATCTGTTCTCTGTAAACATCTCAAGAAGATGCAGCTCCATGGAG
AAGGATCGCAAGATCTCAGCACCAAGGTCCACATAAAAGCTTTGCAAACTCTGATCTCCTTCCTCTTGTTATGTGCCATT
TTCTTTCTATTCCTAATCGTTTCGGTTTGGAGTCCTAGGAGGCTGCGGAATGACCCGGTTGTCATGGTTAGCAAGGCTGT
TGGAAACATATATCTTGCATTCGACTCATTCATCCTAATTTGGAGAACCAAGAAGCTAAAACACACCTTTCTTTTGATTT
TGTGTCAGATTAGGTGCTGA Protein-(SEQ ID NO: 42)
MITFLYIFFSILIMVLFVLGNFANGFIALVNFIDWVKRKKISSADQILTALAVSRIGLLWALLLNWYLTVLNPAFYSVEL
RITSYNAWVVTNHFSMWLAANLSIFYLLKIANFSNLLFLHLKRRVRSVILVILLGTLIFLVCHLLVANMDESMWAEEYEG
NMTGKMKLRNTVHLSYLTVTTLWSFIPFTLSLISFLMLICSLCKHLKKMQLHGEGSQDLSTKVHIKALQTLISFLLLCAI
FFLFLIVSVWSPRRLRNDPVVMVSKAVGNIYLAFDSFILIWRTKKLKHTFLLILCQIRC hT2R71 sequences:
DNA-(SEQ ID NO: 43)
ATGCAAGCAGCACTGACGGCCTTCTTCGTGTTGCTCTTTAGCCTGCTGAGTCTTCTGGGGATTGCAGCGAATGGCTTCAT
TGTGCTGGTGCTGGGCAGGGAGTGGCTGCGATATGGCAGGTTGCTGCCCTTGGATATGATCCTCATTAGCTTGGGTGCCT
CCCGCTTCTGCCTGCAGTTGGTTGGGACGGTGCACAACTTCTACTACTCTGCCCAGAAGGTCGAGTACTCTGGGGGTCTC
GGCCGACAGTTCTTCCATCTACACTGGCACTTCCTGAACTCAGCCACCTTCTGGTTTTGCAGCTGGCTCAGTGTCCTGTT
CTGTGTGAAGATTGCTAACATCACACACTCCACCTTCCTGTGGCTGAAGTGGAGGTTCCCAGGGTGGGTGCCCTGGCTCC
TGTTGGGCTCTGTCCTGATCTCCTTCATCATAACCCTGCTGTTTTTTTGGGTGAACTACCCTGTATATCAAGAATTTTTA
ATTAGAAAATTTTCTGGGAACATGACCTACAAGTGGAATAACGGATAGAAACATACTATTTCCCATCCCTGAAACTGGT
CATCTGGTCAATTCCTTTTTCTGTTTTTCTGGTCTCAATTATGCTGTTAATTAATTCTCTGAGGAGGCATACTCAGAGAA
TGCAGCACAACGGGCACAGCCTGCAGGACCCCAGCACCCAGGCTCACACCAGAGCTCTGAAGTCCCTCATCTCCTTCCTC
ATTCTTTATGCTCTGTCCTTTCTGTCCCTGATCATTGATGCCGCAAAATTTATCTCCATGCAGAACGACTTTTACTGGCC
ATGGCAAATTGCAGTCTACCTGTGCATATCTGTCCATCCCTTCATCCTCATCTTCAGCAACCTCAAGCTTCGAAGCGTGT
TCTCGCAGCTCCTGTTGTTGGCAAGGGGCTTCTGGGTGGCCTAG Protein-(SEQ ID NO: 44)
MQAALTAFFVLLFSLLSLLGIAANGFIVLVLGREWLRYGRLLPLDMILISLGASRFCLQLVGTVHNFYYSAQKVEYSGGL
GRQFFHLHWHFLNSATFWFCSWLSVLFCVKIANITHSTFLWLKWRFPGWVPWLLLGSVLISFIITLLFFWVNYPVYQEFL
IRKFSGNMTYKWNTRIETYYFPSLKLVIWSIPFSVFLVSIMLLINSLRRHTQRMQHNGHSLQDPSTQAHTRALKSLISFL
ILYALSFLSLIIDAAKFISMQNDFYWPWQIAVYLCISVHPFILIFSNLKLRSVFSQLLLLARGFWVA hT2R75 sequences:
DNA-(SEQ ID NO: 45)
ATGATAACTTTTCTGCCCATCATTTTTTCCATTCTAATAGTGGTTACATTTGTGATTGGAAATTTTGCTAATGGCTTCAT
AGCATTGGTAAATTCCATTGAGTGGTTCAAGAGACAAAAGATCTCTTTTGCTGACCAAATTCTCACTGCTCTGGCAGTCT
CCAGAGTTGGTTTACTCTGGGTATTAGTATTAAATTGGTATGCAACTGAGTTGAATCCAGCTTTTAACAGTATAGAAGTA
AGAATTACTGCTTACAATGTCTGGGCAGTAATCAACCATTTCAGCAACTGGCTTGCTACTAGCCTCAGCATATTTTATTT
GCTCAAGATTGCCAATTTCTCCAACCTTATTTTTCTTCACTTAAAGAGGAGAGTTAAGAGTGTTGTTCTGGTGATACTAT
TGGGGCCTTTGCTATTTTGGTTTGTCATCTTTTTGTGATAAACATGAATCAGATTATATGGACAAAAGAATATGAAGGA
AACATGACTGGGAAGATCAAACTGAGGAGTGCAATGTACCTTTCAAATACAACGGTAACCATCCTAGCAAACTTAGTTCC
CTTCACTCTGACCCTGATATCTTTTCTGCTGTTAATCTGTTCTCTGTAAACATCTCAAAAAGATGCAGCTCCATGGCA
AAGGATCTCAAGATCCCAGCATGAAGGTCCACATAAAAGCTTTGCAAACTGTGACCTCCTTCCTCTTGTTATGTGCCATT
TACTTTCTGTCCATAATCATGTCAGTTTGGAGTTTTGAGAGTCTGGAAAACAAACCTGTCTTCATGTTCTGCGAAGCTAT
TGCATTCAGCTATCCTTCAACCCACCCATTCATCCTGATTGGGGAAACAAGAAGCTAAAGCAGACTTTTCTTTCAGTTT
TGTGGCATGTGAGGTACTGGGTGAAAGGAGAGAAGCCTTCATCTTCATAG Protein-(SEQ ID NO: 46)
MITFLPIIFSILIVVTFVIGNFANGFIALVNSIEWFKRQKISFADQILTALAVSRVGLLWVLVLNWYATELNPAFNSIEV
RITAYNVWAVINHFSNWLATSLSIFYLLKIANFSNLIFLHLKRRVKSVVLVILLGPLLFLVCHLFVINMNQIIWTKEYEG

(a) SEQUENCES OF CHIMERIC G PROTEIN AND hT2R GENES AND POLYPEPTIDES

```
NMTWKIKLRSAMYLSNTTVTILANLVPFTLTLISFLLLICSLCKHLKKMQLHGKGSQDPSMKVHIKALQTVTSFLLLCAI
YFLSIIMSVWSFESLENKPVFMFCEAIAFSYPSTHPFILIWGNKKLKQTFLSVLWHVRYWVKGEKPSSS hT2R76 sequences:
DNA-(SEQ ID NO: 47)
ATGAATGGAGACCACATGGTTCTAGGATCTTCGGTGACTGACAAGAAGGCCATCATCTTGGTTACCATTTTACTCCTTTT
ACGCCTGGTAGCAATAGCAGGCAATGGCTTCATCACTGCTGCTCTGGGCGTGGAGTGGGTGCTACGGAGAATGTTGTTGC
CTTGTGATAAGTTATTGGTTAGCCTAGGGGCCTCTCGCTTCTGTCTGCAGTCAGTGGTAATGGGTAAGACCATTTATGTT
TTCTTGCATCCGATGGCCTTCCCATACAACCCTGTACTGCAGTTTCTAGCTTTCCAGTGGGACTTCCTGAATGCTGCCAC
CTTATGGTCCTCTACCTGGCTCAGTGTCTTCTATTGTGTGAAAATTGCTACCTTCACCCACCCTGTCTTCTTCTGGCTAA
AGCACAAGTTGTCTGGGTGGCTACCATGGATGCTCTTCAGCTCTGTAGGGCTCTCCAGCTTCACCACCATTCTATTTTTC
ATAGGCAACCACAGAATGTATCAGAACTATTTAAGGAACCATCTACAACCTTGGAATGTCACTGGCGATAGCATACGGAG
CTACTGTGAGAAATTCTATCTCTTCCCTCTAAAAATGATTACTTGGACAATGCCCACTGCTGTCTTTTTCATTTGCATGA
TTTTGCTCATCACATCTCTGGGAAGACACAGGAAGAAGGCTCTCCTTACAACCTCAGGATTCCGAGAGCCCAGTGTGCAG
GCACACATAAAGGCTCTGCTGGCTCTCCTCTCTTTTGCCATGCTCTTCATCTCATATTTCCTGTCACTGGTGTTCAGTGC
TGCAGGTATTTTTCCACCTCTGGACTTTAAATTCTGGGTGTGGGAGTCAGTGATTTATCTGTGTGCAGCAGTTCACCCCA
TCATTCTGCTCTTCAGCAACTGCAGGCTGAGAGCTGTGCTGAAGAGTCGcCGTTCCTCAAGGTGTGGGACACCTTGA Protein-(SEQ ID NO: 48)
MNGDHMVLGSSVTDKKAIILVTILLLLRLVAIAGNGFITAALGVEWVLRRMLLPCDKLLVSLGASRFCLQSVVMGKTIYV
FLHPMAFPYNPVLQFLAFQWDFLNAATLWSSTWLSVFYCVKIATFTHPVFFWLKHKLSGWLPWMLFSSVGLSSFTTILFF
IGNHRMYQNYLRNHLQPWNVTGDSIRSYCEKFYLFPLKMITWTMPTAVFFICMILLITSLGRHRKKALLTTSGFREPSVQ
AHIKALLALLSFAMLFISYFLSLVFSAAGIFPPLDFKFWVWESVIYLCAAVHPIILLFSNCRLRAVLKSRRSSRCGTP
```

While the foregoing detailed description has described several embodiments of the present invention, it is to be understood that the above description is illustrative only and not limiting of the disclosed invention. The invention is to be limited only by the claims which follow.

The invention claimed is:

1. An assay for identifying a compound which modulates a human T2R bitter taste receptor polypeptide wherein said polypeptide specifically responds to caffeine, which assay comprises: i. screening a compound for its effect on caffeine to induce the activation of (1) said bitter taste receptor polypeptide which is a polypeptide that possesses at least 90% sequence identity to the polypeptide of SEQ ID NO:36 (2) or is a polypeptide encoded by a nucleic acid sequence contained in SEQ ID NO: 37, and/or (3) is a polypeptide encoded by a nucleic acid sequence that hybridizes to the complement of the nucleic acid sequence of SEQ ID:35 under stringent hybridization conditions, which possesses at least 90% sequence identity to the polypeptide of SEQ ID NO:36 and ii. determining whether said compound modulates bitter taste based on its effect on the activation of said polypeptide by caffeine; and iii. identifying said compound as a potential bitter taste modulator if it modulates the activation of said polypeptide by caffeine.

2. The assay of claim 1, wherein polypeptide possesses at least 90% sequence identity to the polypeptide of SEQ ID NO:36.

3. The assay of claim 1, wherein the polypeptide possesses at least 95% sequence identity to the polypeptide of SEQ ID NO:36.

4. The assay of claim 1, wherein the polypeptide possesses at least 98% sequence identity to the polypeptide of SEQ ID NO:36.

5. The assay of claim 1, wherein the polypeptide possesses at least 99% sequence identity to the polypeptide of SEQ ID NO:36.

6. The assay of claim 1, wherein the polypeptide is identical to the polypeptide of SEQ ID NO:36.

* * * * *